United States Patent
Edwards et al.

(10) Patent No.: US 10,071,203 B2
(45) Date of Patent: Sep. 11, 2018

(54) DEVICES, SYSTEMS AND METHODS FOR MEDICAMENT DELIVERY

(71) Applicant: kaleo, Inc., Richmond, VA (US)

(72) Inventors: Evan Thomas Edwards, Charlottesville, VA (US); Eric Shawn Edwards, Moseley, VA (US); Mark J. Licata, Doswell, VA (US)

(73) Assignee: kaleo, Inc., Richmond, VA (US)

( * ) Notice: Subject to any disclaimer, the term of this patent is extended or adjusted under 35 U.S.C. 154(b) by 338 days.

(21) Appl. No.: 14/875,085

(22) Filed: Oct. 5, 2015

(65) Prior Publication Data
US 2016/0022909 A1    Jan. 28, 2016

Related U.S. Application Data

(63) Continuation of application No. 13/748,728, filed on Jan. 24, 2013, now Pat. No. 9,149,579, which is a
(Continued)

(51) Int. Cl.
*A61M 5/24* (2006.01)
*A61M 5/20* (2006.01)
(Continued)

(52) U.S. Cl.
CPC .......... *A61M 5/2046* (2013.01); *A61M 5/19* (2013.01); *A61M 5/2033* (2013.01);
(Continued)

(58) Field of Classification Search
CPC .......... A61M 5/2033; A61M 2005/206; A61M 5/326
See application file for complete search history.

(56) References Cited

U.S. PATENT DOCUMENTS

| 2,960,087 A | 11/1960 | Uytenbogaart |
| 3,055,362 A | 9/1962 | Uytenbogaart |

(Continued)

FOREIGN PATENT DOCUMENTS

| DE | 2019296 | 11/1971 |
| EP | 1518575 A1 | 3/2005 |

(Continued)

OTHER PUBLICATIONS

Third Party Observations filed in European Patent Application No. 07864490.3, dated Aug. 22, 2016.
(Continued)

*Primary Examiner* — Aarti Bhatia Berdichevsky

(57) ABSTRACT

An apparatus includes a movable member and a valve coupled to the movable member. The movable member is configured to be disposed within a housing of a medical device and has a first end portion and second end portion. A portion of the first end portion is configured to define a portion of a boundary of a gas chamber. The first end portion defines an opening configured to be in fluid communication between the gas chamber and an area outside the gas chamber. The second end portion is configured to be coupled to a needle configured to deliver a medicament into a body. The valve is configured to selectively allow fluid communication between the gas chamber and the area outside the gas chamber through the opening defined by the first end portion of the movable member.

23 Claims, 47 Drawing Sheets

Related U.S. Application Data continuation of application No. 13/090,392, filed on Apr. 20, 2011, now Pat. No. 8,361,029, which is a continuation of application No. 11/566,422, filed on Dec. 4, 2006, now Pat. No. 7,947,017, which is a continuation-in-part of application No. 10/515,571, filed as application No. PCT/US2004/039386 on Nov. 23, 2004, now Pat. No. 7,416,540, said application No. 11/566,422 is a continuation-in-part of application No. 10/572,148, filed as application No. PCT/US2006/003415 on Feb. 1, 2006, now Pat. No. 7,749,194.

(60) Provisional application No. 60/648,822, filed on Feb. 1, 2005, provisional application No. 60/731,886, filed on Oct. 31, 2005.

(51) Int. Cl.
*A61M 5/19* (2006.01)
*A61M 5/31* (2006.01)
*A61M 5/32* (2006.01)

(52) U.S. Cl.
CPC .............. *A61M 5/2053* (2013.01); *A61M 5/24* (2013.01); *A61M 5/2448* (2013.01); *A61M 5/3129* (2013.01); *A61M 5/3204* (2013.01); *A61M 5/326* (2013.01); *A61M 2005/206* (2013.01); *A61M 2005/2013* (2013.01); *A61M 2005/2073* (2013.01); *A61M 2005/3128* (2013.01)

(56) References Cited

U.S. PATENT DOCUMENTS

| | | |
|---|---|---|
| 3,115,133 A | 12/1963 | Morando |
| 3,426,448 A | 2/1969 | Sarnoff |
| 3,563,373 A | 2/1971 | Paulson |
| 3,688,765 A | 9/1972 | Gasaway |
| 3,768,472 A | 10/1973 | Hodosh et al. |
| 3,795,061 A | 3/1974 | Sarnoff et al. |
| 3,941,130 A | 3/1976 | Tibbs |
| 3,945,379 A | 3/1976 | Pritz et al. |
| 4,031,889 A | 6/1977 | Pike |
| 4,086,062 A | 4/1978 | Hach |
| 4,108,177 A | 8/1978 | Pistor |
| 4,124,024 A | 11/1978 | Schwebel et al. |
| 4,226,235 A | 10/1980 | Sarnoff et al. |
| 4,258,713 A | 3/1981 | Wardlaw |
| 4,360,019 A | 11/1982 | Portner et al. |
| 4,394,863 A | 7/1983 | Bartner |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,755,169 A | 7/1988 | Sarnoff et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,822,340 A | 4/1989 | Kamstra |
| 4,826,489 A | 5/1989 | Haber |
| 4,853,521 A | 8/1989 | Claeys et al. |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,104,380 A | 4/1992 | Holman et al. |
| 5,125,898 A | 6/1992 | Kaufhold, Jr. et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,244,465 A | 9/1993 | Michel |
| 5,271,527 A | 12/1993 | Haber et al. |
| 5,281,198 A | 1/1994 | Haber et al. |
| 5,286,258 A | 2/1994 | Haber et al. |
| 5,295,965 A | 3/1994 | Wilmot |
| 5,298,023 A | 3/1994 | Haber et al. |
| 5,312,326 A | 5/1994 | Myers et al. |
| 5,314,412 A | 5/1994 | Rex |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,358,489 A | 10/1994 | Wyrick |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,399,163 A | 3/1995 | Peterson et al. |
| 5,417,660 A | 5/1995 | Martin |
| 5,451,210 A | 9/1995 | Kramer et al. |
| 5,466,217 A | 11/1995 | Myers et al. |
| 5,478,316 A | 12/1995 | Bitdinger et al. |
| 5,514,097 A | 5/1996 | Knauer |
| 5,514,135 A | 5/1996 | Earle |
| 5,527,287 A | 6/1996 | Miskinyar |
| 5,540,664 A | 7/1996 | Wyrick |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,658,259 A | 8/1997 | Pearson et al. |
| 5,681,291 A | 10/1997 | Galli |
| 5,681,292 A | 10/1997 | Tober et al. |
| 5,695,476 A | 12/1997 | Harris |
| 5,716,338 A | 2/1998 | Hjertman et al. |
| 5,728,074 A | 3/1998 | Castellano et al. |
| 5,772,635 A | 6/1998 | Dastur et al. |
| 5,779,677 A | 7/1998 | Frezza |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,570 A | 9/1998 | Fuchs et al. |
| 5,814,020 A | 9/1998 | Gross |
| 5,823,346 A | 10/1998 | Weiner |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,990 A | 12/1998 | Cirelli et al. |
| 5,852,590 A | 12/1998 | de la Huerga |

(56) References Cited

U.S. PATENT DOCUMENTS

| | | | |
|---|---|---|---|
| 5,853,292 | A | 12/1998 | Eggert et al. |
| 5,858,001 | A | 1/1999 | Tsals et al. |
| 5,865,795 | A | 2/1999 | Schiff et al. |
| 5,868,713 | A | 2/1999 | Klippenstein |
| 5,868,721 | A | 2/1999 | Marinacci |
| D407,487 | S | 3/1999 | Greubel et al. |
| 5,876,380 | A | 3/1999 | Manganini et al. |
| 5,925,021 | A | 7/1999 | Castellano et al. |
| 5,928,195 | A | 7/1999 | Malamud |
| 5,941,857 | A | 8/1999 | Nguyen et al. |
| 5,964,739 | A | 10/1999 | Champ |
| 5,971,953 | A | 10/1999 | Bachynsky |
| 6,015,438 | A | 1/2000 | Shaw |
| 6,030,363 | A | 2/2000 | Kriesel |
| 6,039,713 | A | 3/2000 | Botich et al. |
| 6,045,534 | A | 4/2000 | Jacobsen et al. |
| 6,050,977 | A | 4/2000 | Adams |
| 6,056,728 | A | 5/2000 | von Schuckmann |
| 6,062,901 | A | 5/2000 | Liu et al. |
| 6,063,053 | A | 5/2000 | Castellano et al. |
| 6,074,213 | A | 6/2000 | Hon |
| 6,077,106 | A | 6/2000 | Mish |
| 6,083,199 | A | 7/2000 | Thorley et al. |
| 6,084,526 | A | 7/2000 | Blotky et al. |
| 6,086,562 | A | 7/2000 | Jacobsen et al. |
| 6,096,002 | A | 8/2000 | Landau |
| 6,099,503 | A | 8/2000 | Stradella |
| 6,099,504 | A | 8/2000 | Gross et al. |
| 6,102,896 | A | 8/2000 | Roser |
| 6,119,684 | A | 9/2000 | Nöhl et al. |
| 6,149,626 | A | 11/2000 | Rachynsky et al. |
| 6,158,613 | A | 12/2000 | Novosel et al. |
| 6,161,281 | A | 12/2000 | Dando et al. |
| 6,165,155 | A | 12/2000 | Jacobsen et al. |
| 6,179,812 | B1 | 1/2001 | Botich et al. |
| 6,193,695 | B1 | 2/2001 | Rippstein, Jr. |
| 6,202,642 | B1 | 3/2001 | McKinnon et al. |
| 6,210,359 | B1 | 4/2001 | Patel et al. |
| 6,210,369 | B1 | 4/2001 | Wilmot et al. |
| 6,219,587 | B1 | 4/2001 | Ahlin et al. |
| 6,221,045 | B1 | 4/2001 | Duchon et al. |
| 6,221,055 | B1 | 4/2001 | Shaw et al. |
| 6,245,046 | B1 | 6/2001 | Sibbitt |
| 6,258,063 | B1 | 7/2001 | Haar et al. |
| 6,258,068 | B1 | 7/2001 | Kirchhofer et al. |
| 6,259,654 | B1 | 7/2001 | de la Huerga |
| 6,264,629 | B1 | 7/2001 | Landau |
| 6,270,479 | B1 | 8/2001 | Bergens et al. |
| 6,280,421 | B1 | 8/2001 | Kirchhofer et al. |
| 6,312,412 | B1 | 11/2001 | Saied et al. |
| 6,317,630 | B1 | 11/2001 | Gross et al. |
| 6,334,070 | B1 | 12/2001 | Nova et al. |
| 6,364,866 | B1 | 4/2002 | Furr et al. |
| 6,371,939 | B2 | 4/2002 | Bergens et al. |
| 6,383,168 | B1 | 5/2002 | Landau et al. |
| 6,387,078 | B1 | 5/2002 | Gillespie, III |
| 6,405,912 | B2 | 6/2002 | Giannou |
| 6,406,455 | B1 | 6/2002 | Willis et al. |
| 6,411,567 | B1 | 6/2002 | Niemiec et al. |
| 6,413,236 | B1 | 7/2002 | Van Dyke |
| 6,425,897 | B2 | 7/2002 | Overes et al. |
| 6,428,517 | B1 | 8/2002 | Hochman et al. |
| 6,428,528 | B2 | 8/2002 | Sadowski |
| 6,475,181 | B1 | 11/2002 | Potter et al. |
| 6,478,771 | B1 | 11/2002 | Lavi et al. |
| 6,482,186 | B1 | 11/2002 | Douglas et al. |
| 6,494,863 | B1 | 12/2002 | Shaw et al. |
| 6,500,150 | B1 | 12/2002 | Gross et al. |
| 6,514,230 | B1 | 2/2003 | Munk et al. |
| 6,529,446 | B1 | 3/2003 | de la Huerga |
| 6,530,900 | B1 | 3/2003 | Daily et al. |
| 6,530,904 | B1 | 3/2003 | Edwards et al. |
| 6,535,714 | B2 | 3/2003 | Melker et al. |
| 6,540,675 | B2 | 4/2003 | Aceti et al. |
| 6,544,234 | B1 | 4/2003 | Gabriel |
| 6,551,276 | B1 | 4/2003 | Mann et al. |
| 6,551,298 | B1 | 4/2003 | Zhang |
| 6,554,798 | B1 | 4/2003 | Mann et al. |
| 6,558,320 | B1 | 5/2003 | Causey, III et al. |
| 6,569,123 | B2 | 5/2003 | Alchas |
| 6,572,584 | B1 | 6/2003 | Shaw et al. |
| 6,574,166 | B2 | 6/2003 | Niemiec |
| 6,575,939 | B1 | 6/2003 | Brunel |
| RE38,189 | E | 7/2003 | Walker et al. |
| 6,585,685 | B2 | 7/2003 | Staylor et al. |
| 6,585,698 | B2 | 7/2003 | Packman et al. |
| 6,589,158 | B2 | 7/2003 | Winkler |
| 6,595,956 | B1 | 7/2003 | Gross et al. |
| 6,597,794 | B2 | 7/2003 | Cole et al. |
| 6,599,272 | B1 | 7/2003 | Hjertman et al. |
| 6,613,010 | B2 | 9/2003 | Castellano |
| 6,616,627 | B2 | 9/2003 | Willis et al. |
| 6,633,796 | B1 | 10/2003 | Pool et al. |
| 6,641,566 | B2 | 11/2003 | Douglas et al. |
| 6,645,171 | B1 | 11/2003 | Robinson et al. |
| 6,645,181 | B1 | 11/2003 | Lavi et al. |
| 6,648,850 | B2 | 11/2003 | Landau |
| 6,656,163 | B1 | 12/2003 | Marshall et al. |
| 6,673,035 | B1 | 1/2004 | Rice et al. |
| 6,676,630 | B2 | 1/2004 | Landau et al. |
| 6,689,093 | B2 | 2/2004 | Landau |
| 6,692,469 | B1 | 2/2004 | Weekes et al. |
| 6,702,778 | B2 | 3/2004 | Hill et al. |
| 6,706,019 | B1 | 3/2004 | Parker et al. |
| 6,707,763 | B2 | 3/2004 | Osberg et al. |
| 6,708,050 | B2 | 3/2004 | Carim |
| 6,722,916 | B2 | 4/2004 | Buccinna et al. |
| 6,723,077 | B2 | 4/2004 | Pickup et al. |
| 6,726,657 | B1 | 4/2004 | Dedig et al. |
| 6,726,661 | B2 | 4/2004 | Munk et al. |
| 6,736,796 | B2 | 5/2004 | Shekalim |
| 6,743,635 | B2 | 6/2004 | Neel et al. |
| 6,749,437 | B2 | 6/2004 | Chan |
| 6,752,781 | B2 | 6/2004 | Landau et al. |
| 6,764,469 | B2 | 7/2004 | Broselow |
| 6,767,336 | B1 | 7/2004 | Kaplan |
| 6,770,052 | B2 | 8/2004 | Hill et al. |
| 6,770,056 | B2 | 8/2004 | Price et al. |
| 6,783,509 | B1 | 8/2004 | Landau et al. |
| 6,786,875 | B2 | 9/2004 | Barker et al. |
| 6,793,646 | B1 | 9/2004 | Giambattista et al. |
| 6,803,856 | B1 | 10/2004 | Murphy et al. |
| 6,805,686 | B1 | 10/2004 | Fathallah et al. |
| 6,808,514 | B2 | 10/2004 | Schneider et al. |
| 6,809,653 | B1 | 10/2004 | Mann et al. |
| 6,817,986 | B2 | 11/2004 | Slate et al. |
| 6,830,560 | B1 | 12/2004 | Gross et al. |
| 6,839,304 | B2 | 1/2005 | Niemiec et al. |
| 6,872,200 | B2 | 3/2005 | Mann et al. |
| 6,875,195 | B2 | 4/2005 | Choi |
| 6,883,222 | B2 | 4/2005 | Landau |
| 6,923,764 | B2 | 8/2005 | Aceti et al. |
| 6,936,029 | B2 | 8/2005 | Mann et al. |
| 6,936,032 | B1 | 8/2005 | Bush, Jr. et al. |
| 6,937,150 | B2 | 8/2005 | Medema et al. |
| 6,942,646 | B2 | 9/2005 | Langley et al. |
| 6,946,299 | B2 | 9/2005 | Neel et al. |
| 6,948,492 | B2 | 9/2005 | Wermeling et al. |
| 6,949,082 | B2 | 9/2005 | Langley et al. |
| 6,952,604 | B2 | 10/2005 | DeNuzzio et al. |
| 6,953,445 | B2 | 10/2005 | Wilmot et al. |
| 6,953,693 | B2 | 10/2005 | Neel et al. |
| 6,958,691 | B1 | 10/2005 | Anderson et al. |
| 6,959,247 | B2 | 10/2005 | Neel et al. |
| 6,961,285 | B2 | 11/2005 | Niemiec et al. |
| 6,964,650 | B2 | 11/2005 | Alexandre et al. |
| 6,969,259 | B2 | 11/2005 | Pastrick et al. |
| 6,979,316 | B1 | 12/2005 | Rubin et al. |
| 6,979,326 | B2 | 12/2005 | Mann et al. |
| 6,985,870 | B2 | 1/2006 | Martucci et al. |
| 6,997,911 | B2 | 2/2006 | Klitmose |
| 7,014,470 | B2 | 3/2006 | Vann |
| 7,074,211 | B1 | 7/2006 | Heiniger et al. |
| 7,104,972 | B2 | 9/2006 | Moller et al. |

(56) References Cited

U.S. PATENT DOCUMENTS

| | | |
|---|---|---|
| 7,113,101 B2 | 9/2006 | Peterson et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,241,278 B2 | 7/2007 | Moller |
| 7,357,790 B2 | 4/2008 | Hommann et al. |
| 7,416,540 B2 | 8/2008 | Edwards et al. |
| 7,465,294 B1 | 12/2008 | Vladimirsky |
| 7,500,963 B2 | 3/2009 | Westbye et al. |
| 7,500,967 B2 | 3/2009 | Thorley et al. |
| 7,503,907 B1 | 3/2009 | Lesch, Jr. |
| 7,544,188 B2 | 6/2009 | Edwards et al. |
| 7,637,891 B2 | 12/2009 | Wall |
| 7,648,482 B2 | 1/2010 | Edwards et al. |
| 7,648,483 B2 | 1/2010 | Edwards et al. |
| 7,674,246 B2 | 3/2010 | Gillespie et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,758,550 B2 | 7/2010 | Bollenbach et al. |
| 7,806,866 B2 | 10/2010 | Hommann et al. |
| 7,850,662 B2 | 12/2010 | Veasey et al. |
| 7,901,377 B1 | 3/2011 | Harrison et al. |
| 7,918,823 B2 | 4/2011 | Edwards et al. |
| 7,918,832 B2 | 4/2011 | Veasey et al. |
| 7,931,614 B2 | 4/2011 | Gonnelli et al. |
| 7,938,802 B2 | 5/2011 | Bicknell et al. |
| 7,947,017 B2 | 5/2011 | Edwards et al. |
| 8,016,788 B2 | 9/2011 | Edwards et al. |
| 8,021,335 B2 | 9/2011 | Lesch, Jr. |
| 8,021,344 B2 | 9/2011 | Edwards et al. |
| 8,105,281 B2 | 1/2012 | Edwards et al. |
| 8,123,719 B2 | 2/2012 | Edwards et al. |
| 8,162,886 B2 | 4/2012 | Sadowski et al. |
| 8,172,082 B2 | 5/2012 | Edwards et al. |
| 8,206,360 B2 | 6/2012 | Edwards et al. |
| 8,221,347 B2 * | 7/2012 | Toles ............... G01F 11/026 604/70 |
| 8,226,610 B2 | 7/2012 | Edwards et al. |
| 8,231,573 B2 | 7/2012 | Edwards et al. |
| 8,313,466 B2 | 11/2012 | Edwards et al. |
| 8,361,029 B2 | 1/2013 | Edwards et al. |
| 8,425,462 B2 | 4/2013 | Edwards et al. |
| 8,608,698 B2 | 12/2013 | Edwards et al. |
| 8,622,973 B2 | 1/2014 | Edwards et al. |
| 8,690,827 B2 | 4/2014 | Edwards et al. |
| 8,734,392 B2 | 5/2014 | Stadelhofer |
| 8,747,357 B2 | 6/2014 | Stamp et al. |
| 8,920,367 B2 | 12/2014 | Edwards et al. |
| 8,920,377 B2 | 12/2014 | Edwards et al. |
| 9,022,980 B2 | 5/2015 | Edwards et al. |
| 9,056,170 B2 | 6/2015 | Edwards et al. |
| 9,084,849 B2 | 7/2015 | Edwards et al. |
| 9,149,579 B2 | 10/2015 | Edwards et al. |
| 9,173,999 B2 | 11/2015 | Edwards et al. |
| 2001/0005781 A1 | 6/2001 | Bergens et al. |
| 2001/0037087 A1 | 11/2001 | Knauer |
| 2002/0055711 A1 | 5/2002 | Lavi et al. |
| 2002/0074345 A1 | 6/2002 | Schneider et al. |
| 2002/0076679 A1 | 6/2002 | Aman |
| 2002/0095120 A1 | 7/2002 | Larsen et al. |
| 2003/0028145 A1 | 2/2003 | Duchon et al. |
| 2003/0040717 A1 | 2/2003 | Saulenas et al. |
| 2003/0105430 A1 | 6/2003 | Lavi et al. |
| 2003/0106824 A1 | 6/2003 | Wilmot et al. |
| 2003/0120222 A1 | 6/2003 | Vaillancourt |
| 2003/0132128 A1 | 7/2003 | Mazur |
| 2003/0135388 A1 | 7/2003 | Martucci et al. |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0024361 A1 | 2/2004 | Fago et al. |
| 2004/0024367 A1 | 2/2004 | Gilbert |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0073169 A1 | 4/2004 | Amisar et al. |
| 2004/0092874 A1 | 5/2004 | Mazidji |
| 2004/0094146 A1 | 5/2004 | Schiewe et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0049561 A1 | 3/2005 | Hommann et al. |
| 2005/0062603 A1 | 3/2005 | Fuerst et al. |
| 2005/0090781 A1 | 4/2005 | Baba et al. |
| 2005/0090782 A1 | 4/2005 | Marshall et al. |
| 2005/0101912 A1 | 5/2005 | Faust et al. |
| 2005/0134433 A1 | 6/2005 | Sweeney, II |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0192530 A1 | 9/2005 | Castellano |
| 2005/0197654 A1 | 9/2005 | Edman et al. |
| 2005/0203466 A1 | 9/2005 | Hommann et al. |
| 2005/0222539 A1 | 10/2005 | Gonzales et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0069350 A1 | 3/2006 | Buenger et al. |
| 2006/0074519 A1 | 4/2006 | Barker et al. |
| 2006/0111666 A1 | 5/2006 | Hommann et al. |
| 2006/0111671 A1 | 5/2006 | Klippenstein |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0204939 A1 | 9/2006 | Bardsley et al. |
| 2006/0235354 A1 | 10/2006 | Kaal et al. |
| 2006/0247578 A1 | 11/2006 | Arguendas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0100288 A1 | 5/2007 | Bozeman et al. |
| 2007/0129686 A1 | 6/2007 | Daily et al. |
| 2007/0135767 A1 | 6/2007 | Gillespie, III et al. |
| 2007/0184847 A1 | 8/2007 | Hansen et al. |
| 2007/0210147 A1 | 9/2007 | Morrone et al. |
| 2007/0213598 A1 | 9/2007 | Howard et al. |
| 2007/0265568 A1 | 11/2007 | Tsals et al. |
| 2008/0147006 A1 | 6/2008 | Brunnberg et al. |
| 2008/0154200 A1 | 6/2008 | Lesch |
| 2008/0171995 A1 | 7/2008 | Vitullo et al. |
| 2008/0188798 A1 | 8/2008 | Weber |
| 2008/0228143 A1 | 9/2008 | Stamp |
| 2008/0255513 A1 | 10/2008 | Kaal et al. |
| 2008/0262443 A1 | 10/2008 | Hommann et al. |
| 2009/0093759 A1 | 4/2009 | Judd et al. |
| 2009/0192486 A1 | 7/2009 | Wilmot et al. |
| 2009/0221962 A1 | 9/2009 | Kaal et al. |
| 2009/0240200 A1 | 9/2009 | Heneveld et al. |
| 2009/0318361 A1 | 12/2009 | Noera et al. |
| 2010/0010454 A1 | 1/2010 | Marshall et al. |
| 2010/0049125 A1 | 2/2010 | James et al. |
| 2010/0152659 A1 | 6/2010 | Streit et al. |
| 2010/0160894 A1 | 6/2010 | Julian et al. |
| 2010/0185148 A1 | 7/2010 | Gillespie, III et al. |
| 2010/0211005 A1 | 8/2010 | Edwards et al. |
| 2010/0212663 A1 | 8/2010 | Vedrine et al. |

(56) References Cited

U.S. PATENT DOCUMENTS

| | | |
|---|---|---|
| 2011/0060274 A1 | 3/2011 | Kuhn |
| 2011/0077589 A1 | 3/2011 | Karlsson et al. |
| 2011/0201999 A1 | 8/2011 | Cronenberg |
| 2011/0295215 A1 | 12/2011 | Nielsen et al. |
| 2012/0079718 A1 | 4/2012 | Singer et al. |
| 2012/0107783 A1 | 5/2012 | Julian et al. |
| 2012/0289929 A1 | 11/2012 | Boyd et al. |
| 2012/0302966 A1 | 11/2012 | Vedrine et al. |
| 2013/0317477 A1 | 11/2013 | Edwards et al. |
| 2015/0238695 A1 | 8/2015 | Edwards et al. |
| 2016/0015907 A1 | 1/2016 | Edwards et al. |
| 2016/0045670 A1 | 2/2016 | Edwards et al. |
| 2016/0184521 A1 | 6/2016 | Edwards et al. |
| 2016/0250414 A1 | 9/2016 | Edwards et al. |

FOREIGN PATENT DOCUMENTS

| | | |
|---|---|---|
| EP | 1712178 A2 | 10/2006 |
| FR | 1514210 | 2/1968 |
| FR | 2506161 | 11/1982 |
| FR | 2509615 | 1/1983 |
| FR | 2700959 | 2/1993 |
| MX | PA04009276 | 1/2005 |
| WO | WO 91/04760 | 4/1991 |
| WO | WO 95/13838 | 5/1995 |
| WO | WO 95/26009 | 9/1995 |
| WO | WO 95/35126 | 12/1995 |
| WO | WO 98/52632 | 11/1998 |
| WO | WO 99/10031 | 3/1999 |
| WO | WO 2001/024690 | 4/2001 |
| WO | WO 2001/026020 | 4/2001 |
| WO | WO 2001/088828 | 11/2001 |
| WO | WO 2001/093926 | 12/2001 |
| WO | WO 2002/083205 | 10/2002 |
| WO | WO 2002/083212 | 10/2002 |
| WO | WO 2003/011378 | 2/2003 |
| WO | WO 2003/013632 | 2/2003 |
| WO | WO 2003/095001 | 11/2003 |
| WO | WO 2003/097133 | 11/2003 |
| WO | WO 2004/047890 | 6/2004 |
| WO | WO 2004/047891 | 6/2004 |
| WO | WO 2004/047892 | 6/2004 |
| WO | WO 2004/047893 | 6/2004 |
| WO | WO 2004/054644 | 7/2004 |
| WO | WO 2005/050526 | 6/2005 |
| WO | WO 2005/070481 | 8/2005 |
| WO | WO 2005/077441 | 8/2005 |
| WO | WO 2006/058426 | 6/2006 |
| WO | WO 2006/109778 | 10/2006 |
| WO | WO 2007/083115 | 7/2007 |
| WO | WO 2008/005315 | 1/2008 |
| WO | WO 2008/148864 | 12/2008 |
| WO | WO 2010/033806 | 3/2010 |
| WO | WO 2013/044172 | 3/2013 |

OTHER PUBLICATIONS

"Solutions for Medical Devices," 3M Brochure, © 3M, (2006), 80-6201-3490-0, 8 pages.
Tingelstad, M., "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID=CA6332947>, 3 pages.
"Flexible circuits / Flex circuits / Flexible Technology Ltd.," Flexible Technology Limited [online] [retrieved on Aug. 28, 2006] Retrieved from the Internet <URL: http://www.flexibletechnology.com/ >, 2 pages.
"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >, 2 pages.
"Flex Circuits/flexible circuits design guide," [online] [retrieved on Aug. 28, 2006] Retrieved from the Internet <URL: http://flexiblecircuit.co.uk/Flex Circuits Design Guide.htm >, 7 pages.
"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >, 3 pages.
"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >, 3 pages.
Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>, 3 pages.
RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.
"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.
Scholz, O., "Drug depot in a tooth," [online] [retrieved on Feb. 6, 2007] Retrieved from the Internet <URL: http://www.fraunhoferde/fhg/EN/press/pi/2007/02Mediendienst22007Thema2.jsp?print=true>, 1 page.
Heartsine Technology, samaritan™ Pad Accessories [online] [retrieved on Jun. 1, 2007] Retrieved from the Internet <URL: http://www.heartsine.com/aboutsam-accessories.htm>, 4 pages.
CliniSense Corporation, "Drug delivery devices a potentially harsh environment for drugs," Stability [online] [retrieved on Jun. 1, 2007] Retrieved from the Internet <URL: http://www.clinisense.com/devices.htm>, 2 pages.
CliniSense Corporation, "LifeTrack Technology A new method to detect improper storage." Stability [online] [retrieved on Jun. 1, 2007] Retrieved from the Internet <URL: http://www.clinisense.com/tech.htm>, 2 pages.
AED Professionals™ Brochure [online] [retrieved on Jun. 1, 2007] Retrieved from the Internet <URL: http://www.aedprofessionals.com>, 4 pages.
Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >, 8 pages.
Office Action for Canadian Patent Application No. 2,586,525, dated Aug. 17, 2010.
Examination Report for British Patent Application No. GB 0708523.6, dated Dec. 8, 2008.
Examination Report for British Patent Application No. GB 0822532.8, dated Jan. 21, 2009.
Examination Report for British Patent Application No. GB 0822532.8, dated May 21, 2009.
Office Action for U.S. Appl. No. 11/562,061, dated Feb. 3, 2009.
Office Action for U.S. Appl. No. 11/566,422, dated Jul. 6, 2010.
Office Action for U.S. Appl. No. 11/566,422, dated Dec. 3, 2010.
Office Action for Japanese Patent Application No. 2009-537380, dated Jun. 15, 2012.
Office Action for U.S. Appl. No. 11/758,393, dated May 13, 2009.
Search Report and Written Opinion for International Patent Application No. PCT/US07/84891 dated Sep. 15, 2008, 7 pages.
Office Action for U.S. Appl. No. 12/138,987, dated Oct. 5, 2009.
Office Action for U.S. Appl. No. 13/053,451, dated Nov. 15, 2012.
Office Action for U.S. Appl. No. 13/090,392, dated Feb. 29, 2012.
International Search Report and Written Opinion for International Patent Application No. PCT/US06/03415, dated Jul. 13, 2006, 10 pages.

(56) References Cited

OTHER PUBLICATIONS

International Search Report and Written Opinion for International Patent Application No. PCT/US07/007626, dated Sep. 29, 2008.
Office Action for India Patent Application No. 3988/DELP/2009, dated Mar. 31, 2017.

* cited by examiner

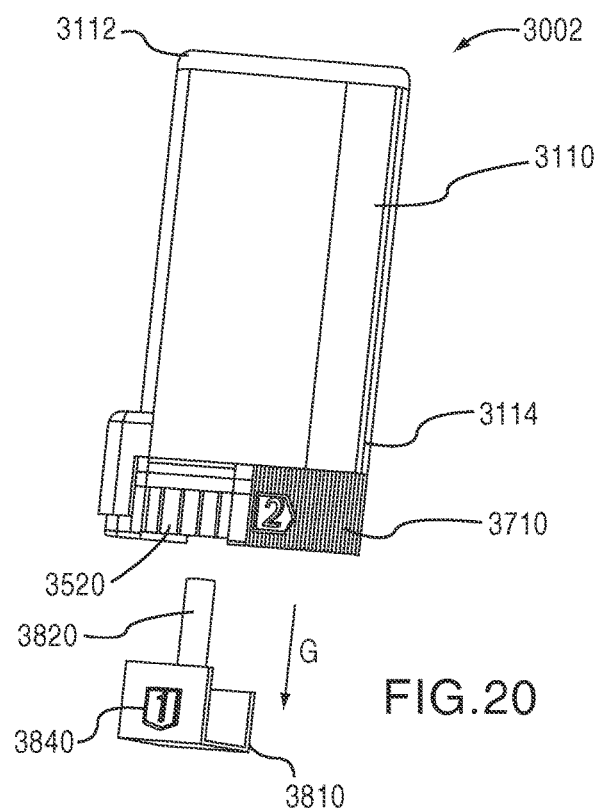
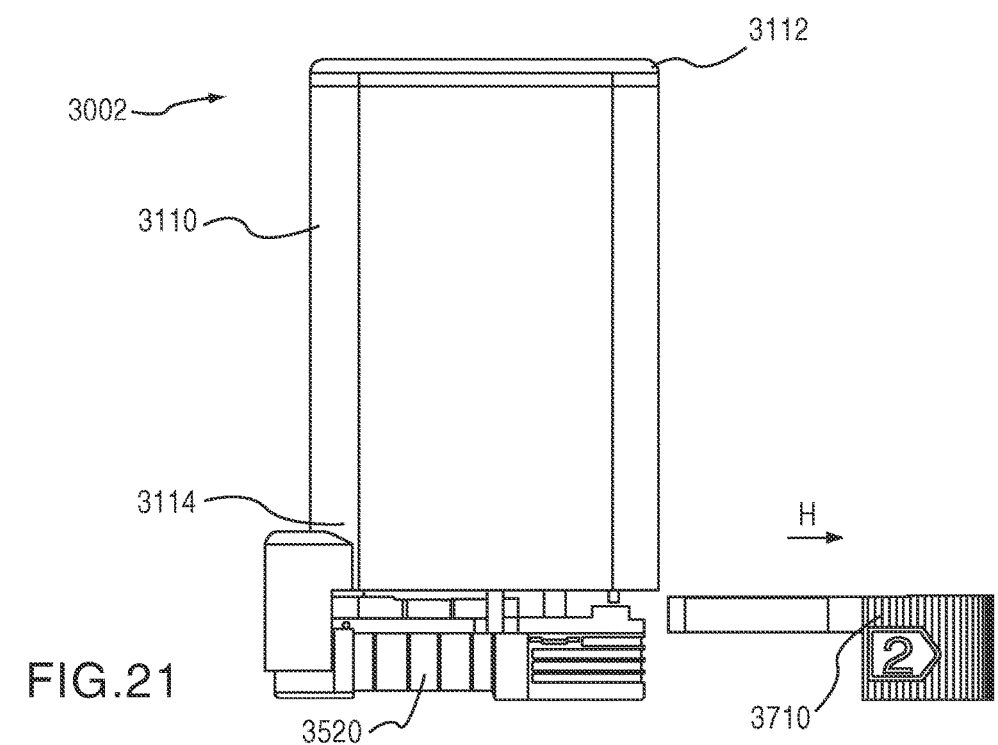

DEVICES, SYSTEMS AND METHODS FOR MEDICAMENT DELIVERY

CROSS-REFERENCE TO RELATED APPLICATIONS

This application is a continuation of U.S. patent application Ser. No. 13/748,728, filed Jan. 24, 2013, which is a continuation of U.S. patent application Ser. No. 13/090,392, now U.S. Pat. No. 8,361,029, filed Apr. 20, 2011, which is a continuation of U.S. patent application Ser. No. 11/566,422, entitled "Devices, Systems and Methods for Medicament Delivery," now U.S. Pat. No. 7,947,017, filed Dec. 4, 2006, which is a continuation-in-part of U.S. patent application Ser. No. 10/515,571, entitled "Devices, Systems and Methods for Medicament Delivery," filed Nov. 23, 2004, now U.S. Pat. No. 7,416,540, which is a national stage filing under 35 U.S.C. §371 of International Patent Application No. PCT/US2004/039386, entitled "Devices, Systems and Methods for Medicament Delivery," filed Nov. 23, 2004, each of which is incorporated herein by reference in its entirety. U.S. patent application Ser. No. 11/566,422, filed Dec. 4, 2006, is also a continuation-in-part of U.S. patent application Ser. No. 10/572,148, entitled "Devices, Systems and Methods for Medicament Delivery," filed Mar. 16, 2006 (now U.S. Pat. No. 7,749,194, issued Jul. 6, 2010), which is a national stage filing under 35 U.S.C. §371 of International Patent Application No. PCT/US2006/003415, entitled "Devices, Systems and Methods for Medicament Delivery," filed Feb. 1, 2006, which claims priority to U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005. Each of the above referenced applications is incorporated herein by reference in its entirety.

BACKGROUND

The invention relates generally to a medical device, and more particularly to an auto-injector for injecting a medicament into a body of a patient.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure.

Because emergency medical facilities may not be available when an individual is suffering from an allergic reaction, some individuals carry an auto-injector to rapidly self-administer a medicament in response to an allergic reaction. Some known auto-injectors are cylindrical in shape and include a spring loaded needle to automatically penetrate the user's skin and inject the medicament. Such known auto-injectors can be bulky and conspicuous, which can make carrying them inconvenient and undesirable. Moreover, some known auto-injectors do not have a retractable needle and, as such, cause a sharps hazard when injection is complete.

Some known auto-injectors use pressurized gas to insert a needle and/or inject a medicament into the patient. Such known auto-injectors often do not include a mechanism for completely releasing or venting the pressurized gas upon completion of the injection event.

Thus, a need exists for an auto-injector that can be more conveniently carried by a user and does not present a sharps hazard upon completion of the injection. Furthermore, a need exists for a gas-powered auto-injector that has an improved gas release mechanism.

SUMMARY

Apparatuses and methods for automatic medicament injection are described herein. In one embodiment, an apparatus includes a movable member and a valve coupled to the movable member. The movable member is configured to be disposed within a housing of a medical device and has a first end portion and second end portion. A portion of the first end portion is configured to define a portion of a boundary of a gas chamber. The first end portion defines an opening configured to be in fluid communication between the gas chamber and an area outside the gas chamber. The second end portion is configured to be coupled to a needle configured to deliver a medicament into a body. The valve is configured to selectively allow fluid communication between the gas chamber and the area outside the gas chamber through the opening defined by the first end portion of the movable member.

BRIEF DESCRIPTION OF THE DRAWINGS

FIG. 20 is a perspective view of the auto-injector illustrated in FIG. 17 showing an assembly according to an embodiment of the invention being removed.

FIG. 21 is a front view of the auto-injector illustrated in FIG. 17 showing a member according to an embodiment of the invention being removed.

DETAILED DESCRIPTION

Figure 1:
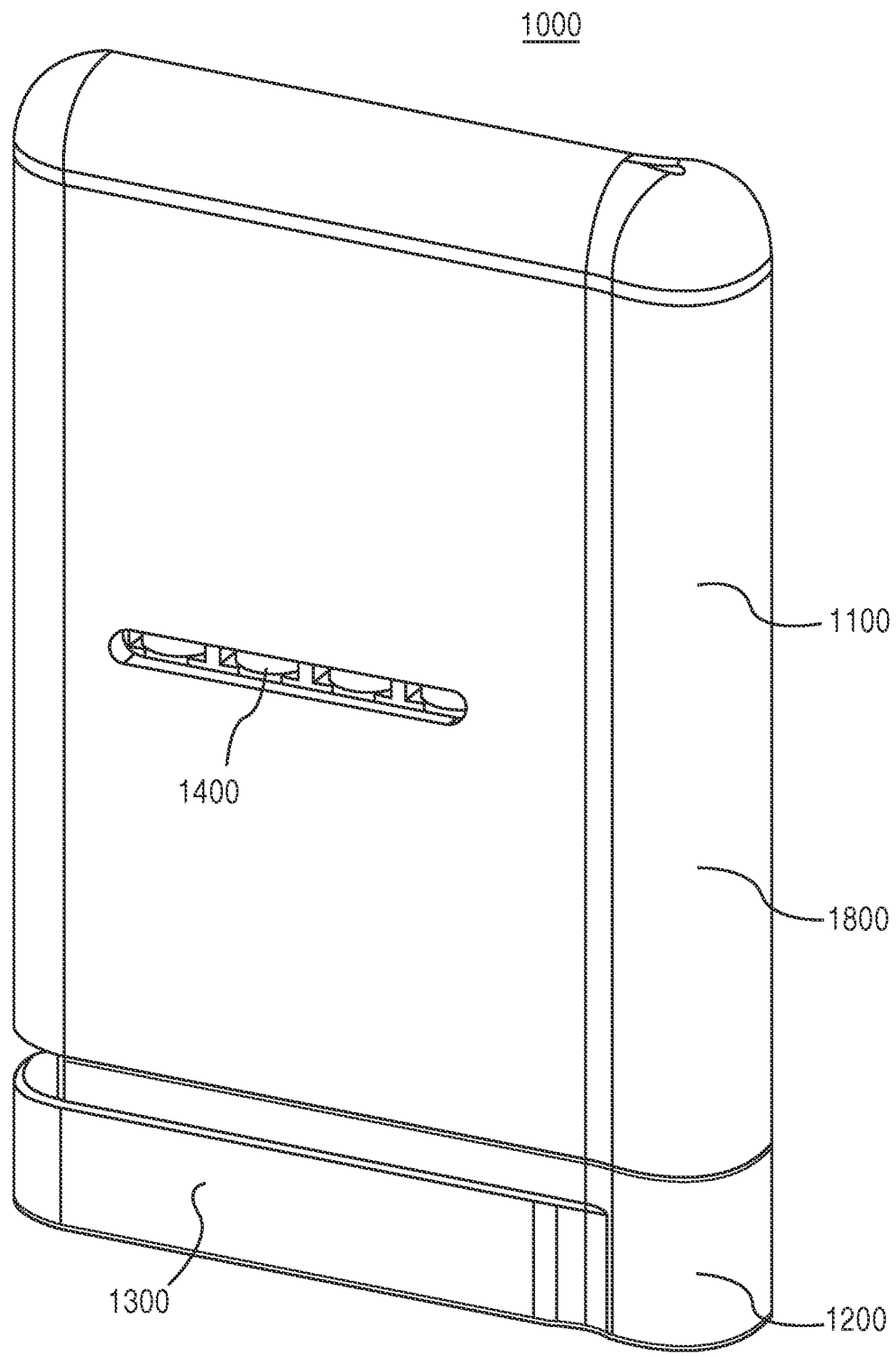
FIG. 1 is a perspective view of a system according to an embodiment of the invention.

Apparatuses and methods for automatic medicament injection are described herein. In some embodiments, an apparatus includes a movable member and a valve coupled to the movable member. The movable member is configured to be disposed within a housing of a medical device and has a first end portion and second end portion. A portion of the first end portion is configured to define a portion of a boundary of a gas chamber. The first end portion defines an opening configured to be in fluid communication between the gas chamber and an area outside the gas chamber. The second end portion is configured to be coupled to a needle configured to deliver a medicament into a body. The valve is configured to selectively allow fluid communication between the gas chamber and the area outside the gas chamber through the opening defined by the first end portion of the movable member.

In some embodiments, an apparatus includes a movable member, a valve and an actuator. The valve and the actuator are each coupled to the movable member. The movable member is configured to be disposed within a housing of a medical device and has a first end portion and second end portion. A portion of the first end portion is configured to define a portion of a boundary of a gas chamber. The first end portion defines an opening configured to be in fluid communication between the gas chamber and an area outside the gas chamber. The second end portion is configured to be coupled to a needle configured to deliver a medicament into a body. The valve is configured to selectively allow fluid communication between the gas chamber and the area outside the gas chamber through the opening defined by the first end portion of the movable member. The actuator is configured to move the valve between a first position and a second position. When the valve is in the first position the gas chamber is fluidically isolated from the area outside the gas chamber. When the valve is in the second position the gas chamber is in fluid communication with the area outside the gas chamber.

In some embodiments, an apparatus includes a housing, a medicament container, a medicament injector, an injection member and a valve. The housing defines a gas chamber. The medicament container is configured to be movably disposed within the housing and defines a portion of a boundary of the gas chamber. The medicament injector includes a seal configured to engage a portion of the housing to fluidically isolate the gas chamber from an area outside the gas chamber. A portion of the medicament injector is engaged with a medicament container that is movably disposed within the housing. The injection member, which can be, for example, a needle, defines a lumen configured to be in fluid communication with the medicament container and is configured to convey a medicament from the medicament container into a body of a patient. The medicament injector has a first position and a second position. When in the first position, the injection member is contained within the housing. When in the second position, a portion of the injection member extends from the housing. The valve, which can be disposed on the medicament injector, has a first configuration and a second configuration. When the valve is in the first configuration, the gas chamber is fluidically isolated from the area outside the gas chamber. When the valve is in the second configuration, the gas chamber is in fluid communication with the area outside the gas chamber.

In some embodiments, an apparatus includes a housing defining a gas chamber, a movable member and a gas release assembly. The movable member has a first portion and a second portion. The first portion defines a portion of a boundary of the gas chamber. The second portion is configured to be coupled to a needle that can deliver a medicament into a body. The movable member is disposable within the housing in a first position and a second position. When the movable member is in the first position, the needle is disposed within the housing. When the movable member is in the second position, a portion of the needle extends outside the housing. The gas release assembly, which can include, for example, a valve, an actuator and a passageway between the gas chamber and an area outside of the gas chamber, has a first configuration and a second configuration. When the gas release system is in its first configuration, the gas chamber is fluidically isolated from the area outside the gas chamber. When the gas release system is in its second configuration, the gas chamber is in fluid communication with the area outside the gas chamber. The gas release assembly is configured to be moved from its first configuration to its second configuration when the movable member is in its second position. The gas release system is further configured to be maintained in its second configuration independent of the position of the movable member.

In some embodiments, an apparatus includes a housing defining a gas chamber, a movable member and a valve. The movable member is configured to move longitudinally within the housing. The movable member has a first portion and a second portion. The first portion defines a portion of a boundary of the gas chamber. The second portion is configured to move a plunger within a medicament container to expel a medicament contained within the medicament container. The valve defines a flow passageway between the gas chamber and an area outside the gas chamber. The flow passageway has a flow area that varies as a function of a longitudinal position of the movable member.

Figure 2:
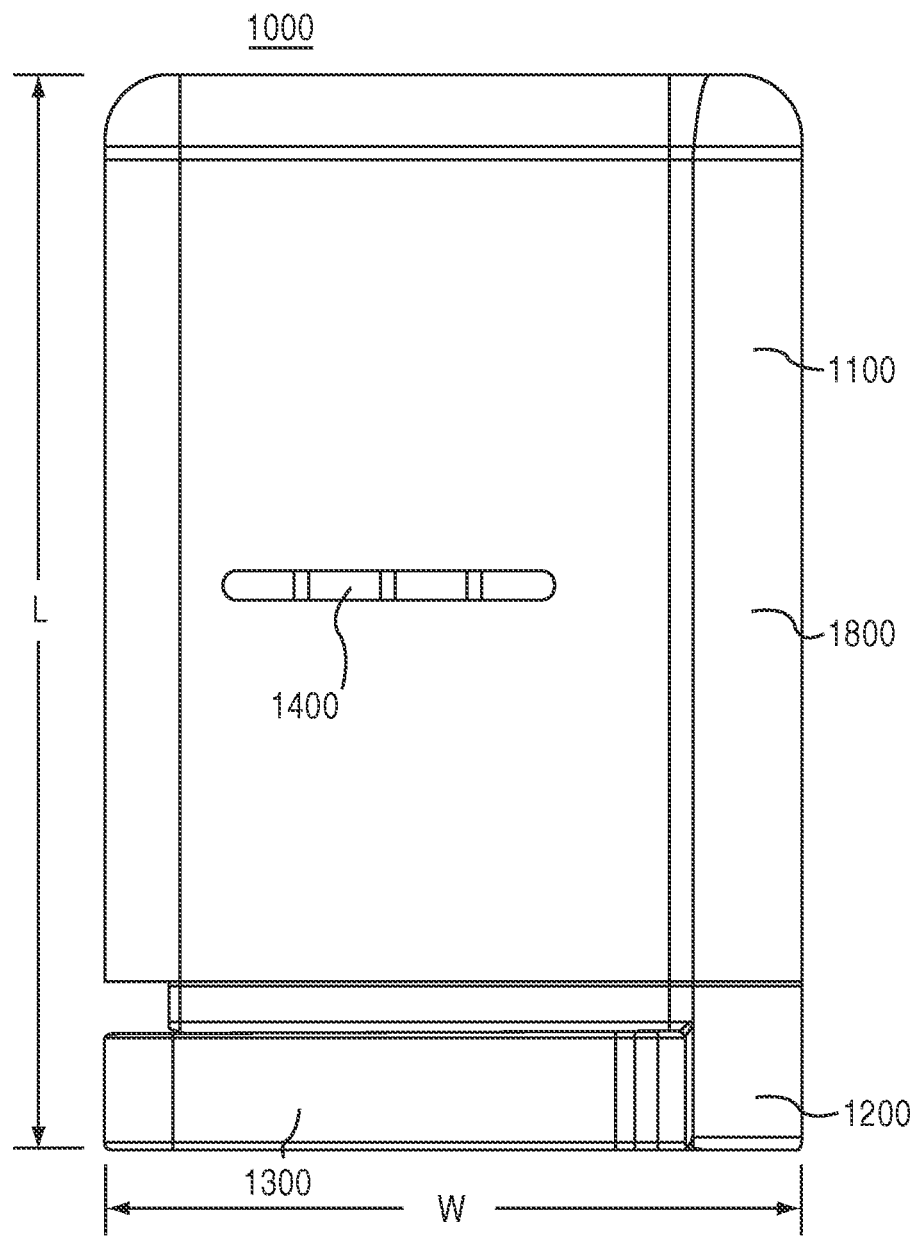
FIG. 2 is a front view of a system according to an embodiment of the invention.
Figure 3:
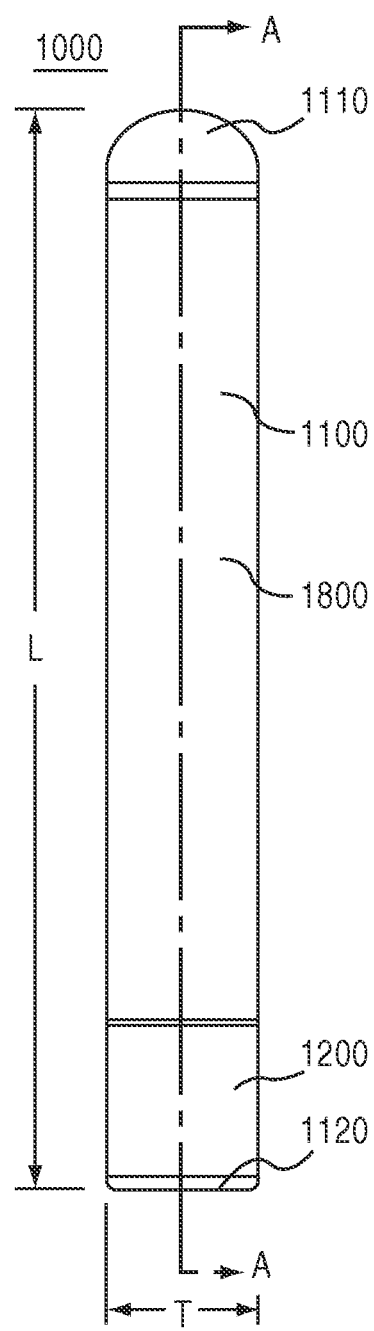
FIG. 3 is a side view of a system according to an embodiment of the invention.

FIG. 1 is a perspective view, FIG. 2 is a front view, and FIG. 3 is a side view, of a system 1000 according to the invention, which can comprise a housing 1100, which, in some embodiments, can comprise a handheld portion 1800 separated via an actuation guard 1200 from an actuation bar 1300. Actuation guard 1200 can prevent accidental activation of system 1000. Housing 1100 can be constructed of a durable material, such as stainless steel, aluminum, polycarbonate, etc., to protect a compressed gas container, medicament, injection apparatus and/or user of system 1000. The injection apparatus can be actuated by a fluid pressure, such as pressure provided by the compressed gas, which upon completion of actuation can escape housing 1100 via gas escape opening, such as via status indicator 1400.

A status of a system 1000 can be determined via status indicator 1400, which can provide a view, such as via a UV blocking, photo-sensitive, and/or translucent window, into an interior of housing 1100. Viewable through the window can be a status of medicament carried by housing 1100, a location of a needle and/or injection apparatus for the medicament, and/or an activation status of system 1000. For example, if the medicament has aged to the point of discoloration, which aging might or might not render the medication useless, harmful, etc., status indicator 1400 can allow that situation to be determined. In some embodiments, gas can escape housing 1100 via status indicator 1400 and/or another opening in housing 1100.

Some embodiments of system 1000 can provide a compact medicament delivery mechanism that can efficiently and/or rapidly deliver a prescribed dose. The length (L) and width (W) of system 1000 can be similar to that of a credit card, and the thickness (T) can be less than one inch. Thus, some embodiments of system 1000 can provide a conveniently carried, easy-to-use, easy to activate drug delivery apparatus that can require little to no training to safely carry, use, and/or dispose of.

To assist a user in positioning system 1000 in a correct orientation for injection, system 1000 and/or housing 1100 can provide various tactile clues. For example, a top 1110 of housing 1100 can be rounded, and a bottom 1120 of actuation bar 1300 of housing 1100 can be flat. Other tactile clues are also possible, such as bulges, ribs, grooves, gaps, roughened surfaces, indentations, etc.

Figure 4:
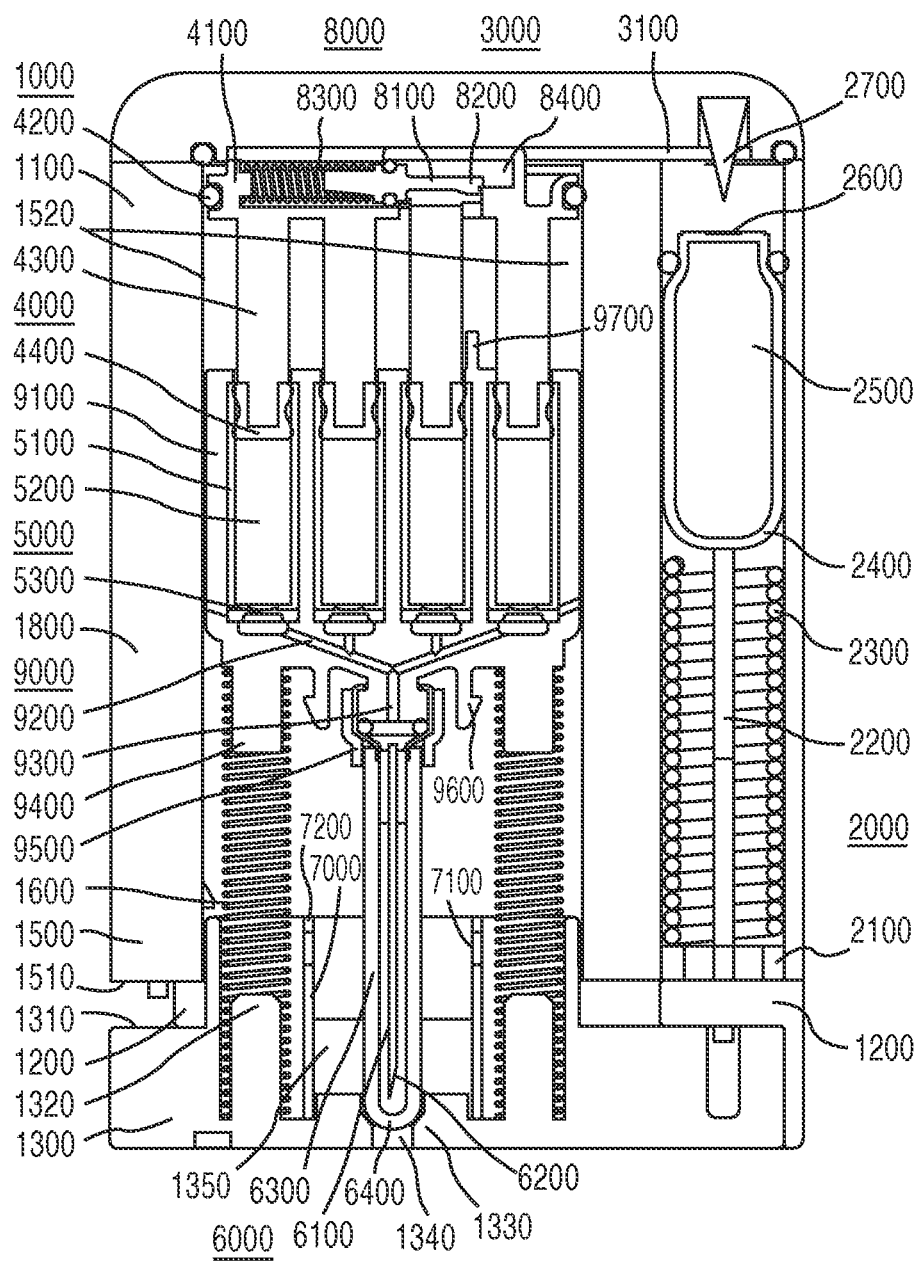
FIG. 4 is a cross-sectional view taken along line A-A of FIG. 3 of a system according to an embodiment of the invention in a first operative position.

FIG. 4 is a cross-sectional view taken along line A-A of FIG. 3 of an embodiment of a system 1000 in a first operative position. FIGS. 5, 6, 7, 8, and 9 show system 1000 of FIG. 4 in second, third, fourth, fifth, and sixth operative positions, respectively.

System 1000 can comprise a housing 1100, handheld portion 1800, actuation guard 1200, and/or actuation bar 1300. System 1000 can comprise system actuator 2000, gas reservoirs 3000, medicament actuator 4000, medicament storage assembly 5000, medicament carrier 9000, needle assembly 6000, use indicator 7000, and/or gas vent mechanism 8000, etc.

Upon removal, release, rotation, and/or relocation of actuation guard 1200, system actuator 2000 can be adapted to rapidly discharge an actuating portion of a contents of a compress gas container. For example, system actuator 2000 can comprise a compressed gas container 2400, which initially can contain a compressed gas 2500, an actuating portion of which can be released from container 2400 by penetration of a gas port 2600 via a point of a puncturer 2700. Upon removal and/or relocation of actuation guard 1200, actuation bar 1300 can be moved closer to and/or in contact with handheld portion 1800. Upon removal and/or relocation of actuation guard 1200, gas container 2400 can be brought into contact with puncturer 2700 via extension of a pre-compressed spring 2300 and/or movement of an actuation stick 2200. Thus, actuation guard 1200 can prevent accidental activation of system 1000 and/or unintended discharge of an actuating portion of the contents 2500 of gas container 2400.

Once gas port 2600 has been punctured, an actuating portion of compressed gas 2500 can escape from container 2400 and flow via gas reservoirs 3000, such as gas channel 3100. The flowing gas can meet and/or apply gas pressure to medicament actuator 4000, which can comprise a pusher

4100, which can travel within a sleeve 1500 defined by walls 1520. Sleeve 1500 can be constructed of metal, stainless steel, aluminum, plastic, polycarbonate, etc. Seals 4200, such as o-rings, can resist gas leakage, such as past pusher 4100 and/or out of housing 1100. Thus, pusher 4100 can function as a piston traveling within a cylinder, although it is not necessarily required that the cross-sectional shape of sleeve 1500 be round.

Medicament actuator 4000 can interface with medicament storage assembly 5000. For example, medicament actuator 4000 can comprise a plurality of plungers 4300, each of which can be capped with a piston 4400 which can sealingly slide and/or move within a corresponding vial 5100 containing a liquid medicament 5200. For example, in response to pressure applied by an actuating portion of the contents 2500 of compressed gas container 2400, pusher 4100 can cause plungers 4300 and/or pistons 4400 to simultaneously move. The number of corresponding sets of plungers 4300, pistons 4400, and/or vials 5100 can be 2, 3, 4, 5, 6, or more. Pistons 4400 can be constructed of a resilient, durable, and/or sealing material, such as a rubber. Each plunger 4300 from the plurality of plungers can define a longitudinal axis, the longitudinal axes (e.g., axes 4310, 4320, 4330, 4340) of the plurality of plungers can be parallel, non-coaxial, and/or co-planar.

Each vial 5100 from the plurality of vials can be substantially cylindrical with a substantially round and/or substantially elliptical cross-sectional shape. Thus, each vial 5100 can define a longitudinal axis, the longitudinal axes of the plurality of vials can be parallel, non-coaxial, and/or co-planar. The longitudinal axis of each vial can be co-axial with the longitudinal axis of its corresponding plunger.

Each vial can be capped at one end with a frangible seal 5300, which can be burst when piston 4400 generates sufficient pressure upon medicament 5200, thereby allowing at least a portion of medicament 5200 to flow out of vial 5100 and into medicament carrier 9000. Thus, the plurality of vials can be fluidly coupleable to the actuating portion of the contents 2500 of gas container 2400.

Medicament carrier 9000 can hold each of vials 5100 and can travel within sleeve 1500. Medicament carrier 9000 can comprise a plurality of channels 9200 adapted to receive medicament 5200 as it exits its respective vial 5100, and direct medicament 5200 to a common conduit 9300. Medicament carrier 9000 can interface with needle assembly 6000 and/or use indicator 7000.

From common conduit 9300, medicament 5200 can enter needle assembly 6000, such as into a single needle 6100 via which medicament can approach needle tip 6200. As medicament actuator 4000 and/or medicament carrier 9000 are driven toward actuator bar 1300, needle tip 6200 can penetrate an end 6400 of needle sheath 6300 and exit actuator bar 1300 at needle port 1340.

Figure 5:
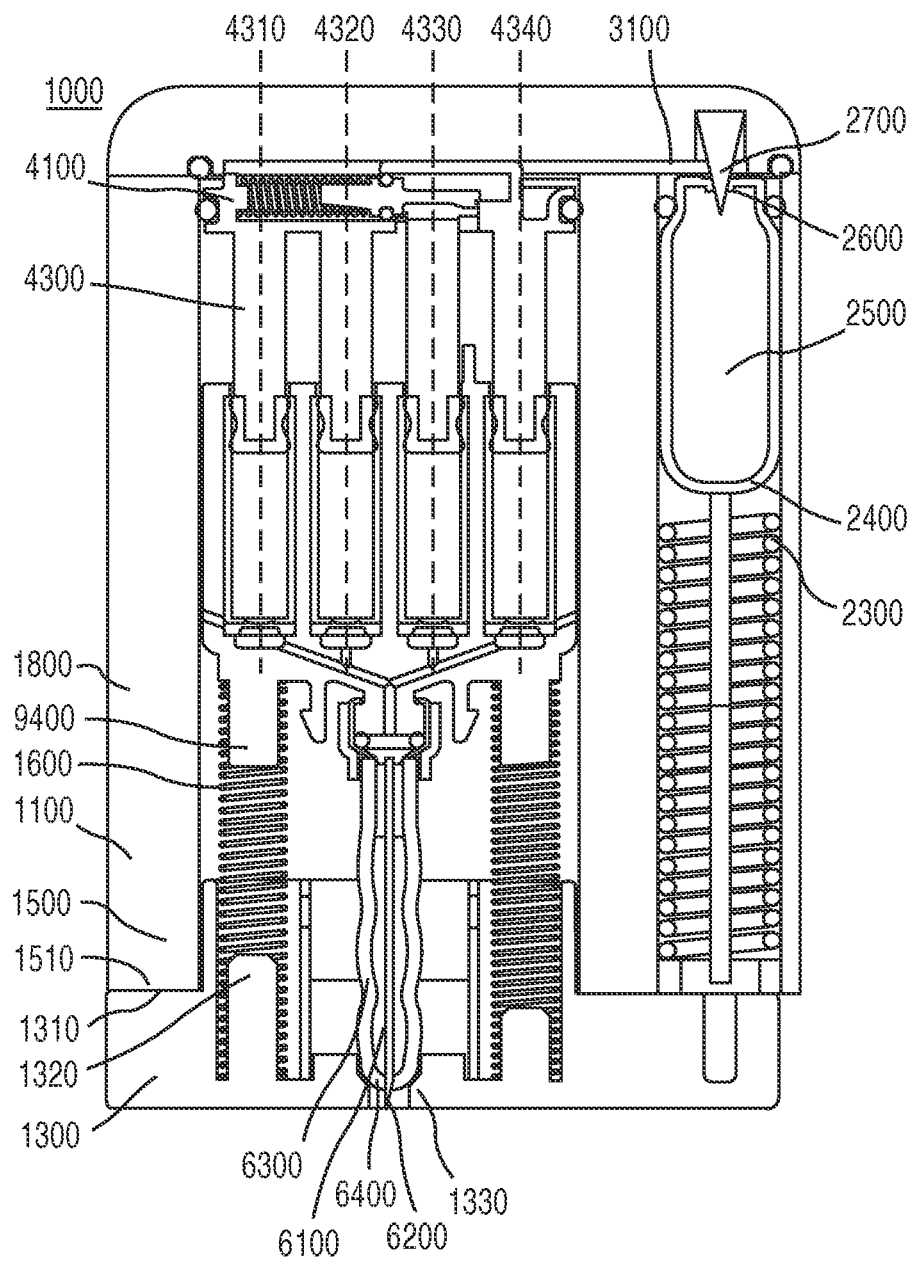
FIG. 5 is a cross-sectional view taken along line A-A of FIG. 3 of a system according to an embodiment of the invention in a second operative position.

Referring to FIG. 5, upon movement of actuation bar 1300 closer to handheld portion 1800, sheath seat 1330 can come in contact with sheath tip 6400, thereby causing sheath 6300 to buckle and/or crumble. As actuator bar 1300 comes in contact with handheld portion 1800, bar stop 1320 can approach medicament carrier stop 9400, while carrier spring 1600 is compressed.

Figure 6:
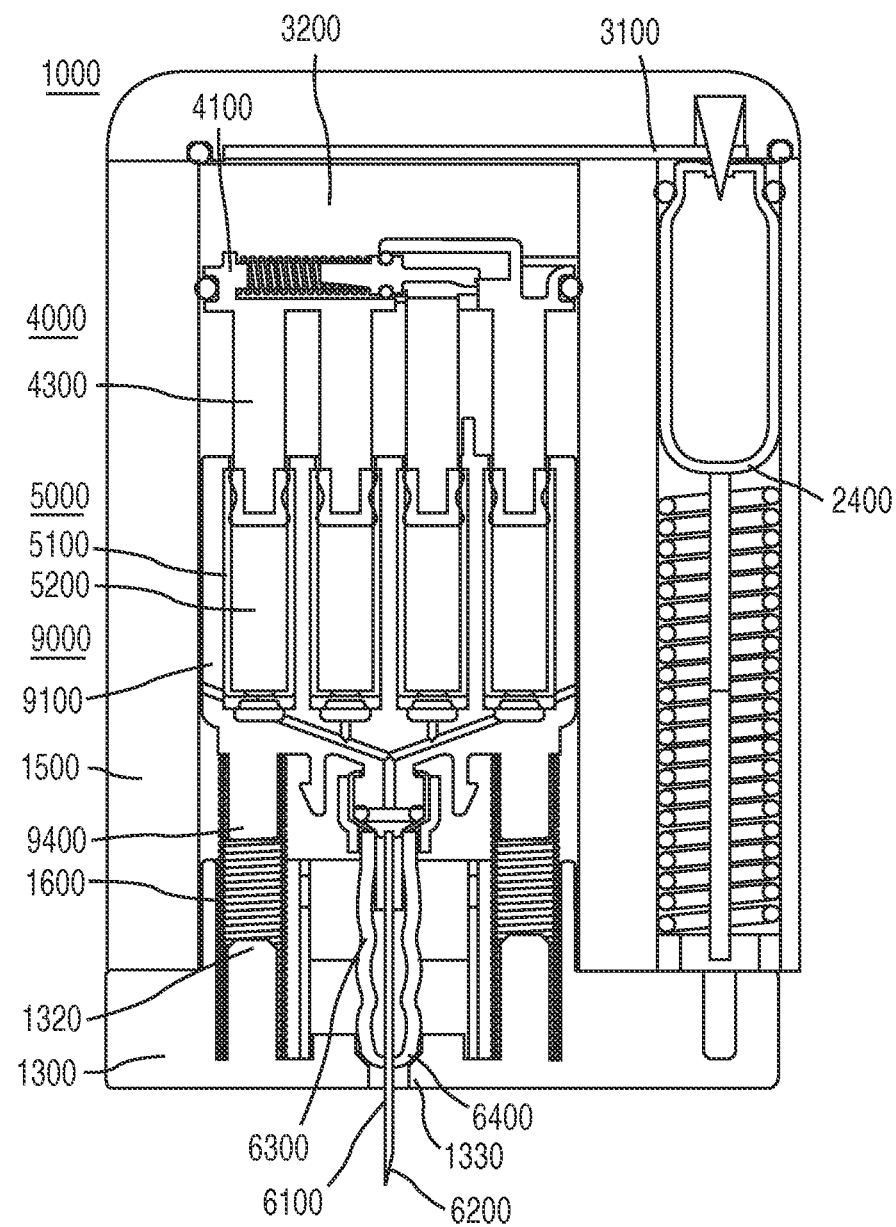
FIG. 6 is a cross-sectional view taken along line A-A of FIG. 3 of a system according to an embodiment of the invention in a third operative position.

Referring to FIG. 6, as at least a portion of contents 2500 of gas container 2400 escapes, it can flow through channel 3100. The gas, which can still be relatively pressurized, can begin to accumulate behind pusher 4100 to form an expanding gas chamber 3200 and to cause medicament actuator 4000, medicament storage assembly 5000, and medicament carrier 9000 to slide together within sleeve 1500. As medicament actuator 4000, medicament storage assembly 5000, and medicament carrier 9000 slide closer to actuator bar 1300, spring 1600 becomes increasingly compressed between bar stop 1320 and medicament carrier stop 9400. As medicament actuator 4000, medicament storage assembly 5000, and medicament carrier 9000 slide closer to actuator bar 1300, needle tip 6200 can extend further from actuator bar 1300 and sheath 6300 can become further compressed and/or deformed. At its ultimate extension point, needle tip 6200 can extend from housing 1100 from approximately 0.25 millimeters to approximately 20 millimeters, including all values and subranges therebetween, such as up to approximately 2 millimeters, greater than approximately 5 millimeters, from approximately 5.13 millimeters to approximately 9.98 millimeters, etc.

Figure 7:
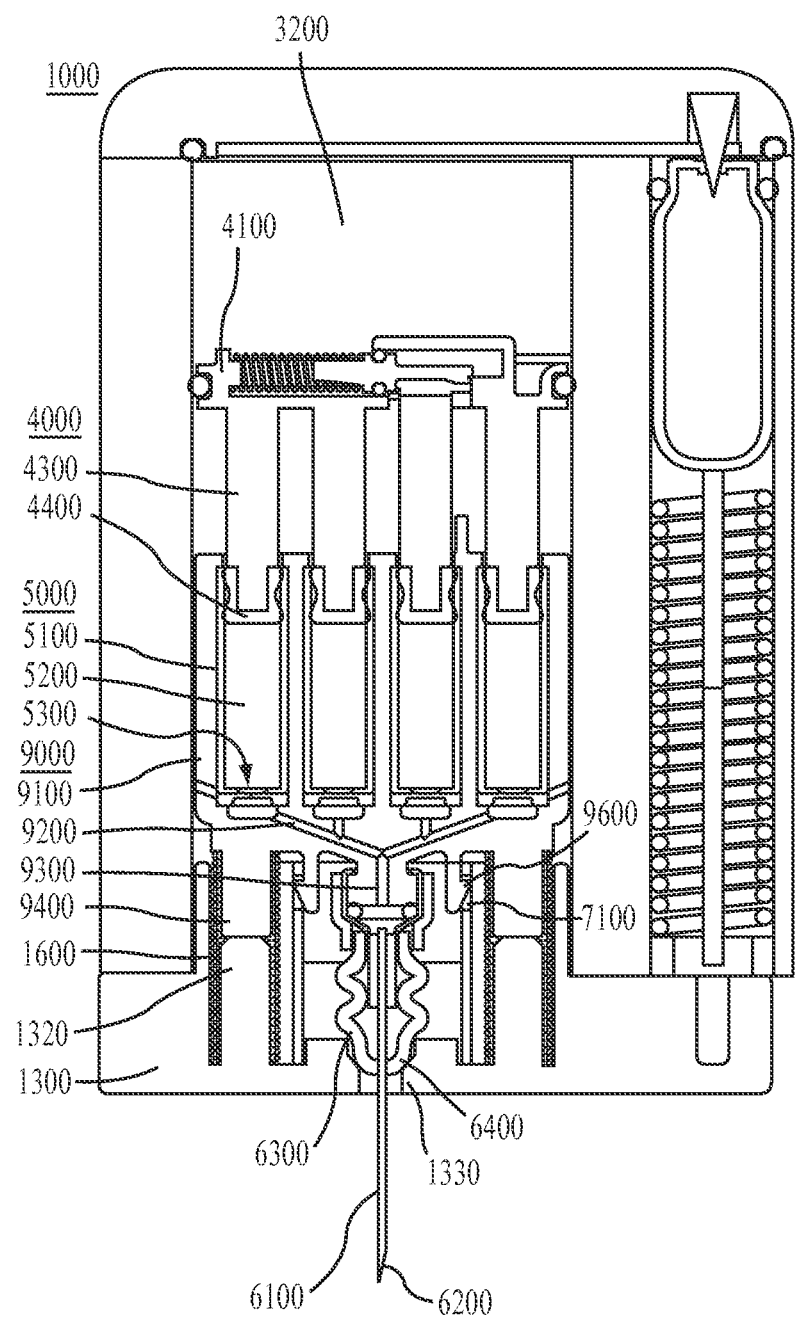
FIG. 7 is a cross-sectional view taken along line A-A of FIG. 3 of a system according to an embodiment of the invention in a fourth operative position.

Referring to FIG. 7, as gas chamber 3200 continues to expand, medicament carrier 9000 can be driven until medicament carrier stop 9400 contacts actuator bar stop 1300 thereby resisting further travel of medicament carrier 9000. At that point, additional expansion of gas chamber 3200 can cause medicament actuator 4000, pusher 4100, plungers 4300, and/or pistons 4400 to initiate travel with respect to medicament storage assembly 5000, thereby generating an expulsion pressure in vials 5100, and/or thereby rupturing frangible seals 5300 and allowing medicament 5200 to enter medicament carrier 9000, and begin flowing through medicament channels 9200, medicament conduit 9300, needle 6100, and/or out needle tip 6200 and into a patient. Alternatively, frangible seals 5300 can be replaced and/or augmented by a frangible seal located at or near where medicament conduit 9300 couples to needle 6100. Frangible seals 5300 can be constructed of a thin, taught, resilient, durable, and/or sealing material potentially having a predetermined yield strength, such as a rubber, such as chromo butyl rubber, and/or of a relatively brittle material potentially having a predetermined yield strength, such as ceramic, certain plastics, such as polystyrene, etc.

As medicament carrier stop 9400 contacts actuator bar stop 1320, medicament carrier hooks 9600 can engage with engagement receivers 7100 in use indicator 7000.

Figure 8:
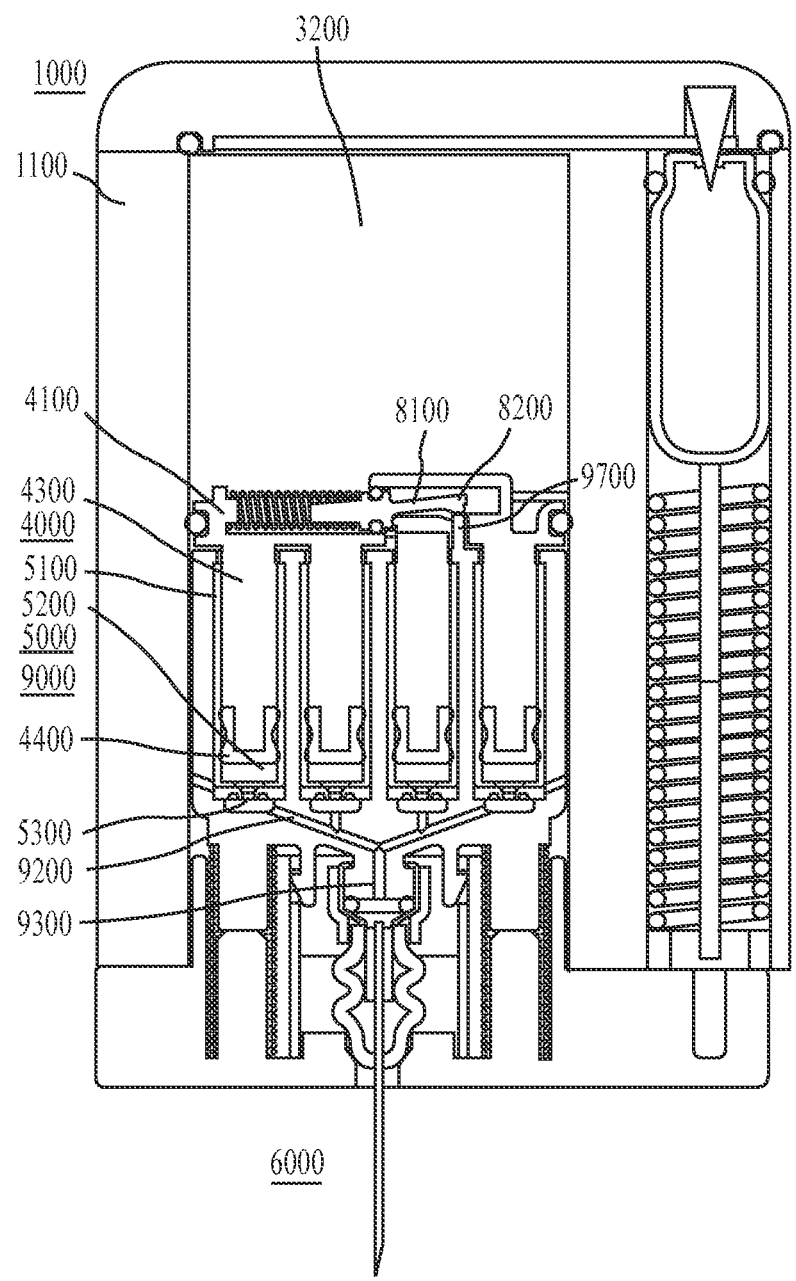
FIG. 8 is a cross-sectional view taken along line A-A of FIG. 3 of a system according to an embodiment of the invention in a fifth operative position.

Referring to FIG. 8, as gas chamber 3200 continues to expand, medicament actuator 4000, pusher 4100, plungers 4300, and/or pistons 4400 can continue moving until they complete their travel within medicament storage assembly 5000, thereby expelling a predetermined dose of medicament 5200 from vials 5100, out of needle assembly 6000, external to housing 1100, and/or into the patient. As gas chamber 3200 reaches its maximum size, medicament actuator 4000, pusher 4100, plungers 4300, and/or pistons 4400 can continue moving until they complete their travel with respect to medicament carrier 9000, thereby causing gas release actuator 9700 to engage with gas relief valve 8200. Engagement of gas release actuator 9700 with gas relief valve 8200 can cause gas within gas chamber 3200 to exit gas chamber 3200, discharge away from pistons 4400, and/or exhaust from system 1000 and/or housing 1100, such as via status indicator 1400 and/or a gas escape port located on housing 1100).

Figure 9:
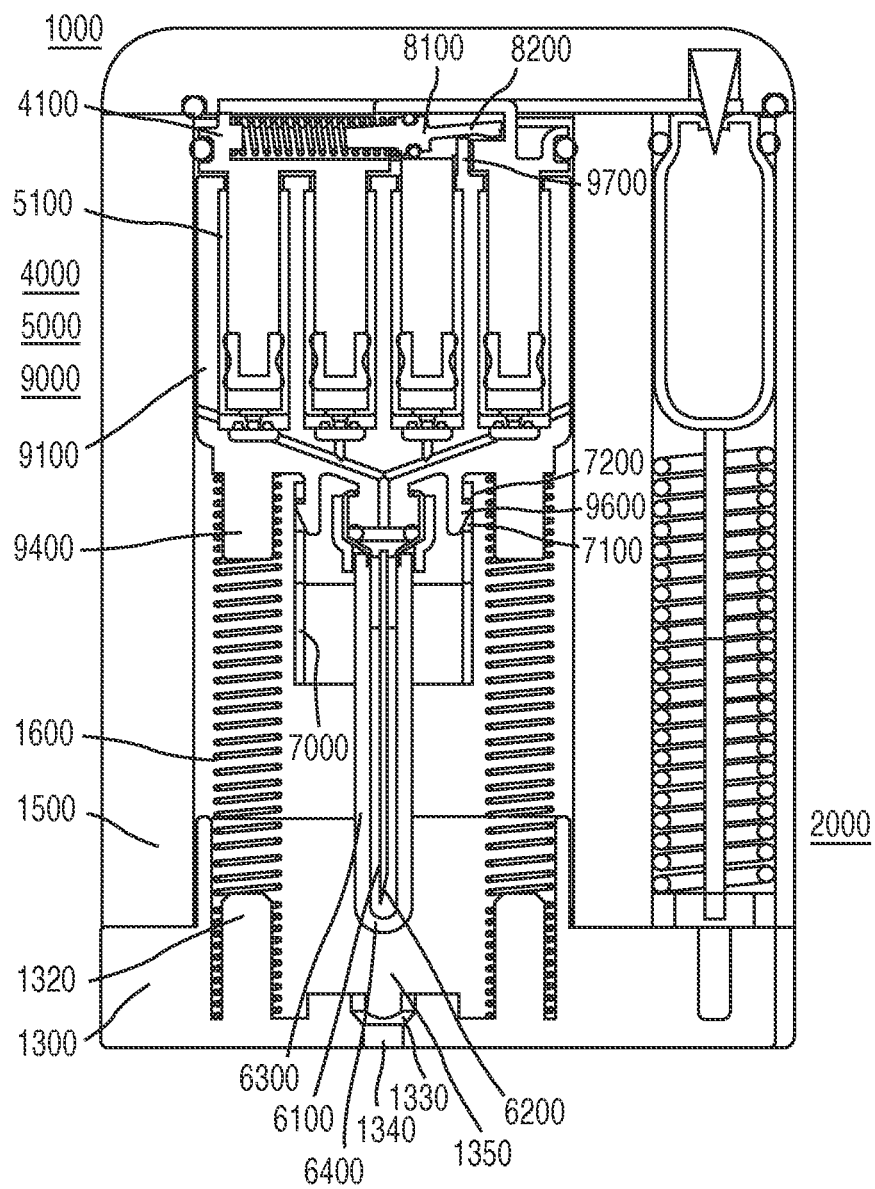
FIG. 9 is a cross-sectional view taken along line A-A of FIG. 3 of a system according to an embodiment of the invention in a sixth operative position.

Referring to FIG. 8 and FIG. 9, as sufficient gas is vented from gas chamber 3200, the pressure applied by the gas in gas chamber 3200 can decrease until the force applied by the gas on medicament actuator 4000 is less than the force of compressed spring 1600. Thus, spring(s) 1600 can begin to expand, thereby moving medicament carrier 9000, vial assembly 5000, and medicament actuator 4000 away from actuator bar 1300 and helping to exhaust gas from gas chamber 3200. As medicament carrier 9000 moves, use indicator 7000 can travel with it, due to the engaged relationship of medicament carrier hooks 9600 and engagement receivers 7100 and/or engagement catches 7200 in use indicator 7000. As use indicator 7000 moves away from actuation bar 1300, sheath 6300 can travel with it, thereby creating a gap between sheath tip 6400 and needle port 1340, and thereby exposing a previously non-visible colored portion 1350 of actuation bar 1300 and/or providing an indication that system 1000 has been used (and likely substantially exhausted of its medicament), thereby discouraging any further attempts to use system 1000.

As medicament carrier 9000 moves away from actuator bar 1300, needle 6100 can retract into sheath 6300 which un-buckles and/or un-deforms towards its original shape. Eventually, needle 6100 can retract completely within the boundaries of housing 1100, thereby tending to prevent accidental needle sticks after the initial injection and/or potentially reducing and/or eliminating a sharps hazard.

In some embodiments, system actuator 2000 can comprise a finger triggered, twistable, pivotable, and/or lever-operated mechanism. For example, system actuator 2000 can comprise a twistable handle that can screw into gas port 2600. In some embodiments, system actuator 2000 can be a finger trigger located on a side of the housing.

Figure 10:
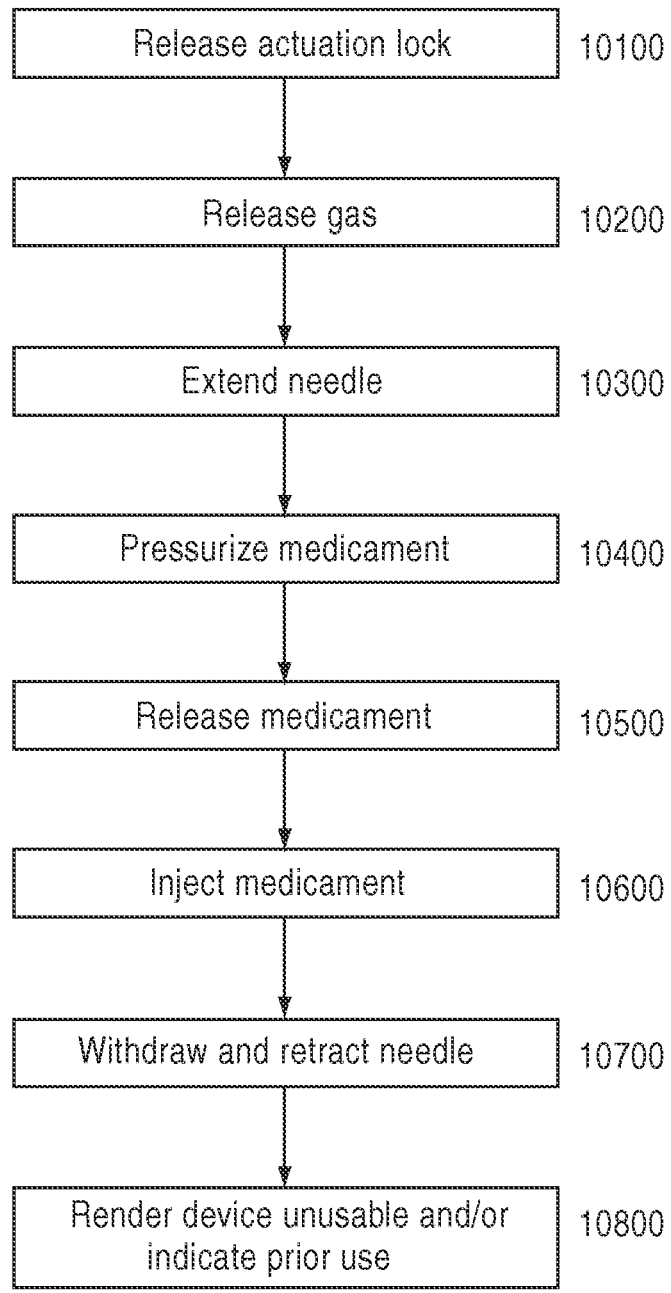
FIG. 10 is a flowchart illustrating a method according to an embodiment of the invention.

FIG. 10 is a flowchart of an embodiment of a method 10000 for operating a medicament delivery apparatus. At activity 10100, an actuation lock for the apparatus is released. At activity 10200, an actuating portion of the contents of a compressed gas container are released. At activity 10300, via pressure provided by the released gas, a needle is extended from the apparatus. At activity 10400, via pressure provided by the released gas, a piston applies pressure to a medicament stored in one of a plurality of vials. At activity 10500, a frangible seal containing the medicament in the vial is burst. At activity 10600, the medicament flows from the vial, through the needle, and into a patient. At activity 10700, once a predetermined dose is expelled and/or injected, the needle is withdrawn from the patient and/or retracted into the pre-use bounds of the apparatus. At activity 10800, the apparatus is rendered unusable for additional injections and/or indicated as previously utilized.

Figure 11:
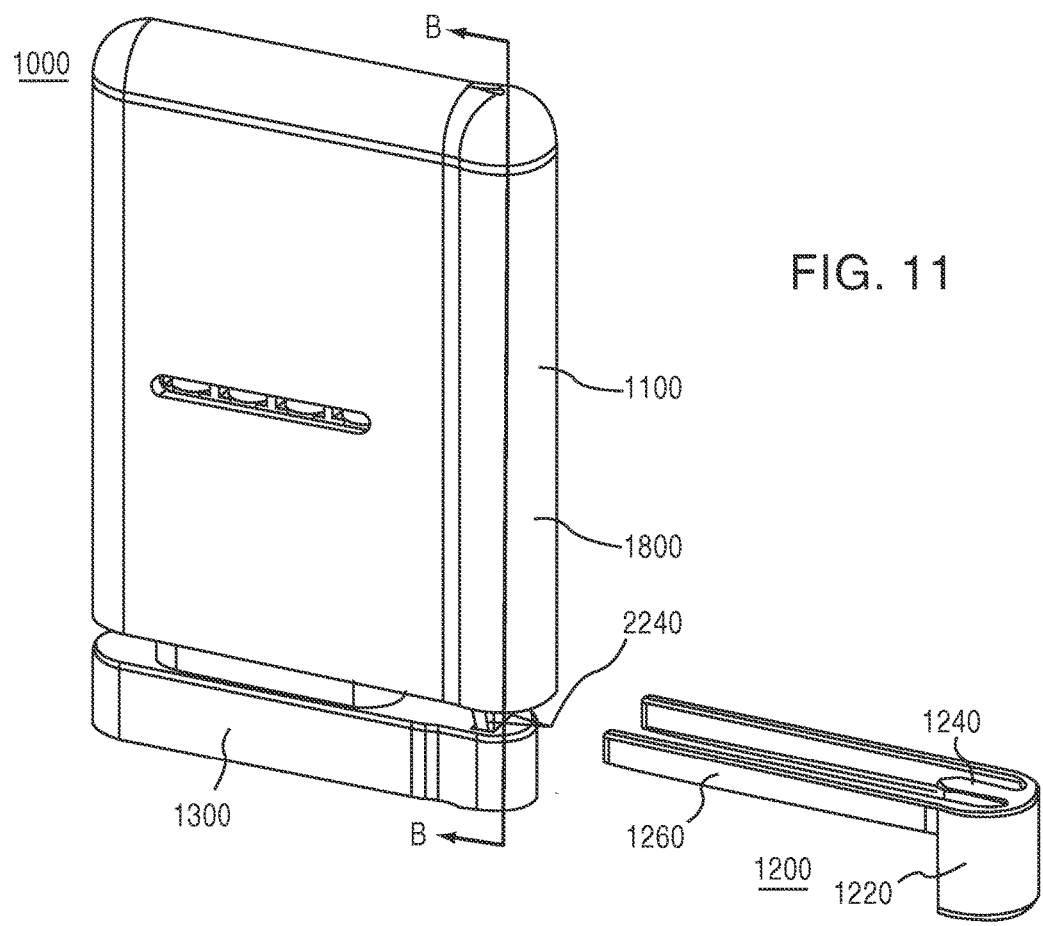
FIG. 11 is a perspective view of a system according to an embodiment of the invention.

FIG. 11 is a perspective view of an embodiment of system 1000, showing actuation guard 1200 removed from housing 1100, so that actuation guard 1200 no longer separates actuator bar 1300 from handheld portion 1800. Actuation guard 1200 can comprise a grippable portion 1220 that can be gripped by a user to pull actuation guard 1200 away from housing 1100, thereby allowing system 1000 to be activated, such as via slapping actuator bar 1300 against a thigh of the user. Actuation guard 1200 can comprise an actuation stick separator portion 1240, that can keep separate actuation stick prongs 2240 when actuation guard 1200 is installed on housing 1100. Actuation guard 1200 can comprise a guard portion 1260 that can separate actuator bar 1300 from handheld portion 1800 when system 1000 is not in use and/or when system 1000 has not been used.

Figure 12:
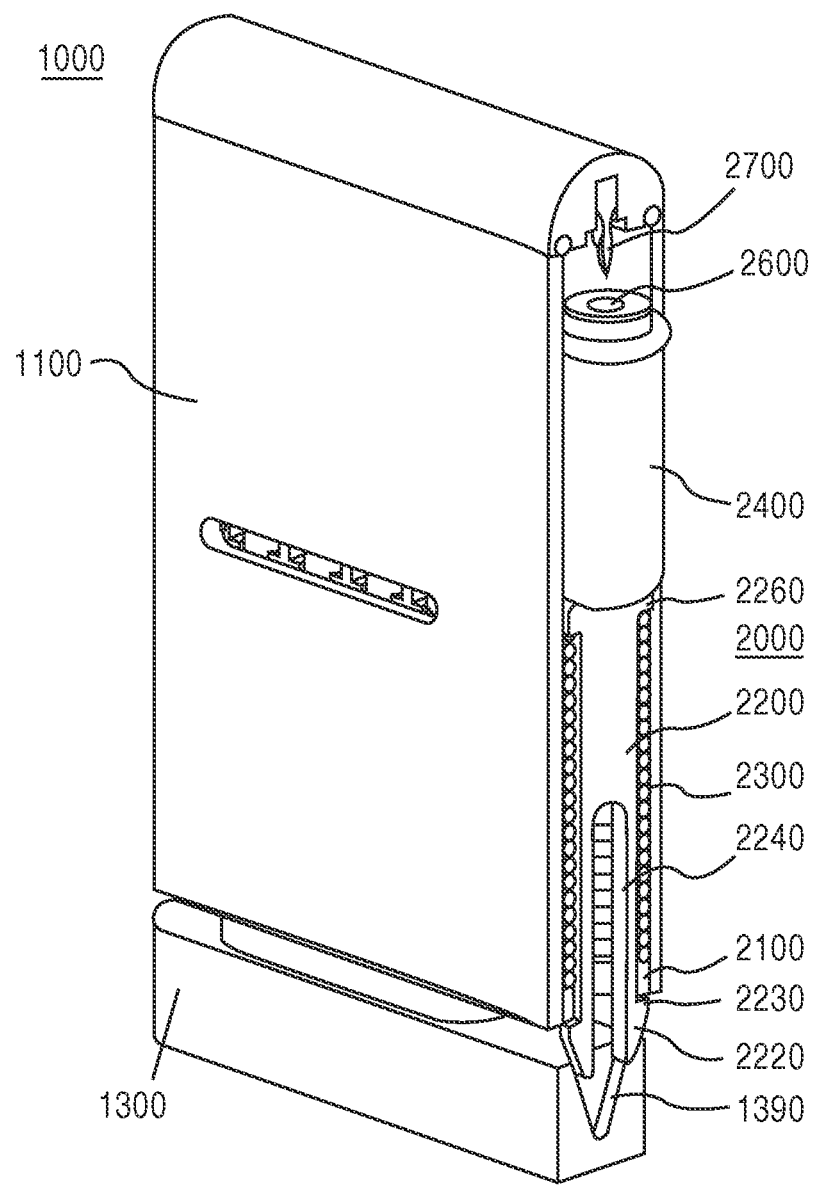
FIG. 12 is a perspective cross-sectional view the system illustrated in FIG. 11 taken along line B-B of FIG. 11.
Figure 13:
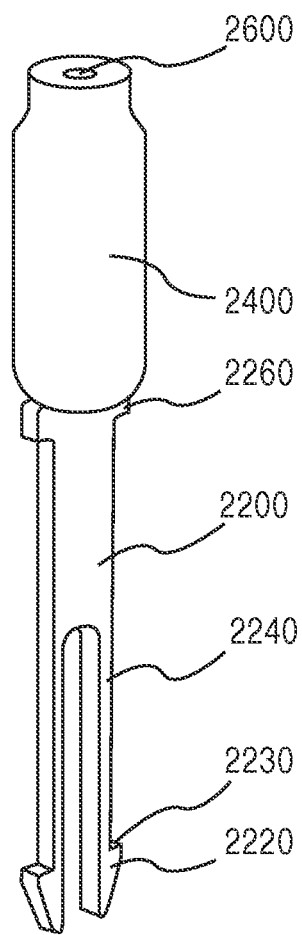
FIG. 13 is a perspective view of an apparatus according to an embodiment of the invention.

FIG. 12 is a perspective cross-sectional view taken along line B-B of FIG. 11, and FIG. 13 is a perspective view of an embodiment of actuation stick 2200. Referring to FIGS. 12 and 13, system 1000 can comprise housing 1100, actuation bar 1300, and system actuator 2000, which can comprise prong squeezer 1390, actuation stick 2200, prong retainer 2100, spring 2300, upper spring retainer 2260, gas container 2400, gas port 2600, and/or puncturer 2700. When actuation bar 1300 is pressed firmly against a user's body, such as via slapping housing actuation bar against the user's thigh, buttocks, and/or arm, prong squeezer 1390 can urge prong tips 2220 of prongs 2240 of actuation stick 2200 toward one another. Note that prong tips 2200 can have a triangular, wedge, angular, and/or frusto-conical shape. As prongs tips 2220 slide along the angled V-groove of prong squeezer 1390, prong catches 2230 can substantially lose contact with prong retainer 2100. This can allow compressed spring 2300 to rapidly urge actuation stick 2200 and gas container 2400 toward puncturer 2700, which can penetrate gas port 2600, thereby allowing gas to escape from gas container 2400. Although any of many different types of gas containers can be utilized, an example of a suitable gas container can be obtained from Leland Limited, Inc. of South Plainfield, N.J.

Figure 14:
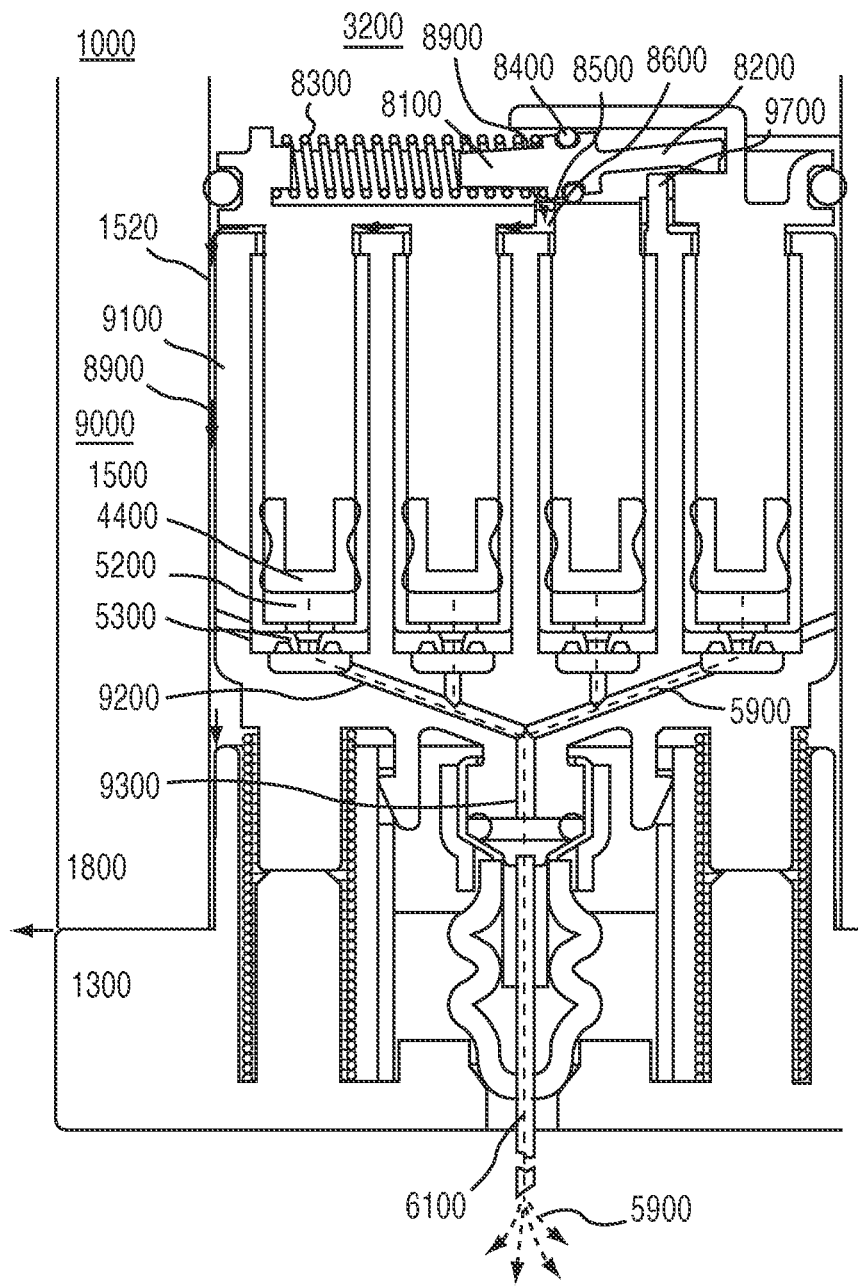
FIG. 14 is a cross-sectional view of a mechanism according to an embodiment of the invention taken along line A-A of FIG. 3.

FIG. 14 is a cross-sectional view of an embodiment of gas venting mechanism 8000 of system 1000 taken along line A-A of FIG. 3. System 1000 can comprise handheld portion 1800, actuator bar 1300, sleeve 1500. As pistons 4440 near the limit of their travels, medicament 5200 can be expelled along medicament path 5900, which can extend past frangible seal 5300, through medicament channels 9200, medicament conduit 9300, and needle 6100, and into the body of a user, such as subcutaneously, intramuscularly, and/or at a depth of from approximately 0.25 millimeters to approximately 20 millimeters, including all values and subranges therebetween, such as up to 2 millimeters, greater than 5 millimeters, etc.

As pistons 4440 near the limit of their travels, engagement of gas release actuator 9700 with gas relief valve 8200 can cause compressed spring 8300 to move valve arm such that o-ring 8400 is urged away from its seat 8500. This movement can reveal a passage 8600, via which gas can exit gas chamber 3200 along gas exhaust path 8900, which can extend between sleeve inner walls 1520 and outer walls 9100 of medicament carrier 9000. Eventually, gas exhaust path 8900 can extend between handheld portion 1800 and actuator bar 1300. Likewise, an alternative embodiment of valve 8200, made of rubber or any other resilient material, can be placed across seat 8500 to provide a seal that, once gas release actuator 9700 interacts with valve 8200, allows valve 8200 to bend or flap upwards away from seat 8500, causing the gas to escape via passage 8600.

Figure 15:
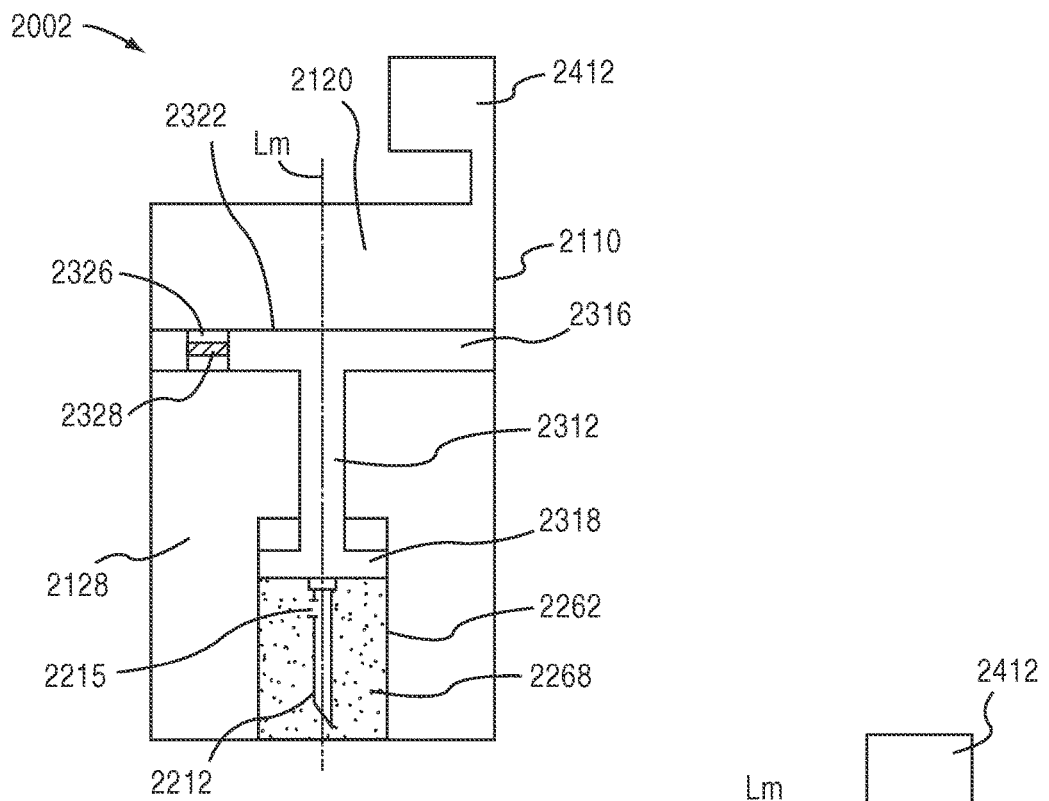
FIGS. 15 and 16 are schematic illustrations of an auto-injector according to an embodiment of the invention in a first configuration and a second configuration, respectively.
Figure 16:
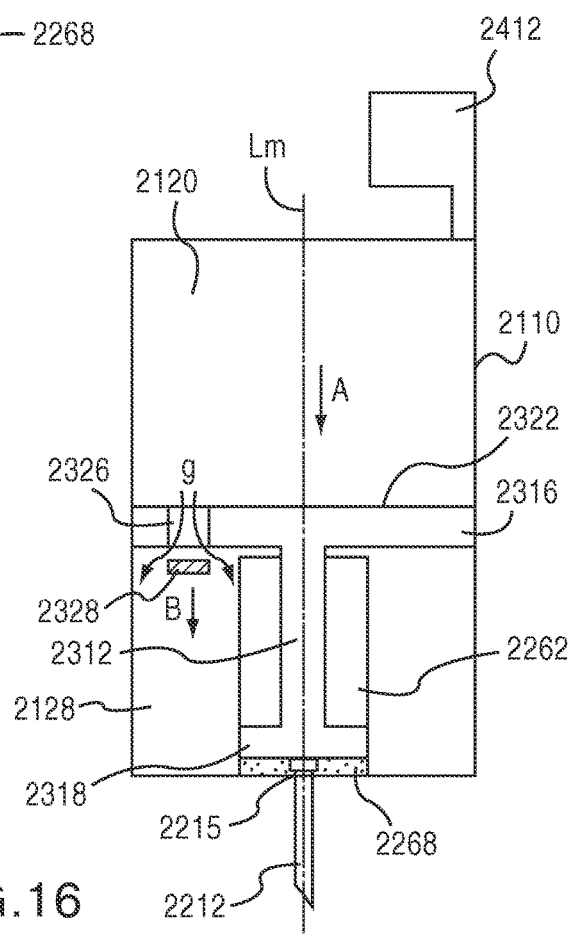

FIGS. 15 and 16 are schematic illustrations of an auto-injector 2002 according to an embodiment of the invention in a first configuration and a second configuration, respectively. The auto-injector 2002 includes a housing 2110, a medicament container 2262, a movable member 2312, a gas relief valve 2328 and a compressed gas source 2412. The medicament container 2262, which can be, for example, a pre-filled cartridge, a vial, an ampule or the like, is fixedly disposed within the housing 2110 and defines a longitudinal axis Lm. The medicament container 2262 contains a medicament 2268, such as, for example, epinephrine.

The movable member 2312 includes a proximal end portion 2316 and a distal end portion 2318. The proximal end portion 2316 includes a surface 2322 that, together with the housing 2110, defines a gas chamber 2120. Said another way, the surface 2322 defines a portion of a boundary of the gas chamber 2120. The proximal end portion 2316 defines an opening 2326 therethrough, which is in fluid communication between the gas chamber 2120 and an area outside of the gas chamber 2128. The distal end portion 2318 is movably disposed within the medicament container 2262 along the longitudinal axis Lm, as shown by the arrow A. A needle 2212 is coupled to the distal end 2318 of the movable member 2312. The needle 2212 defines a lumen (not shown) and a side opening 2215.

The gas relief valve 2328 is coupled to the movable member 2312 such that it can selectively allow fluid communication between the gas chamber 2120 and the area outside of the gas chamber 2128. The gas relief valve 2328 can include, for example, a movable membrane, a frangible seal, a spring-loaded gas relief valve body or the like.

In use, when the auto-injector 2002 is actuated, the gas chamber 2120 is placed in fluid communication with the compressed gas source 2412, thereby allowing a pressurized gas to flow into the gas chamber 2120. In response to a force produced by the pressurized gas on the surface 2322 of the movable member 2312, the movable member 2312 moves within the housing 2110 and the medicament container 2262, as indicated by arrow A. As a result, as shown in FIG. 16, the needle 2212 is extended through the housing 2110. The movement of the movable member 2312 also forces the medicament 2268 through the side opening 2215 and into the lumen (not shown) defined by the needle 2212. In this manner, the medicament injection occurs while the needle 2212 is being extended from the housing 2110 (i.e., while the needle 2212 is being inserted into the body).

In use, the pressure of the pressurized gas within the gas chamber 2120 can be controlled by the gas relief valve 2328. As shown in FIG. 16, the gas relief valve 2328 is actuated as indicated by the arrow B, thereby allowing pressurized gas to flow from the gas chamber 2120 to the area outside of the gas chamber 2128 through the opening 2326, as shown by the arrows g. Although the gas relief valve 2328 is shown as being actuated after substantially all of the medicament 2268 has been injected, in other embodiments, the gas relief valve 2328 can be actuated at any time during the injection event. For example, in some embodiments, the gas relief valve 2328 can be actuated as the injection event is beginning to control the rate of needle insertion and/or medicament injection. In other embodiments, the gas relief valve 2328 can be actuated at the end of the injection event to allow the needle 2212 to be retracted to a position within the housing 2110. In yet other embodiments, the gas relief valve 2328 can be actuated upon completion of the injection event to prevent residual gas from undesirably building up within the gas chamber 2120.

Figure 17:
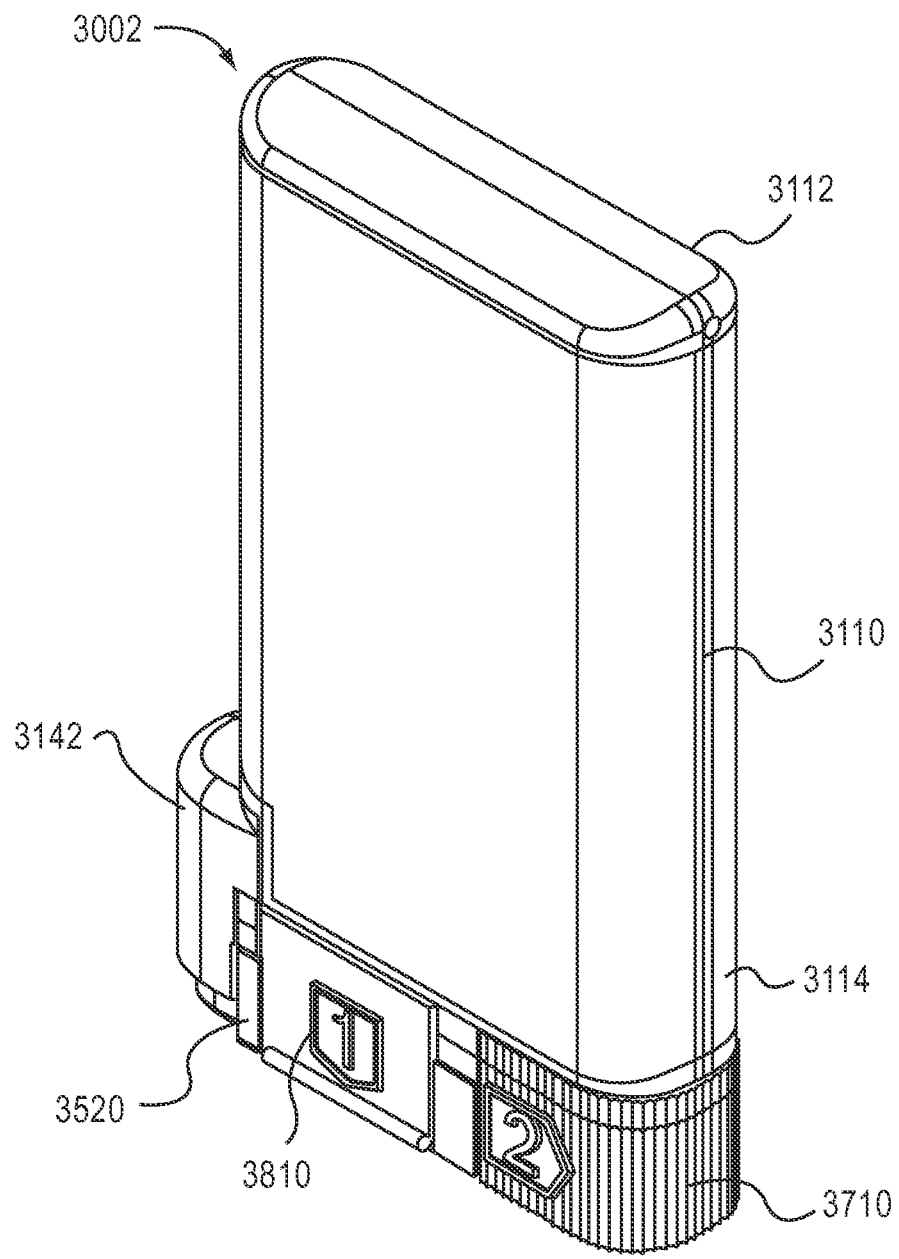
FIG. 17 is a perspective view of an auto-injector according to an embodiment of the invention.

FIG. 17 is a perspective view of an auto-injector 3002 according to an embodiment of the invention in a first configuration. The auto-injector 3002 includes a housing 3110 having a proximal end portion 3112 and a distal end portion 3114. The distal end portion 3114 of the housing 3110 includes a protrusion 3142 to help a user grasp and retain the housing 3110 when using the auto-injector 3002. Said another way, the protrusion 3142 is configured to prevent the auto-injector 3002 from slipping from the user's grasp during use. A base 3520 is movably coupled to the distal end portion 3114 of the housing 3110. A needle guard assembly 3810 is removably coupled to the base 3520. Similarly, a safety lock 3710 is removably coupled to the base 3520. To inject a medicament into the body, the distal end portion 3114 of the housing is oriented towards the user such that the base 3520 is in contact with the portion of the body where the injection is to be made. The base 3520 is then moved towards the proximal end 3112 of the housing 3110 to actuate the auto-injector 3002. The housing 3110 also includes a transparent status window 3118 (see FIG. 36) to allow a user to determine the status of the auto-injector 3002 or the medicament contained therein.

Figure 18:
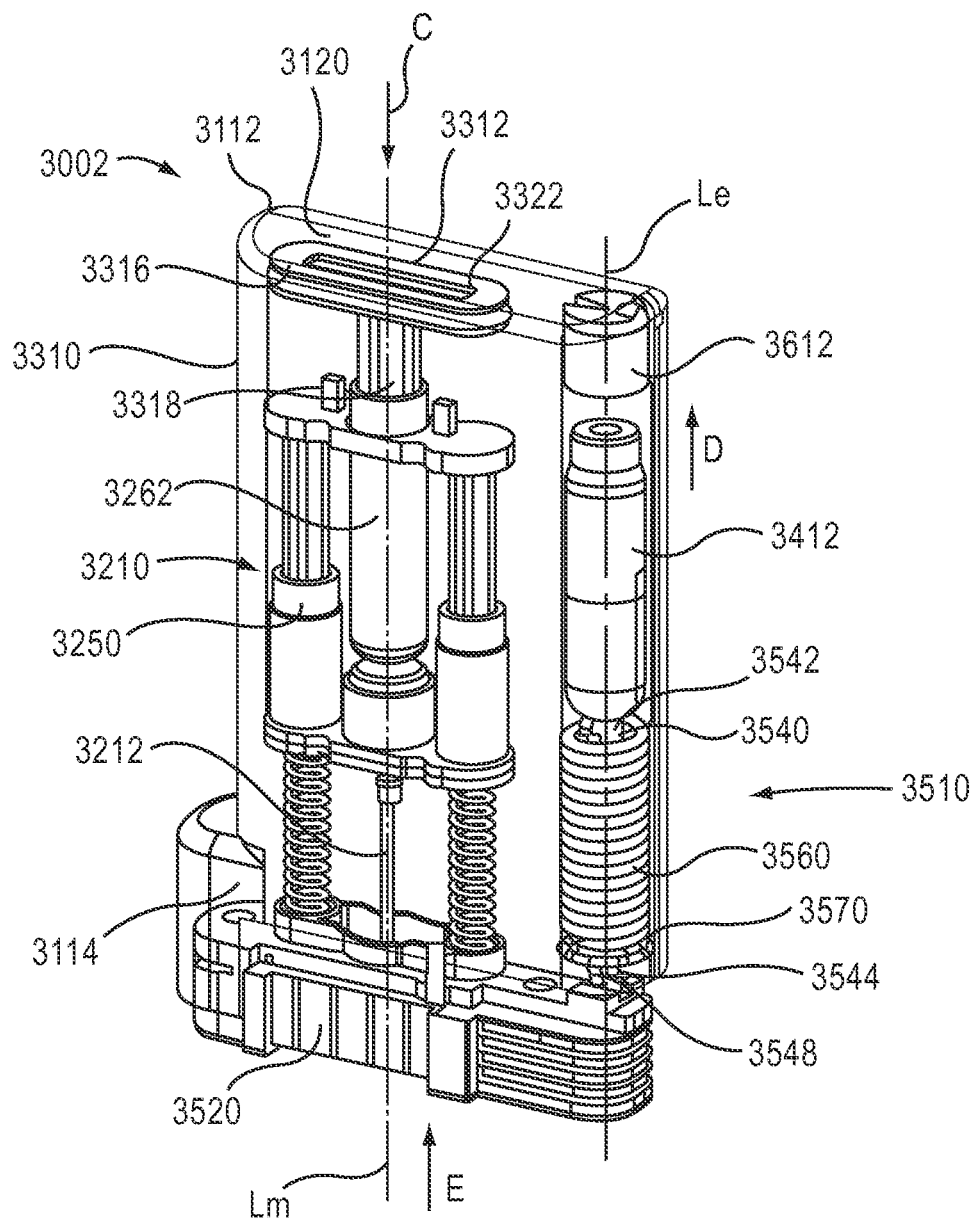
FIG. 18 is a perspective view of the auto-injector illustrated in FIG. 17 in a first configuration, with at least a portion of the auto-injector illustrated in phantom lines for ease of reference.
Figure 19:
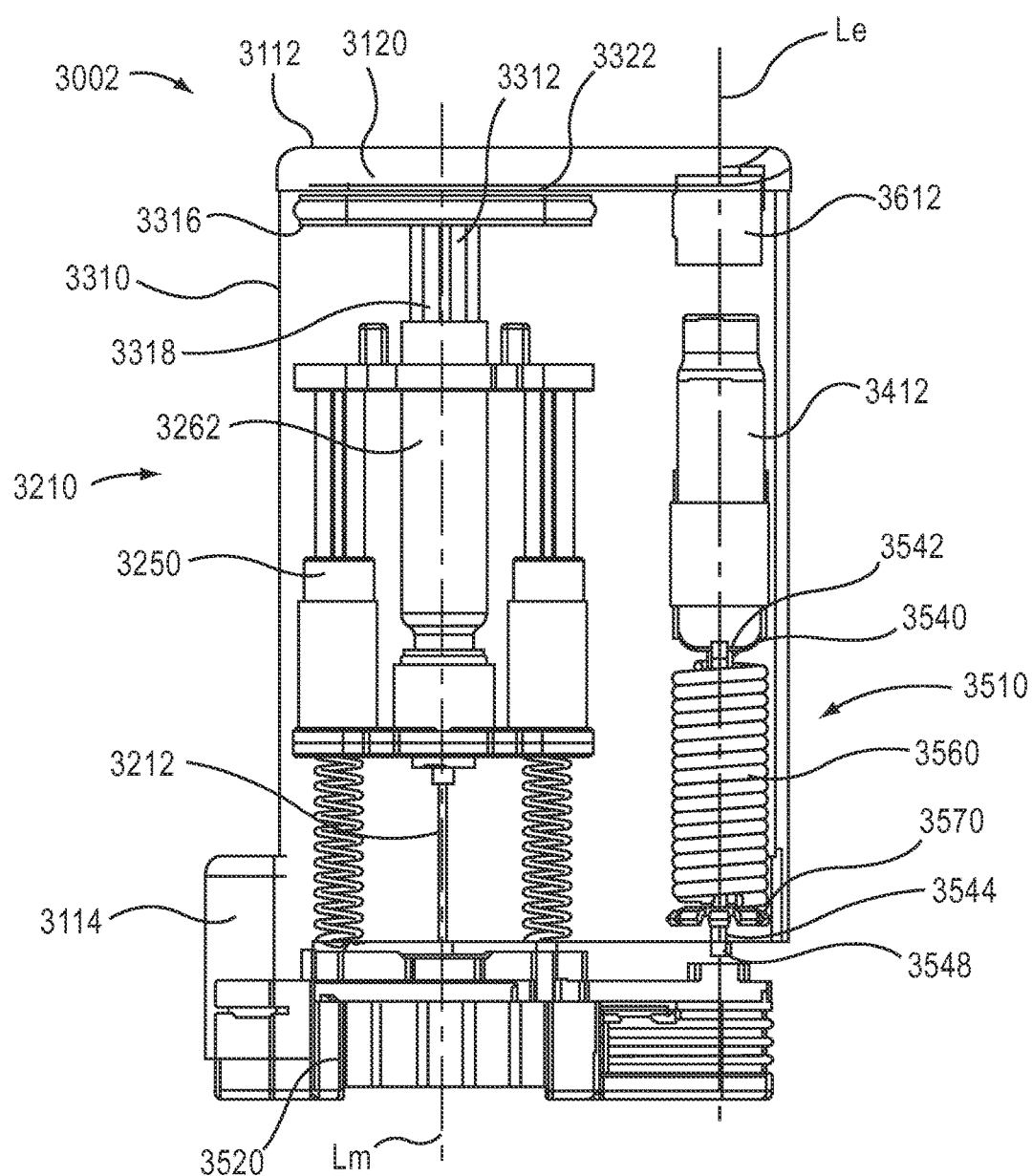
FIG. 19 is a front view of the auto-injector illustrated in FIGS. 17 and 18 in a first configuration.

FIG. 18 is a perspective view of the auto-injector 3002 showing the housing 3110 in phantom lines so that the components contained within the housing 3110 can be more clearly seen. For clarity, FIG. 18 shows the auto-injector 3002 without the needle guard assembly 3810 and the safety lock 3710. Similarly, FIG. 19 is a front view of the auto-injector 3002 showing the housing 3110 in phantom lines. The auto-injector 3002 includes a medicament injector 3210 and a movable member 3312 engaged with the medicament injector 3210, each of which are disposed within the housing 3110. The auto-injector 3002 also includes a system actuator 3510, a compressed gas container 3412 and a gas release mechanism 3612.

The medicament injector 3210 includes a carrier 3250 that is movable within the housing 3110, a medicament container 3262 and a needle 3212. The medicament container 3262 is coupled to the carrier 3250. The needle 3212 is disposed within a needle hub portion 3223 (see FIG. 22) of the carrier to allow the needle 3212 to be placed in fluid communication with the medicament container 3262 during an injection event.

The movable member 3312 includes a proximal end portion 3316 and a distal end portion 3318. The proximal end portion 3316 includes a surface 3322 that, together with the housing 3110, defines a gas chamber 3120. Said another way, the surface 3322 defines a portion of a boundary of the gas chamber 3120. The distal end portion 3318 is disposed within the medicament container 3262. In use, the movable member 3312 moves towards the distal end portion 3114 of the housing 3110, as indicated by arrow C, in response to a force produced by a pressurized gas on the surface 3322 of the movable member 3312. As a result, the movable member 3312 and the medicament injector 3250 are moved towards the distal end portion 3114 of the housing 3110, thereby exposing the needle 3212 from the housing 3110. The movable member 3312 then continues to move within the medicament container 3262 to expel a medicament from the medicament container 3262 through the needle 3212.

The auto-injector 3002 is actuated by the system actuator 3510, which is configured to move the compressed gas container 3412 into contact with the gas release mechanism 3612. The gas release mechanism 3612 punctures a portion of the compressed gas container 3412 to release the pressurized gas contained therein into the gas chamber 3120 defined by the housing 3110.

The system actuator 3510 includes a rod 3540, a spring 3560 and a spring retainer 3570. The rod 3540 has a proximal end portion 3542 and a distal end portion 3544. The proximal end portion 3542 of the rod 3540 is coupled to the compressed gas container 3412. The distal end portion 3544 of the rod 3540 is coupled to the spring retainer 3570 by two projections 3548, which can be moved inwardly towards each other to decouple the rod 3540 from the spring retainer 3570, as discussed below.

The spring 3560 is disposed about the rod 3540 in a compressed state such that the spring 3560 is retained by the proximal end portion 3542 of the rod 3540 and the spring retainer 3570. In this manner, the rod 3540 is spring-loaded such that when the distal end portion 3544 of the rod 3540 is decoupled from the spring retainer 3570, the force of the spring 3560 causes the rod 3540, and therefore the compressed gas container 3412, to move proximally as indicated by arrow D and into contact with the gas release mechanism 3612.

The base 3520 defines an opening 3522 configured to receive a portion of the projections 3548 when the base is moved towards the proximal end 3112 of the housing 3110, as indicated by arrow E. When the projections 3548 are received within the opening 3522, they are moved together causing the distal end portion 3544 of the rod 3540 to be released from the spring retainer 3570.

As shown in FIGS. 18 and 19, the medicament injector 3210 defines a longitudinal axis Lm that is non-coaxial with the longitudinal axis Le defined by the compressed gas container 3412. Accordingly, the medicament injector 3210, the compressed gas container 3412 and the system actuator 3510 are arranged within the housing 3110 such that the housing has a substantially rectangular shape. Moreover, the non-coaxial relationship between the medicament injector 3210 and the compressed gas container 3412 allows the auto-injector 3002 to be actuated by manipulating the base 3520, which is located at the distal end portion 3114 of the housing 3110.

As discussed above, the use and actuation of the auto-injector 3002 includes several discrete operations. First, the auto-injector 3002 is enabled by removing the needle guard 3810 and the safety lock 3710 (see FIGS. 20 and 21). Second, the auto-injector 3002 is actuated by moving the base 3520 proximally towards the housing 3110. Third, when actuated, the compressed gas container 3412 engages the gas release mechanism 3612, which causes the pressurized gas to be released into the gas chamber 3120 (see FIG. 31). Fourth, the pressurized gas produces a force that causes the movable member 3312 and the medicament injector 3210 to move distally within the housing 3110 (see FIG. 37). The movement of the medicament injector 3210 causes the needle 3212 to extend from distal end portion 3114 of the housing 3110 and the base 3520. This operation can be referred to as the "needle insertion" operation. Fifth, when the medicament injector 3210 has completed its movement (i.e., the needle insertion operation is complete), the movable member 3312 continues to move the medicament container 3262 distally within the carrier 3250. The continued movement of the medicament container 3262 places the needle 3212 in fluid communication with the medicament container 3262, thereby allowing the medicament to be injected (see FIG. 43). Sixth, the force from the pressurized gas causes the movable member 3312 to move within the medicament container 3262, thereby expelling the medicament through the needle 3212 (see FIG. 44). This operation can be referred to as the "injection operation." Seventh, upon completion of the injection, the pressurized gas is released from the gas chamber 3120, thereby allowing the medicament injector 3210 and the movable member 3312 to be moved proximally within the housing. This operation can be referred to as the "retraction operation" (see FIG. 45). A detailed description of the components contained in the auto-injector 3002 and how they cooperate to perform each of these operations is discussed below.

Prior to use, the auto-injector 3002 must first be enabled by first removing the needle guard 3810 and then removing the safety lock 3710. As illustrated by arrow G in FIG. 20, the needle guard 3810 is removed by pulling it distally. Similarly, as illustrated by arrow H in FIG. 21, the safety lock 3710 is removed by pulling it substantially normal to the longitudinal axis Le of the compressed gas container 3412. Said another way, the safety lock 3710 is removed by moving it in a direction substantially normal to the direction that the needle guard 3810 is moved. As described in more detail herein, the needle guard 3810 and the safety lock 3710 are cooperatively arranged to prevent the safety lock 3710 from being removed before the needle guard 3810 has been removed. Such an arrangement prevents the auto-injector 3002 from being actuated while the needle guard 3810 is in place.

Figure 22:
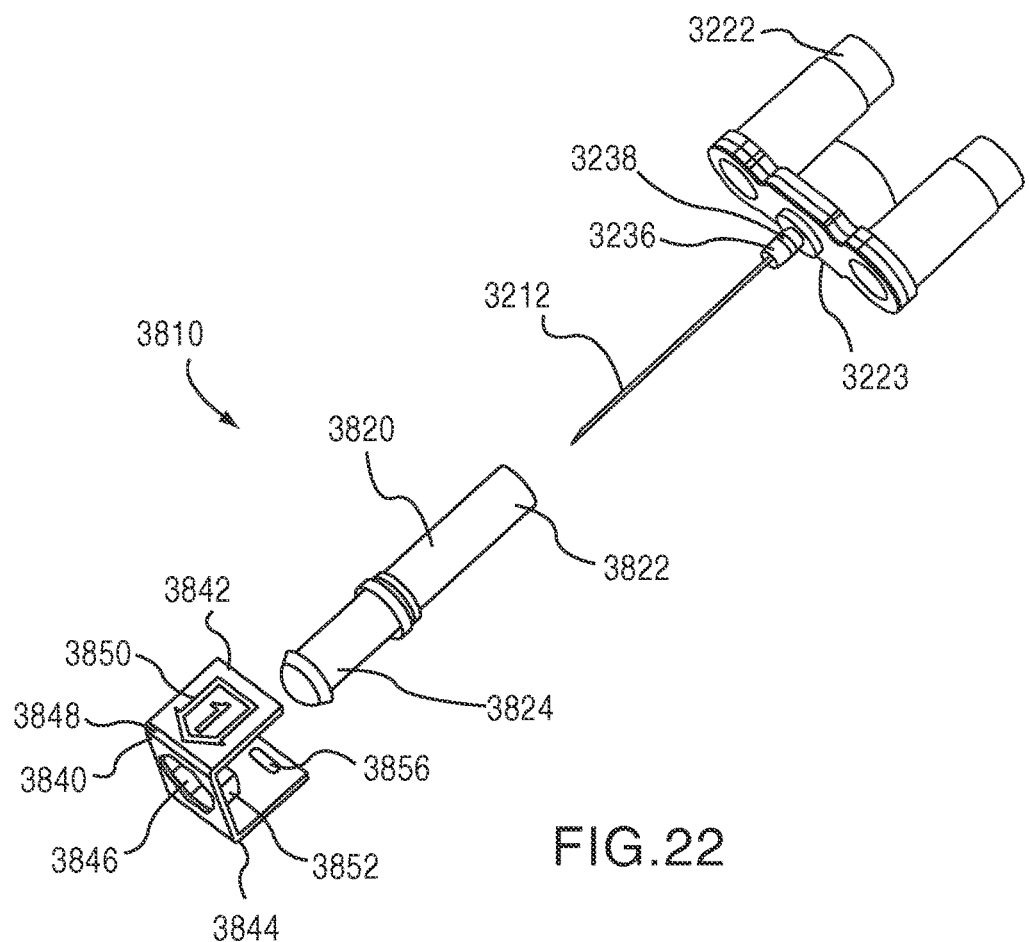
FIG. 22 is an exploded perspective view of a portion of the auto-injector illustrated in FIG. 20.

As illustrated in FIG. 22, the needle guard 3810 includes a sheath 3820 and a sheath retainer 3840. The sheath 3820 has a proximal end portion 3822 and a distal end portion 3824 and defines an opening 3826 configured to receive a portion of the needle 3212 when the needle guard 3810 is in a first (or installed) position. The sheath 3820 further defines a recessed portion 3828 within the opening 3826 that engages a corresponding protrusion 3238 defined by an outer surface 3236 of the needle hub 3223. In this manner, when the needle guard 3810 is in its first position, the sheath 3820 is removably coupled to the needle hub 3223. In some embodiments, the recessed portion 3828 and the protrusion 3238 form a seal that is resistant to microbial penetration.

The sheath retainer 3840 has a proximal portion 3842 and a distal portion 3844. The proximal portion 3842 of the sheath retainer 3840 includes a protrusion 3856 that engages a corresponding recess 3526 in the base 3520 (see FIG. 28) to removably couple the sheath retainer 3840 to the base 3520. The distal portion 3844 of the sheath retainer 3840 defines an opening 3846 through which the distal end portion 3824 of the sheath 3820 is disposed. The distal portion 3844 of the sheath retainer 3840 includes a series of retaining tabs 3852 that engage the distal end portion 3824 of the sheath 3820 to couple the sheath 3820 to the sheath retainer 3840. In this manner, when the sheath retainer 3840 is moved distally away from the base 3520 into a second (or removed) position, as shown in FIG. 20, the sheath 3820 is removed from the needle 3412. Moreover, this arrangement allows the sheath 3820 to be disposed about the needle 3412 independently from when the sheath retainer 3840 is coupled to the sheath 3820. As such, the two-piece construction of the needle guard provides flexibility during manufacturing. The distal portion 3844 of the sheath retainer 3840 also includes a protrusion 3848 to aid the user when grasping the needle guard 3810.

Figure 25:
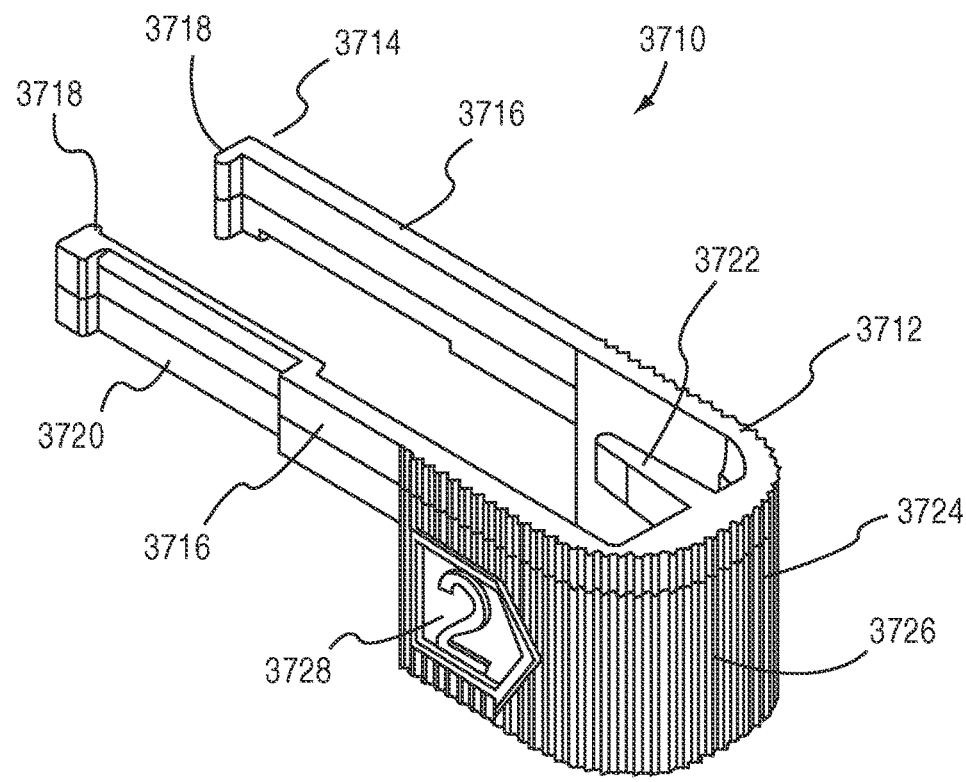
FIG. 25 is a perspective view of a member of the auto-injector illustrated in FIG. 21.

When the needle guard 3810 is in its first position, the sheath retainer 3840 is disposed within a recess 3720 defined by one of the extended portions 3716 of the safety lock 3710 (see FIG. 25). This arrangement prevents the safety lock 3710 from being removed when the needle guard 3810 is in its first position, which in turn, prevents the auto-injector 3002 from being actuated when the needle guard 3810 is in its first position.

The outer surface of the sheath retainer 3840 includes an indicia 3850 to instruct the user in operating the auto-injector 3002. As shown in FIG. 21, the indicia 3850 includes a numeral to indicate the order of operation and an arrow to indicate the direction in which the needle guard 3810 should be moved. In some embodiments, the indicia 3850 can include different colors, detailed instructions or any other suitable indicia to instruct the user. In other embodiments, the indicia 3850 can protrude from the sheath retainer 3840 to aid the user when grasping the needle guard 3810.

In some embodiments, the sheath 3820 can be constructed from any suitable material, such as, for example polypropylene, rubber or any other elastomer. In some embodiments, the sheath 3820 can be constructed from a rigid material to reduce the likelihood of needle sticks during the manufacturing process. In other embodiments, the sheath 3820 can be constructed from a flexible material.

Figure 26:
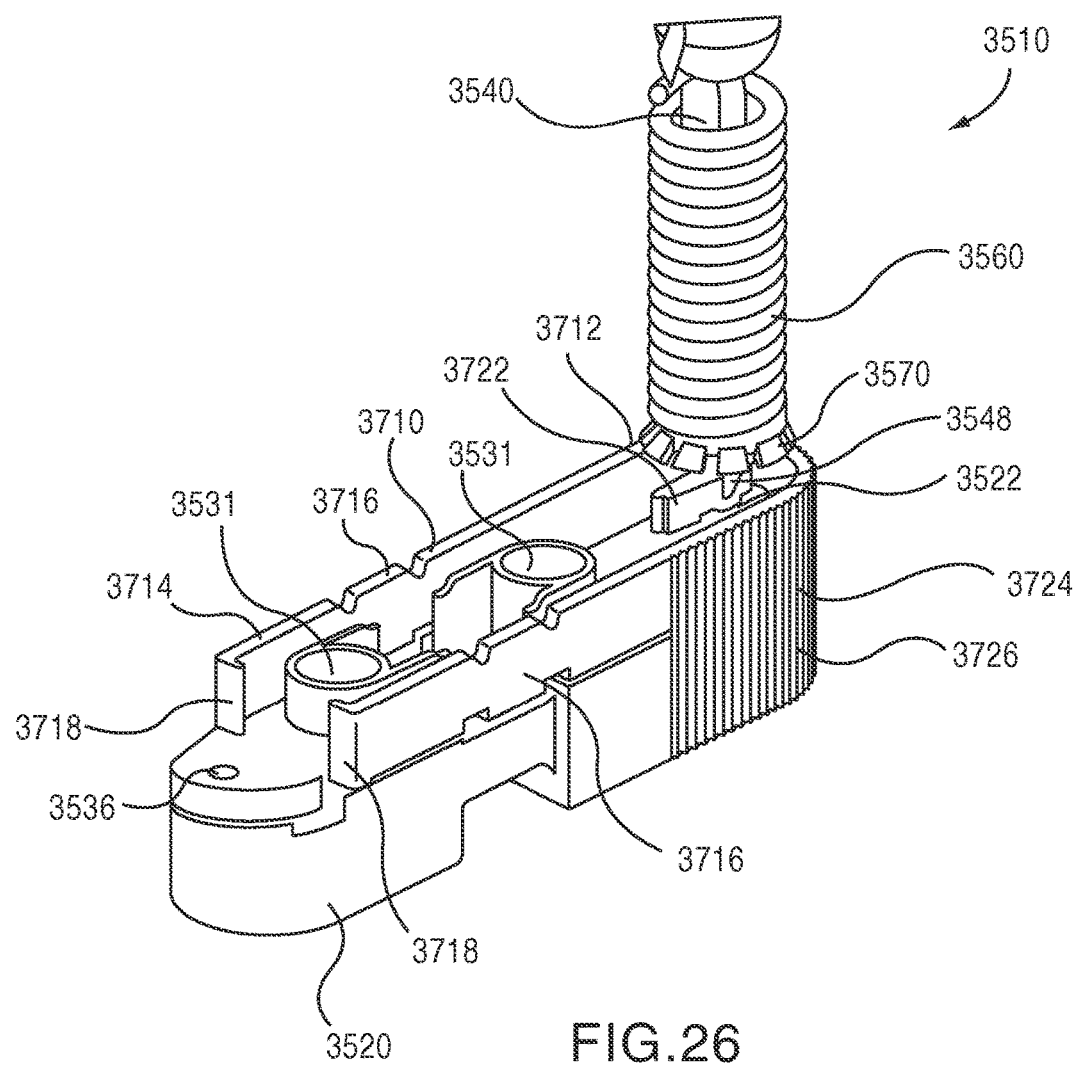
FIG. 26 is a perspective view of a portion of the auto-injector illustrated in FIGS. 17 and 21.

After the needle guard 3810 is removed, the user must then remove the safety lock 3710, as indicated in FIG. 21. As shown in FIG. 25, the safety lock 3710 is a U-shaped member having a first end 3712 and a second end 3714. The second end 3714 of the safety lock 3710 includes two extended portions 3716, each of which includes an inwardly facing protrusion 3718. When the safety lock 3710 is in its first (or locked) position, the extended portions 3716 extend around a portion of the base 3520 to space the base 3520 apart from the distal end portion 3114 of the housing 3110. As shown in FIG. 26, the protrusions 3718 are configured engage a portion of the base 3520 to removably couple the safety lock 3710 in its first position.

One of the extended portions 3716 defines a recess 3720 that receives the sheath retainer 3840 when the needle guard 3810 is in its first position, as discussed above. Although only one extended portion 3716 is shown as including a recess 3720, in some embodiments both extended portions 3716 can include a recess 3720 to receive the sheath retainer 3840. In other embodiments, the safety lock 3710 can be engaged with the needle guard 3810 to prevent movement of the safety lock 3710 when the needle guard 3810 is in place in any suitable manner. For example, in some embodiments, the sheath retainer can include protrusions that are received within corresponding openings defined by the safety lock. In other embodiments, the safety lock can include protrusions that are received within corresponding openings defined by the sheath retainer.

The first end 3712 of the safety lock 3710 includes a locking protrusion 3722 that extends inwardly. As shown in FIG. 26, when the safety lock 3710 is in its first position, the locking protrusion 3722 extends between the projections 3548 of the rod 3540 and obstructs the opening 3522 of the base 3520. In this manner, when the safety lock 3710 is in its first position, the base 3520 cannot be moved proximally to allow the projections 3548 to be received within the opening 3522. The arrangement of the locking protrusion 3722 also prevents the projections 3548 from being moved inwardly towards each other. Accordingly, when the safety lock 3710 is in its first position, the auto-injector 3002 cannot be actuated.

The outer surface 3724 of the first end 3712 of the safety lock 3710 includes a series of ridges 3726 to allow the user to more easily grip the safety lock 3710. The outer surface 3724 of the first end 3712 of the safety lock 3710 also includes an indicia 3728 to instruct the user in operating the auto-injector 3002. As shown in FIG. 25, the indicia 3728 includes a numeral to indicate the order of operation and an arrow to indicate the direction in which the safety lock 3710 should be moved. In some embodiments, the indicia 3728 can include different colors, detailed instructions or any other suitable indicia to instruct the user. In other embodiments, the indicia 3728 can protrude from the safety lock 3710 to aid the user when grasping the safety lock 3710.

Figure 27:
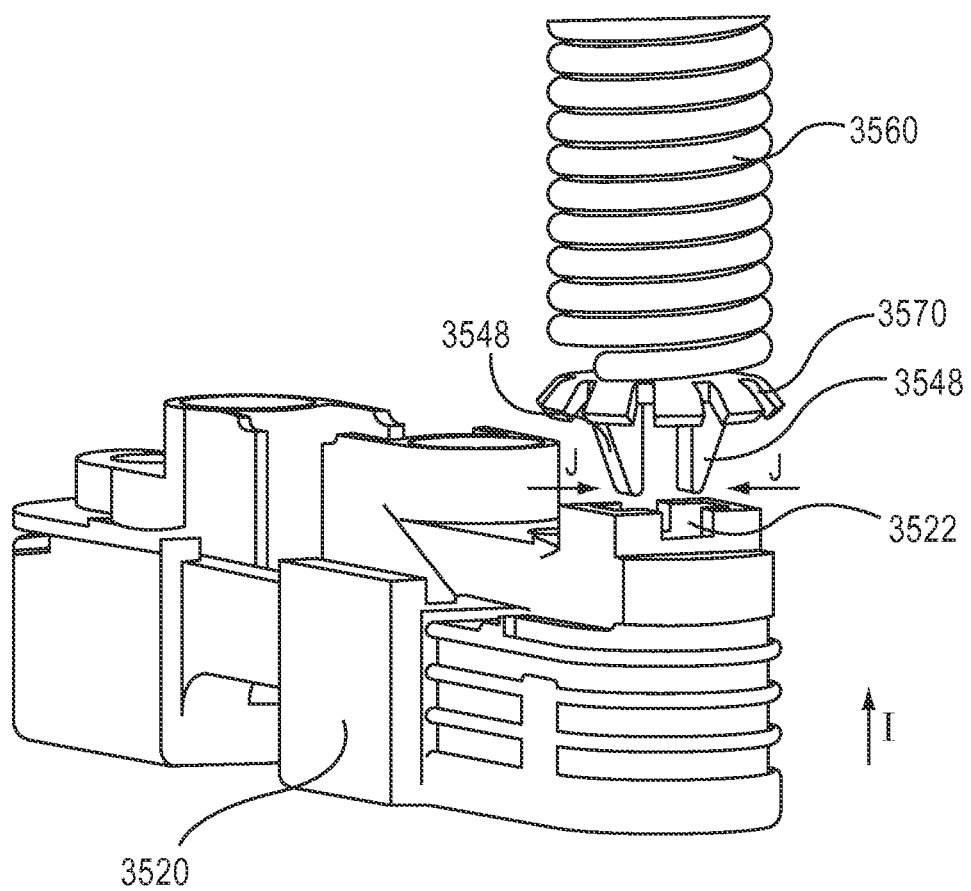
FIG. 27 is a perspective view of a portion of the auto-injector illustrated in FIGS. 17 and 26.
Figure 28:
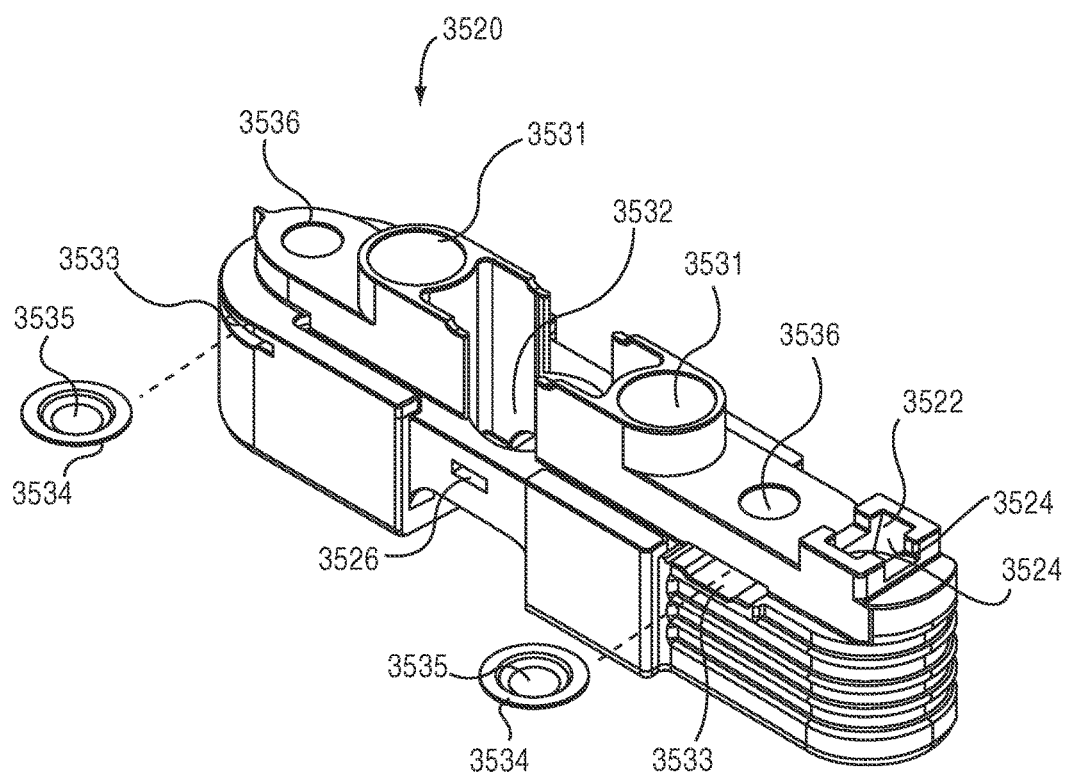
FIG. 28 is a partially exploded perspective view of a base of the auto-injector illustrated in FIG. 26.
Figure 36:
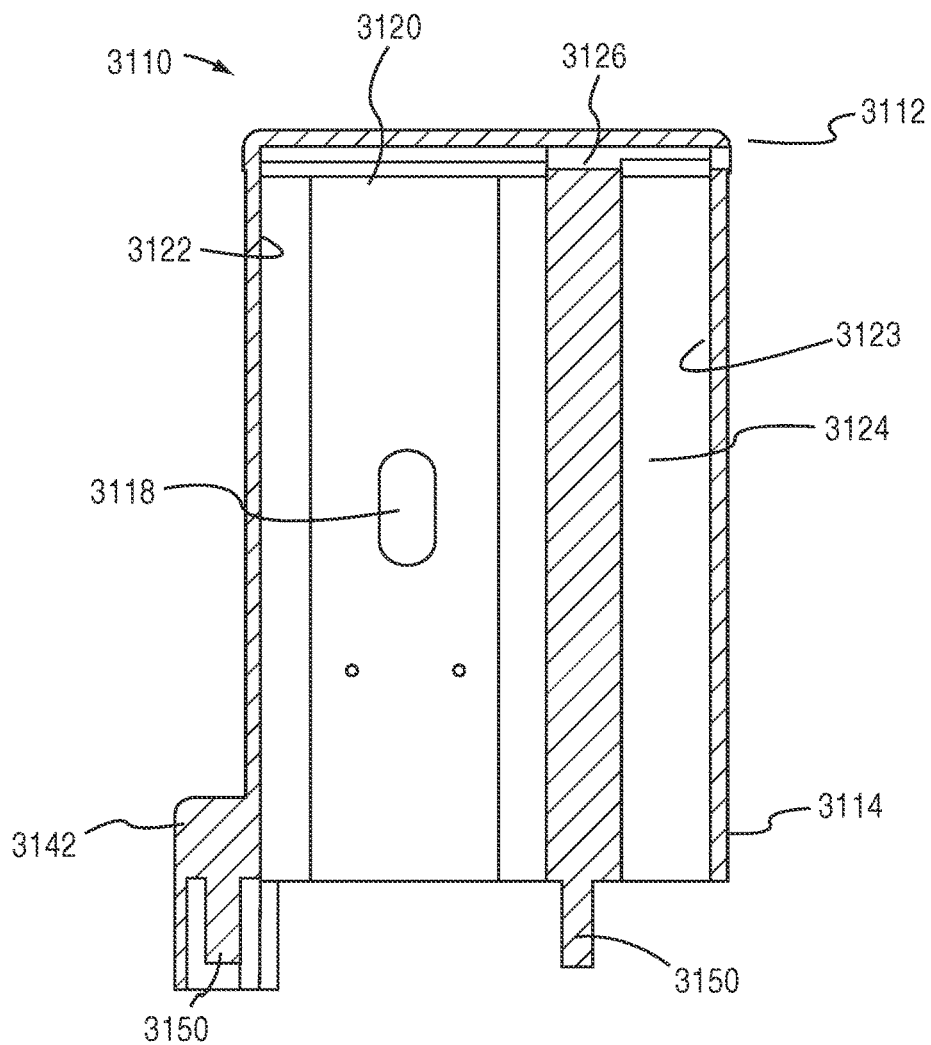
FIG. 36 is a cross-sectional view of the housing taken along line 36-36 in FIG. 35.

After being enabled, the auto-injector 3002 can then be actuated by moving the base 3520 proximally towards the housing 3110, as indicated by arrow I in FIG. 27. As shown in FIGS. 28 and 36, the base 3520 defines two openings 3536 that receive corresponding attachment protrusions 3150 disposed on the distal end portion 3114 of the housing 3110. In this manner, the movement and/or alignment of the base 3520 relative to the housing 3110 is guided by the attachment protrusions 3150 and the openings 3536 (see FIG. 36).

Each attachment protrusion 3150 is secured within its corresponding opening 3536 by a lock washer 3534. The lock washers 3534 each define an opening 3535 that receives a portion of the attachment protrusion 3150. The lock washers 3534 are disposed within slots 3533 defined by the base 3520 so that the openings 3535 are aligned with the attachment protrusions 3150. The openings 3535 are configured to allow the lock washers 3534 to move proximally relative to the attachment protrusions 3150, but to prevent movement of the lock washers 3534 distally relative to the attachment protrusions 3150. In this manner, when the attachment protrusions 3150 are disposed within the openings 3535 of the lock washers 3534, the base 3520 becomes fixedly coupled to the housing 3110. Moreover, after the base 3520 is moved proximally relative to the housing 3110, the lock washers 3534 prevent the base 3520 from returning to its initial position. Said another way, the arrangement of the lock washers 3534 prevents the base 3520 from being "kicked back" after the auto-injector 3002 has been actuated.

The base 3520 also defines a needle opening 3532, a recess 3526 and two retraction spring pockets 3531. The needle opening 3532 receives a portion of the needle guard 3810 when the needle guard is in its first position. Additionally, when the auto-injector is in its third configuration (see FIG. 37), the needle 3212 extends through the needle opening 3532. As described above, the recess 3526 receives the corresponding protrusion 3856 on the sheath retainer 3840 to removably couple the needle guard 3810 to the base 3520. As will be described in more detail herein, the retraction spring pockets 3531 receive a portion of the retraction springs 3350.

As shown in FIG. 28, the base 3520 includes two opposing tapered surfaces 3524 that define an opening 3522 configured to receive a corresponding tapered surface 3550 of the projections 3548 when the base is moved proximally towards the housing 3110. When the projections 3548 are received within the tapered opening 3522, they are moved together as indicated by arrows J in FIG. 27. The inward movement of the projections 3548 causes the rod 3540 to become disengaged from the spring retainer 3570, thereby allowing the rod 3540 to be moved proximally along its longitudinal axis as the spring 3560 expands. A more detailed description of the components included in the system actuator 3510 is provided below with reference to FIGS. 29 and 30.

The system actuator 3510 includes a rod 3540, a spring 3560 disposed about the rod 3540 and a spring retainer 3570. As described in more detail herein, the spring retainer 3570 retains both the spring 3560 and the rod 3540. The spring retainer 3570 includes a first surface 3572, a second surface 3574 and a series of outwardly extending engagement tabs 3576. The spring retainer 3570 is disposed within the gas container opening 3124 defined by the housing 3110 (see FIG. 36) such that the engagement tabs 3576 engage the interior surface 3123 of the housing 3110 to produce an interference fit. In this manner, the spring retainer 3570 is fixedly disposed within the housing 3110.

The rod 3540 has a proximal end portion 3542 and a distal end portion 3544. The distal end portion 3544 of the rod 3540 includes two extensions 3552 disposed apart from each other to define an opening 3554 therebetween. Each extension 3552 includes a projection 3548 having a tapered surface 3550 and an engagement surface 3549. When the rod 3540 is in its first (or engaged) position, the engagement surfaces 3549 engage the second surface 3574 of the spring retainer 3570 to prevent the rod 3540 from moving proximally along its longitudinal axis. As described above, when the base 3520 is moved proximally towards the housing 3110, the tapered surfaces 3550 of the projections 3548 cooperate with the corresponding tapered surfaces 3524 of the base 3520 to move the extensions 3552 inwardly towards each other. The inward motion of the extensions 3552 causes the engagement surfaces 3549 to become disengaged from the second surface 3574 of the spring retainer 3570, thereby allowing the rod 3540 to move between its first position to a second (or actuated) position.

The proximal end portion 3542 of the rod 3540 includes a retention portion 3545 having a first surface 3547 and a second surface 3546. The first surface 3547 of the retention portion 3545 engages the distal portion 3416 of the compressed gas container 3412. The second surface 3546 of the retention portion 3545 engages a proximal end 3562 of the spring 3560. Similarly, the first surface 3572 of the spring retainer 3570 engages a distal end 3564 of the spring 3560. In this manner, when the rod 3540 is in its first position, the spring 3560 can be compressed between the spring retainer 3570 and the retention portion 3545 of the rod 3540. Accordingly, when the rod 3540 is disengaged from the spring retainer 3570, the force imparted by the spring 3560 on the retention portion 3545 of the rod 3540 causes the rod 3540 to move proximally into its second position.

The proximal end portion 3542 of the rod 3540 is coupled to the compressed gas container 3412 by a connector 3580, which is secured to the distal end portion 3416 of the compressed gas container 3412 by a securing member 3588. The connector 3580 includes a proximal end portion 3582 and a distal end portion 3584. The distal end portion 3584 of the connector 3580 is disposed within the opening 3554 defined between the extensions 3552. In this manner, the connector 3580 is retained by the proximal end portion 3542 of the rod 3540. As will be described in more detail, the distal end portion 3584 of the connector 3580 includes locking tabs 3587.

The proximal end portion 3582 of the connector 3580 includes engagement portions 3586 that engage the distal end portion 3416 of the compressed gas container 3412. The engagement portions 3586 are coupled to the compressed gas container 3412 by the securing member 3588, which can be, for example, a shrink wrap, an elastic band or the like. In other embodiments, the engagement portions 3586 can produce an interference fit with the compressed gas container 3412, thereby eliminating the need for a securing member 3588.

Figure 31:
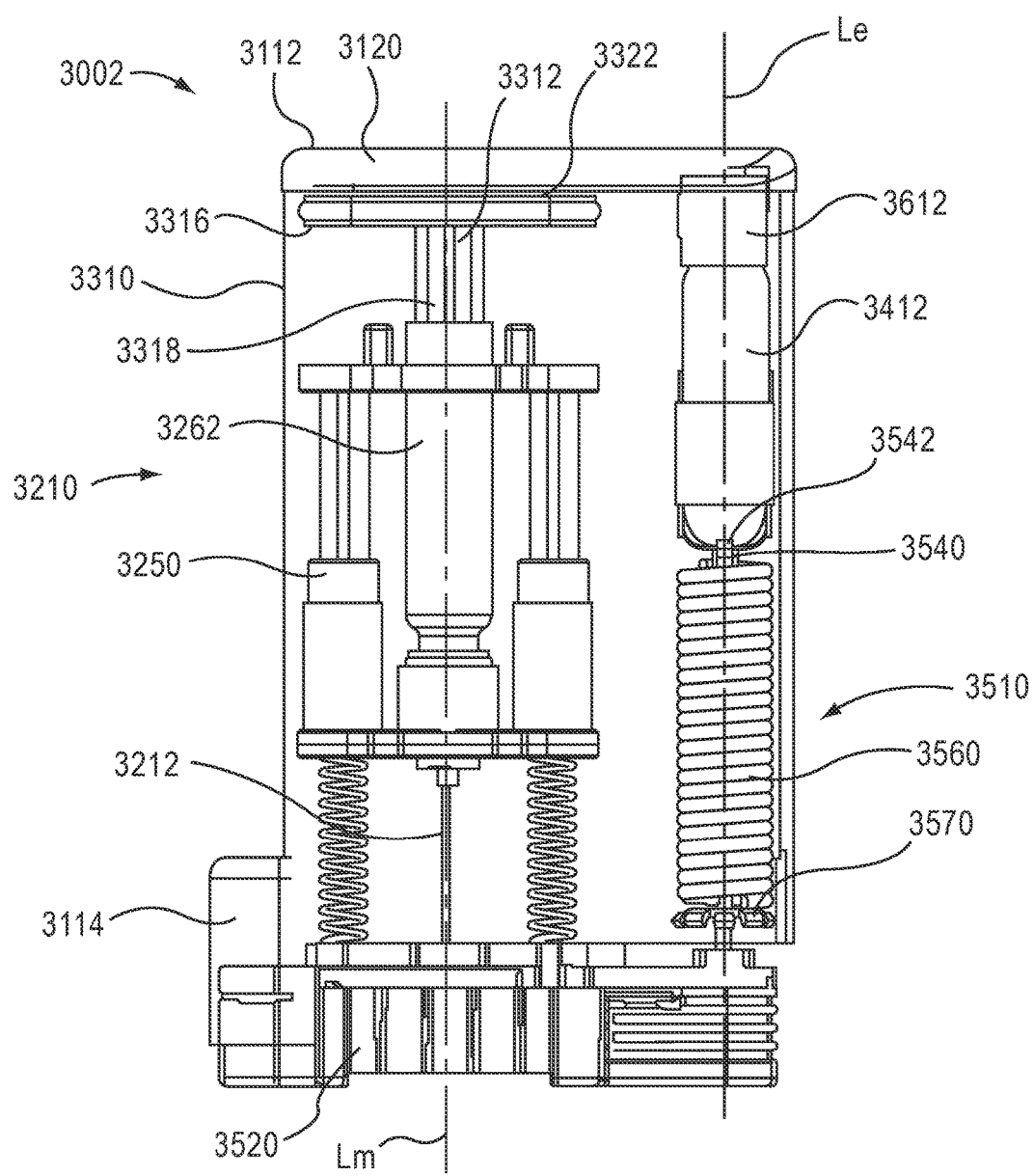
FIG. 31 is a front view of the auto-injector illustrated in FIG. 19 in a second configuration.

Because the rod 3540 is coupled to the compressed gas container 3412, when the rod 3540 is moved from its first (engaged) position to its second (actuated) position, the compressed gas container 3412 is moved proximally within the housing 3110 into engagement with the gas release mechanism 3612. FIG. 31 shows the auto-injector in a second configuration, in which the compressed gas container 3412 is engaged with the gas release mechanism 3612. When in the second configuration, the compressed gas contained within the compressed gas container 3412 is released to actuate the medicament injector 3210. A more detailed description of the gas release process is provided below with reference to FIGS. 32 through 36.

Figure 32:
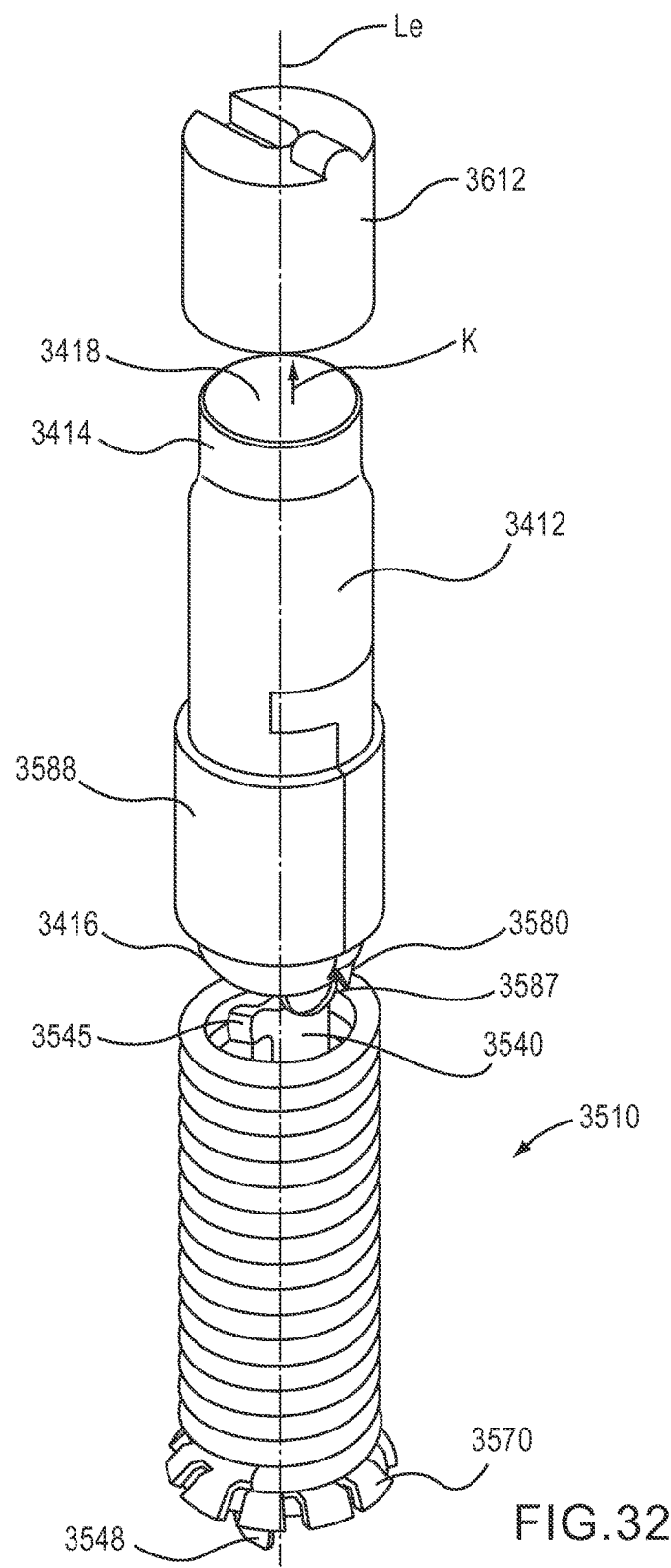
FIG. 32 is a perspective view of a portion of the auto-injector shown in FIG. 31.

FIG. 32 shows an exploded view of the system actuator 3510, the compressed gas container 3412 and the gas release mechanism 3612, each of which are disposed within the gas container opening 3124 defined by the housing 3110 (see FIG. 36). As shown, the compressed gas container 3412, the system actuator 3510 and the gas release mechanism 3612 are arranged substantially coaxial with each other. As previously discussed, when the auto-injector 3002 is actuated, the compressed gas container 3412 is moved proximally within the gas container opening 3124 defined by the housing 3110, as indicated by the arrow K in FIG. 32, until the proximal end 3414 of the compressed gas container 3412 engages the gas release mechanism 3612.

Figure 33:
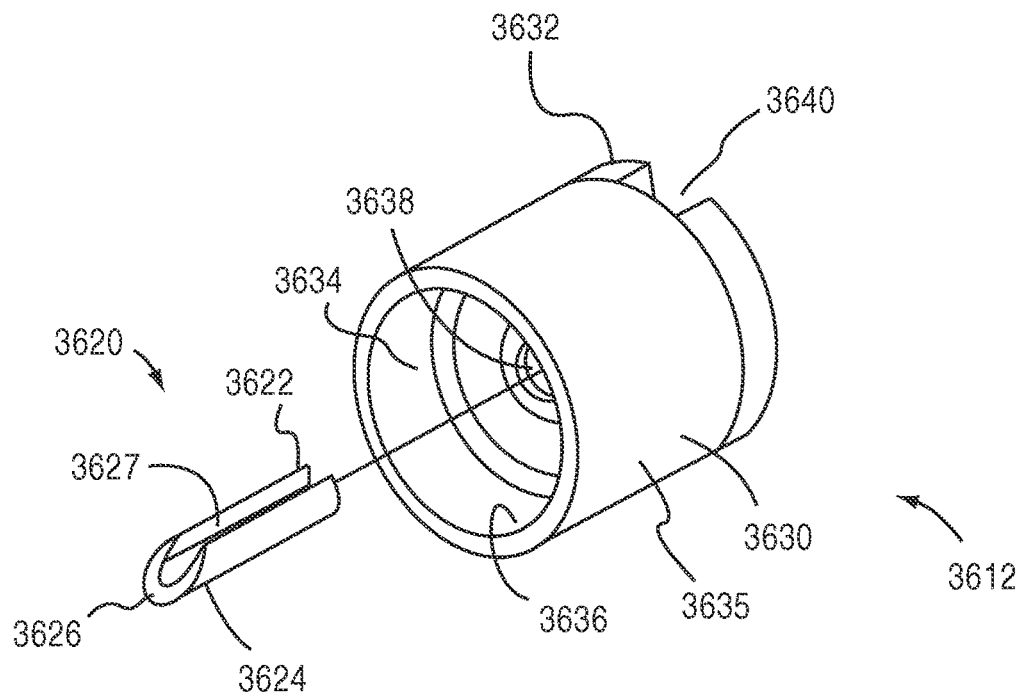
FIGS. 33 and 34 are perspective views of a portion of the auto-injector shown in FIG. 32.
Figure 34:
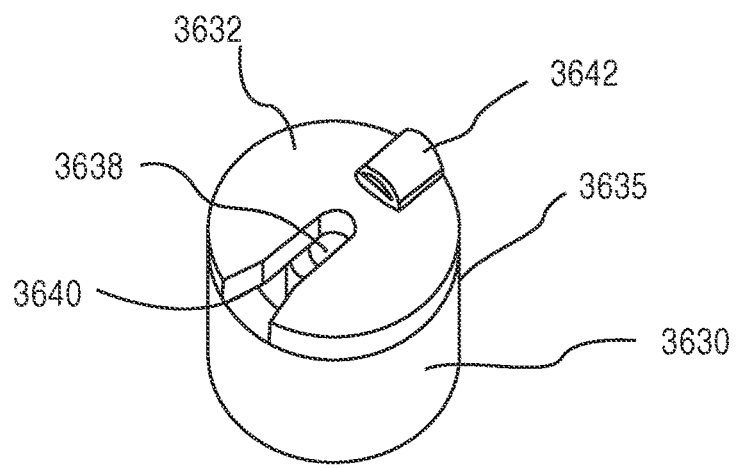
Figure 35:
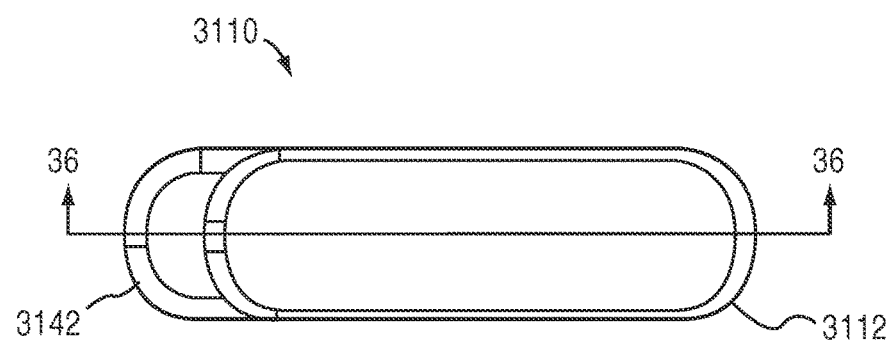
FIG. 35 is a top view of the housing of the auto-injector shown in FIG. 31.

As shown in FIGS. 33 and 34, the gas release mechanism 3612 includes a cap 3630 and a puncturing element 3620 coupled to and disposed within the cap 3630. The puncturing element has a proximal end 3622 and a distal end 3624. The distal end 3624 of the puncturing element 3620 defines a sharp point 3626 configured to puncture the proximal end 3414 of the compressed gas container 3412. The puncturing element 3620 defines an opening 3627 extending from its distal end 3624 to its proximal end 3622.

The cap 3630 has a proximal end 3632, an outer surface 3635 and an inner surface 3636. The inner surface 3636 of the cap 3630 defines an opening 3634 that receives the proximal end 3414 of the compressed gas container 3412 when the auto-injector 3002 is in its second configuration. The proximal end 3632 of the cap 3630 defines an opening 3638 therethrough and a channel 3640 in fluid communication with the opening 3638. The opening 3638 receives the proximal end 3622 of the puncturing element 3620 to couple the puncturing element 3620 to the cap 3630. The puncturing element 3620 is disposed within the cap 3630 such that when the compressed gas container 3412 is moved into the opening 3634, the distal end 3624 of the puncturing element 3620 punctures the proximal end 3414 of the compressed gas container 3412.

The cap 3630 is disposed within the gas container opening 3124 such that the outer surface 3635 of the cap 3630 engages the inner surface 3123 of the housing 3110. In some embodiments, the outer surface 3635 of the cap 3630 can be sized to produce an interference fit with the inner surface 3123 of the housing 3110. In other embodiments, the cap 3630 can be fixedly coupled within the gas container opening 3124 using an adhesive or any other suitable attachment mechanism.

The cap 3630 is oriented within the gas container opening 3124 so that the channel 3640 is aligned with and in fluid communication with the gas passageway 3126 defined by the housing 3110. Moreover, when oriented in this manner, the protrusion 3642 on the proximal end 3632 of the cap 3630 obstructs a portion of the gas passageway 3126, which can be manufactured as a through-hole, to fluidically isolate the gas passageway 3126 from an area outside of the housing 3110. After the proximal end 3414 of the compressed gas container 3412 has been punctured, pressurized gas flows from the compressed gas container 3412 into the gas passageway 3126 through the opening 3627 defined by the puncturing element 3620 and the channel 3640 defined by the proximal end 3632 of the cap 3630.

The inner surface 3636 of the cap 3630 is configured to hermetically seal the proximal end 3414 of the compressed gas container 3412 within the opening 3638. This arrangement prevents pressurized gas from leaking around the compressed gas container 3412 to an area outside of the housing 3110 after the proximal end 3414 of the compressed gas container 3412 has been punctured. In some embodiments, the inner surface 3636 is sized to produce an interference fit with the compressed gas container 3412. In other embodiments, the cap 3630 includes a separate sealing member, such as, for example, an o-ring, to seal the proximal end 3414 of the compressed gas container 3412 within the opening 3638.

Figure 29:
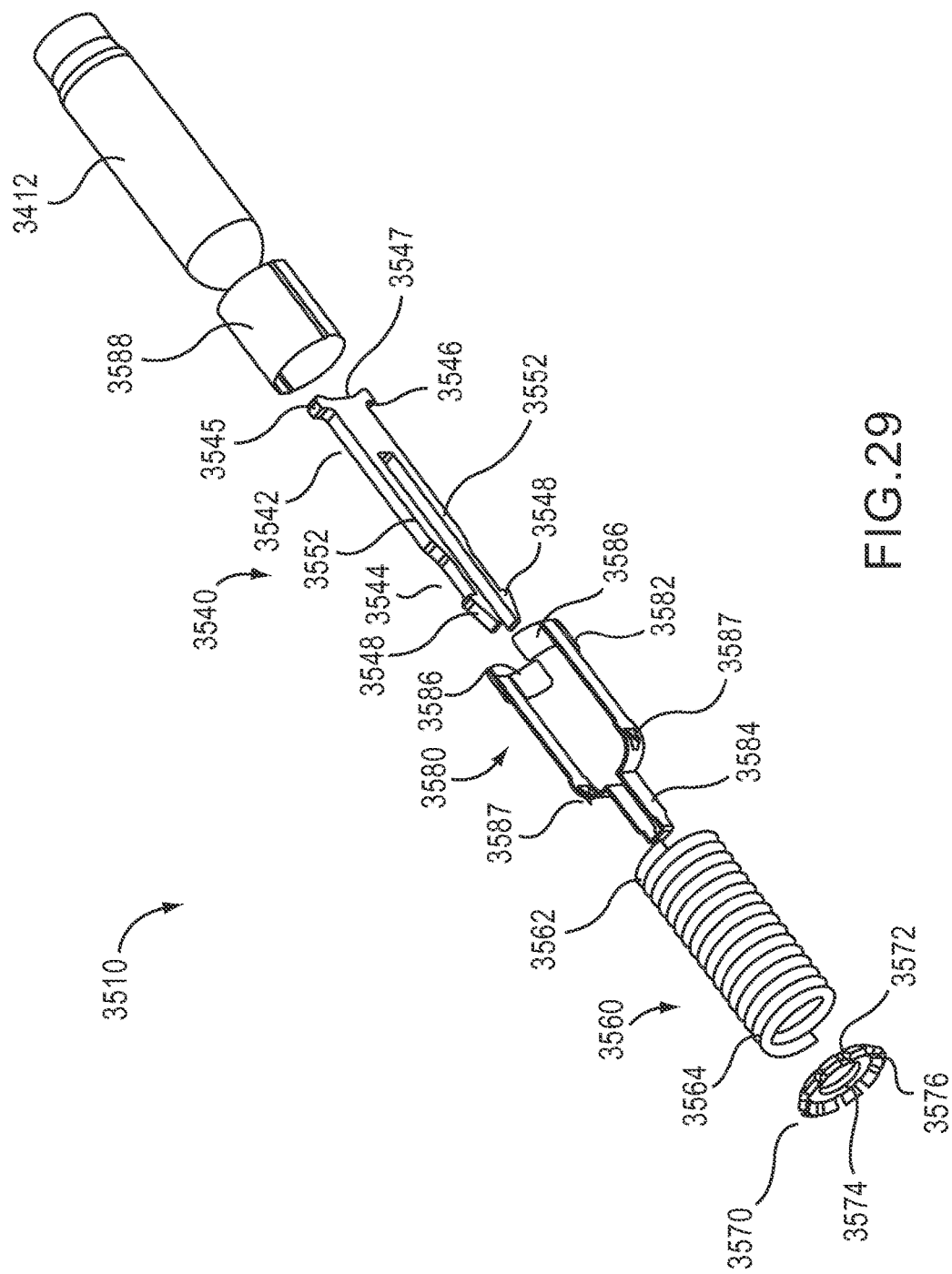
FIG. 29 is an exploded perspective view of a portion of the auto-injector shown in FIG. 21.
Figure 30:
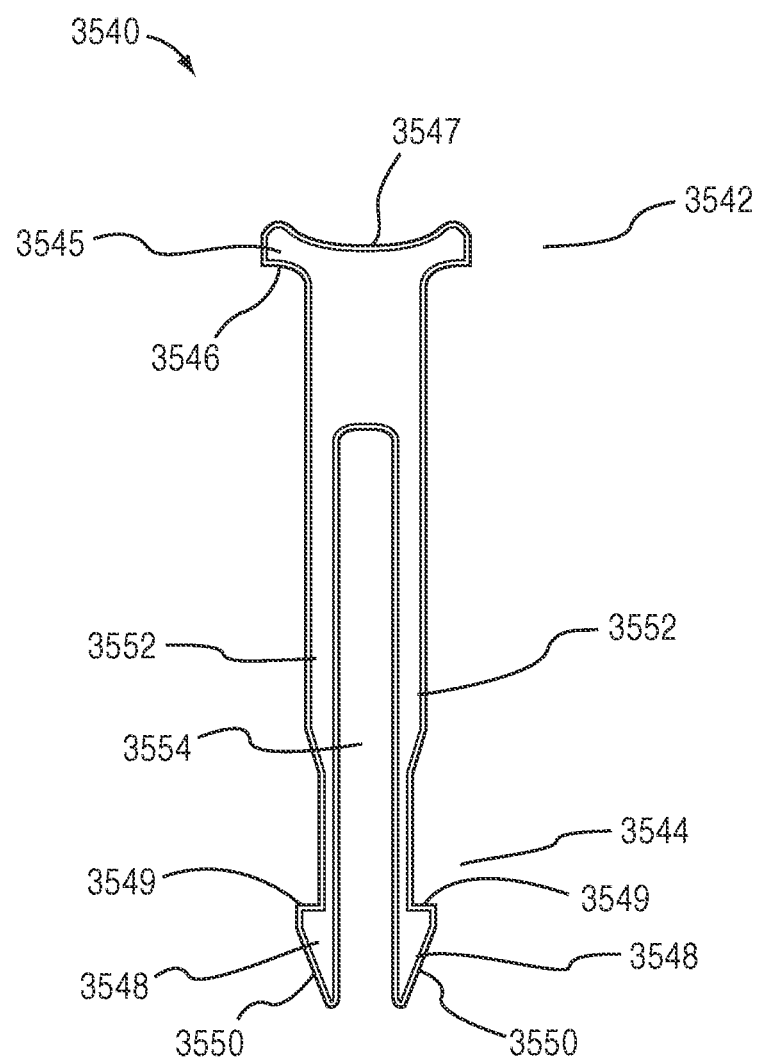
FIG. 30 is a front view of a component of the auto-injector shown in FIG. 29.

After the compressed gas container 3412 is moved into engagement with the gas release mechanism 3612, the position of the compressed gas container 3412 within the gas container opening 3124 is maintained by the locking tabs 3587 on the connector 3580. As shown in FIG. 29, each locking tab 3587 includes a pointed portion that is angled outwardly from the connector 3580. This arrangement allows the connector 3580 to move proximally within the gas container opening 3124 of the housing 3110, but prevents the connector 3580 from moving distally within the gas container opening 3124 of the housing 3110. Said another way, the arrangement of the locking tabs 3587 prevents the compressed gas container 3412 from being "kicked back" when exposed to the force produced by the pressurized gas as the pressurized gas is released.

Figure 37:
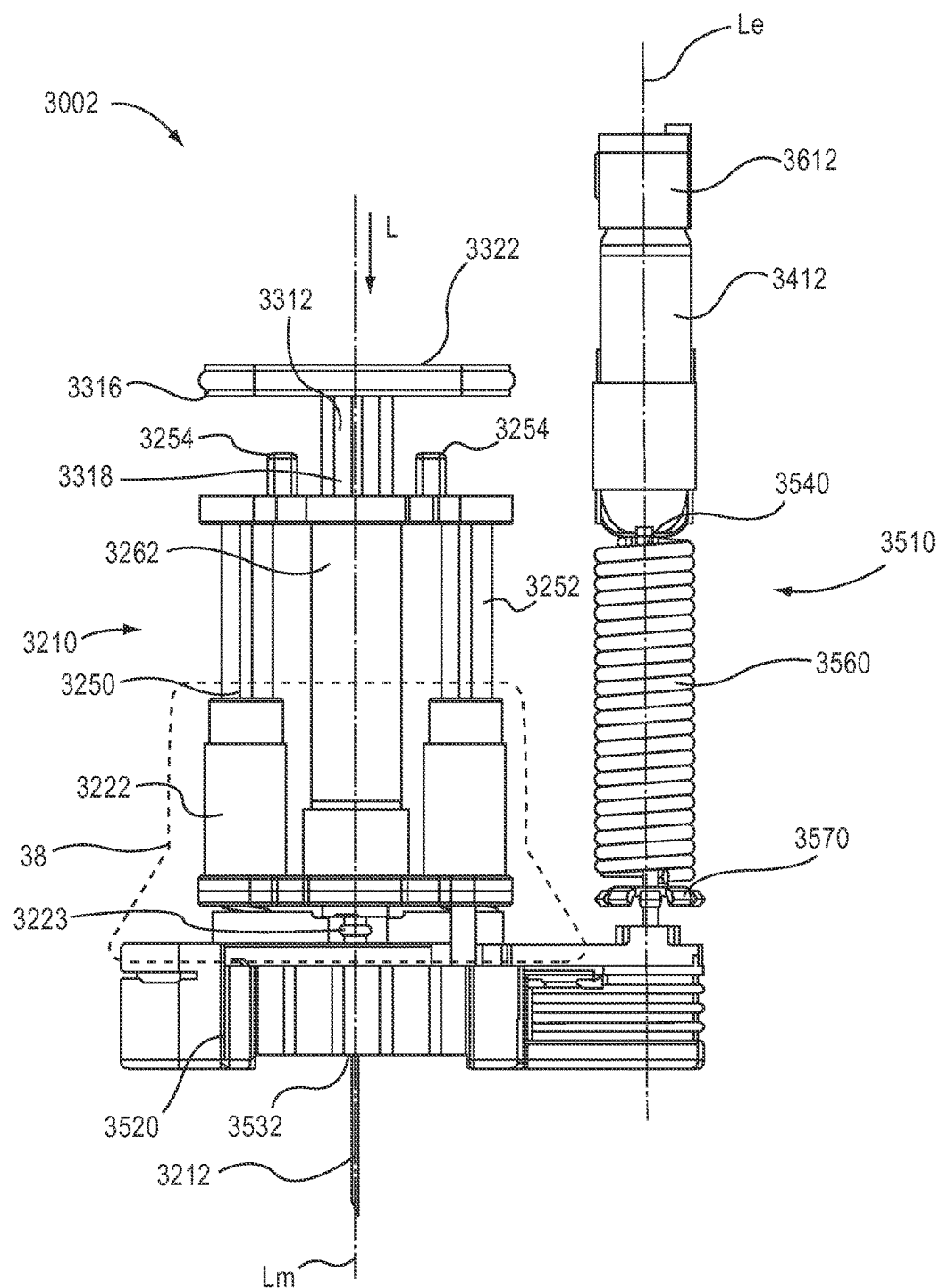
FIG. 37 is front view of the auto-injector illustrated in FIGS. 19 and 31 in a third configuration.
Figure 38:
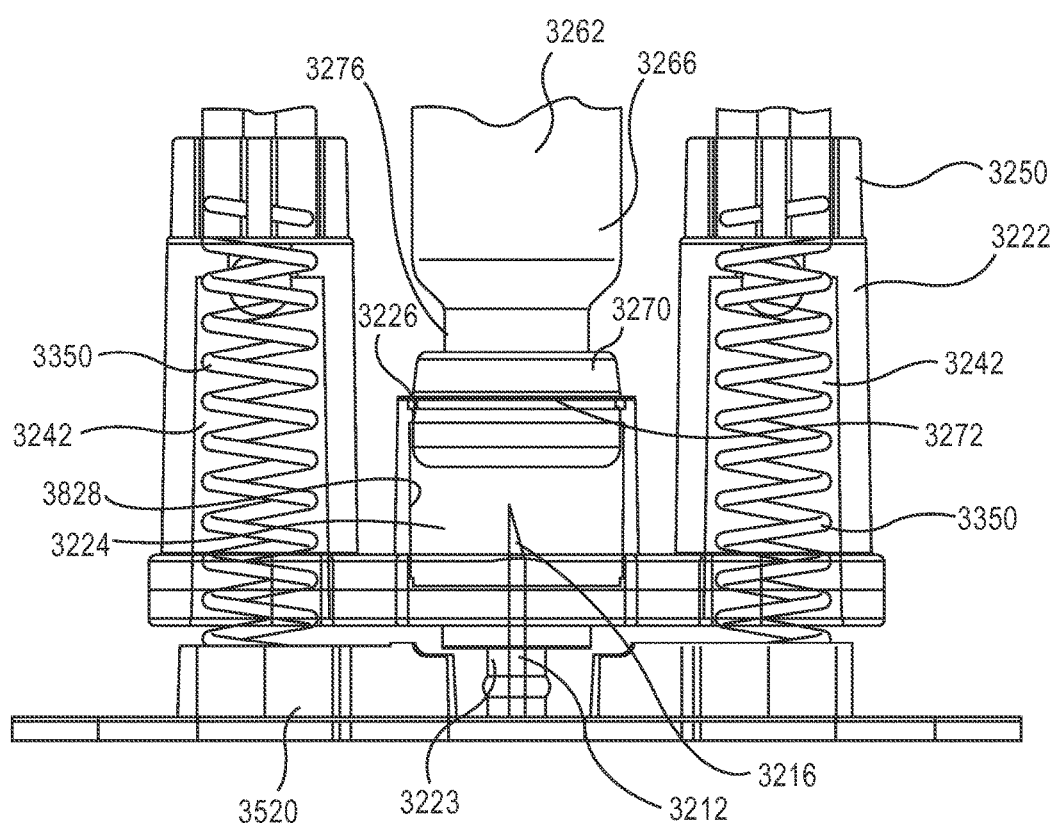
FIG. 38 is a front view of the portion of the auto-injector labeled as 38 in FIG. 37.

As previously discussed, the pressurized gas released from the compressed gas container 3412 produces a force on the boundary of the gas chamber 3120, including the surface 3322 of the movable member 3312. This force causes the movable member 3312 and the medicament injector 3210 move together distally within the housing 3110, as shown by arrow L, placing the auto-injector 3002 in a third configuration, as shown in FIG. 37. When in the third configuration, the distal end 3214 of the needle 3212 is disposed through the opening 3532 defined by the base 3520 to an area outside of the auto-injector 3002. Moreover, as shown in FIG. 38, when the auto-injector 3002 is in the third configuration, the proximal end 3216 of the needle 3212 remains spaced apart from the distal end 3266 of the medicament container 3210, ensuring that the needle 3212 remains fluidically isolated from the medicament container 3210. In this manner, the needle 3212 can be inserted into a patient as the auto-injector 3002 moves between its second configuration (FIG. 31) and its third configuration (FIG. 37) without injecting the medicament until after insertion is completed. A more detailed description of the medicament injector 3210 and the movable member 3312 is provided below with reference to FIGS. 37 through 42.

Figure 39:
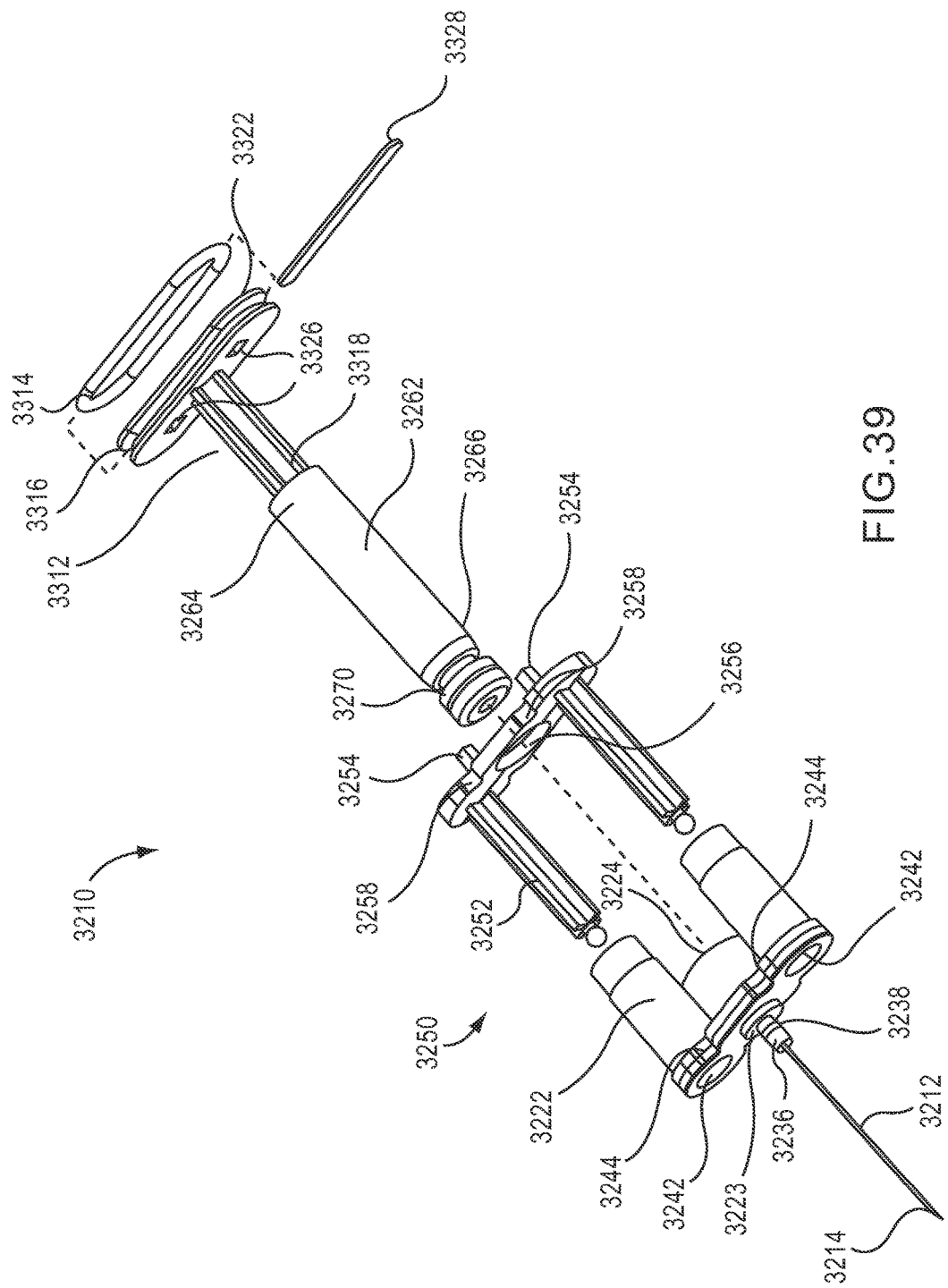
FIG. 39 is a perspective view of a portion of the auto-injector shown in FIG. 37.
Figure 40:
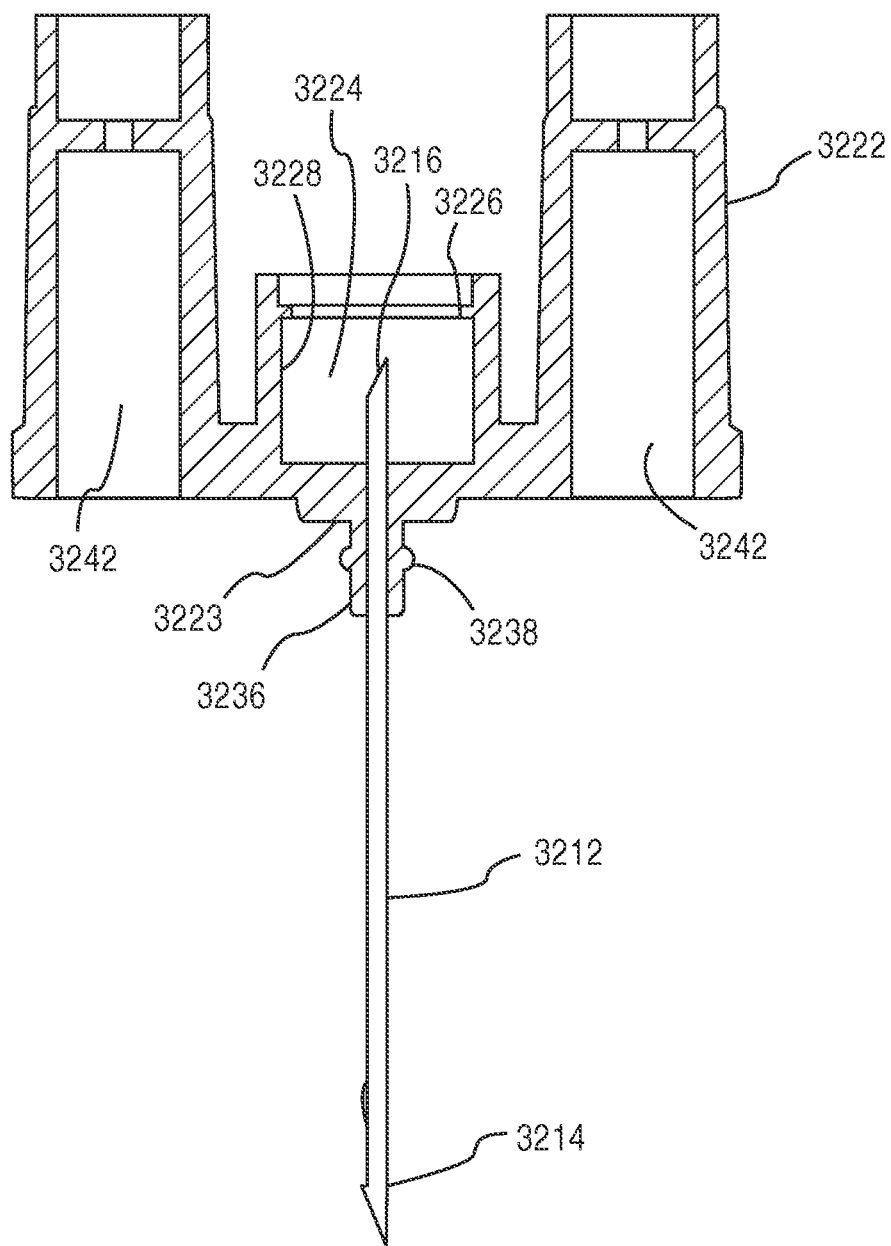
FIG. 40 is a cross-sectional view of a portion of the auto-injector as shown in FIG. 37.

As previously described, the medicament injector 3210 includes a carrier 3250, a medicament container 3262 and a needle 3212. The carrier 3250 has a lower portion 3222 and an upper portion 3252. The lower portion 3222 of the carrier 3250 includes a needle hub 3223, which contains the needle 3212. The lower portion 3222 of the carrier 3250 also defines an opening 3224 configured to receive a distal portion 3266 the medicament container 3262. As shown in FIG. 39, the needle 3212 is coupled to the needle hub 3223 such that the proximal end 3216 of the needle 3212 is disposed within the opening 3224 and the distal end 3214 of the needle 3212 extends distally outside of the needle hub 3223.

The inner surface 3228 of the lower portion 3222 defining the opening 3224 includes a protrusion 3226. The protrusion 3226 is configured to engage a corresponding recess 3272 defined by a sealing cap 3270 disposed at the distal portion 3266 of the medicament container 3262 (see FIG. 42) to secure the medicament container 3262 within the opening 3224 such that the proximal end 3216 of the needle 3212 is spaced apart from the distal end 3266 of the medicament container 3210. The protrusion 3226 and the recess 3272 are configured such that the protrusion 3226 will become disengaged from the recess 3272 when the force applied exceeds a predetermined value. Said another way, the protrusion 3226 and the recess 3272 collectively form a removable snap-fit that allows the medicament container 3262 to be moved within the opening 3224 when the force applied to the medicament container 3262 exceeds a predetermined value. This arrangement ensures that the needle 3212 remains fluidically isolated from the medicament container 3262 during the insertion operation.

Figure 23:
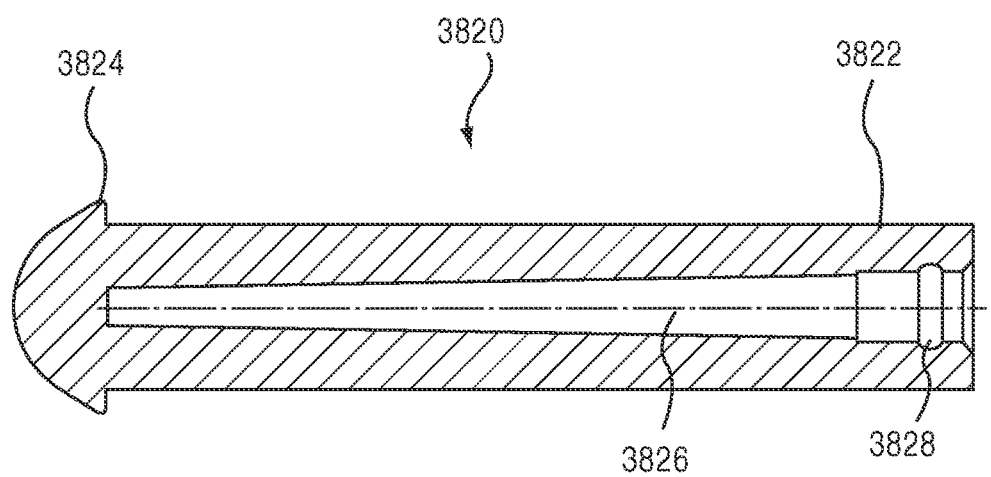
FIG. 23 is a cross-sectional view of a component illustrated in FIG. 21.
Figure 24:
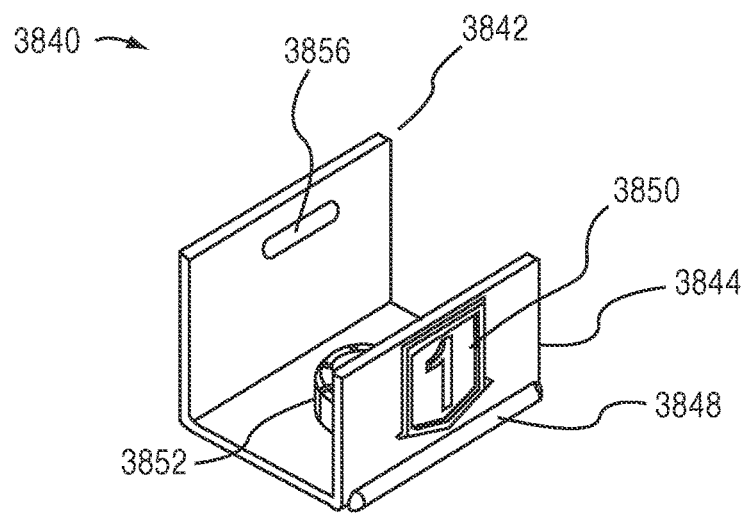
FIG. 24 is a perspective view of a component illustrated in FIG. 21.

The outer surface 3236 of the lower portion 3222 includes a protrusion 3238. As previously described, the protrusion 3238 is configured to engage a corresponding recess portion 3828 within the opening 3826 of the sheath 3820 (see FIG. 23) to removably couple the sheath 3820 to the needle hub 3223.

The lower portion 3222 of the carrier 3250 also defines two retraction spring pockets 3242 each receiving the proximal end 3352 of a retraction spring 3350. As previously discussed, the distal end 3354 of each retraction spring 3350 is retained within the retraction spring pockets 3531 defined by the base 3520. As shown in FIG. 38, when the carrier 3250 moves distally within the housing 3110, the retraction springs 3350 are compressed and therefore bias the carrier 3250 towards the proximal portion 3112 of the housing 3110.

The upper portion 3252 of the carrier 3250 defines an opening 3256 configured to receive a proximal portion 3264 of the medicament container 3262 and includes two valve actuators 3254. As described in more detail herein, the valve actuators 3254 are configured to engage a gas relief valve 3328 to allow the pressurized gas contained within the gas chamber 3120 to escape when the injection event is complete.

The upper portion 3252 of the carrier 3250 defines four gas relief passageways 3258. Similarly, the lower portion 3222 of the carrier 3250 defines four gas relief passageways 3244. When the pressurized gas is released from the gas chamber 3120, the gas relief passageways 3258, 3244 provide a fluid path to allow the pressurized gas to flow from the gas chamber 3120 to an area outside of the housing 3110.

Figure 42:
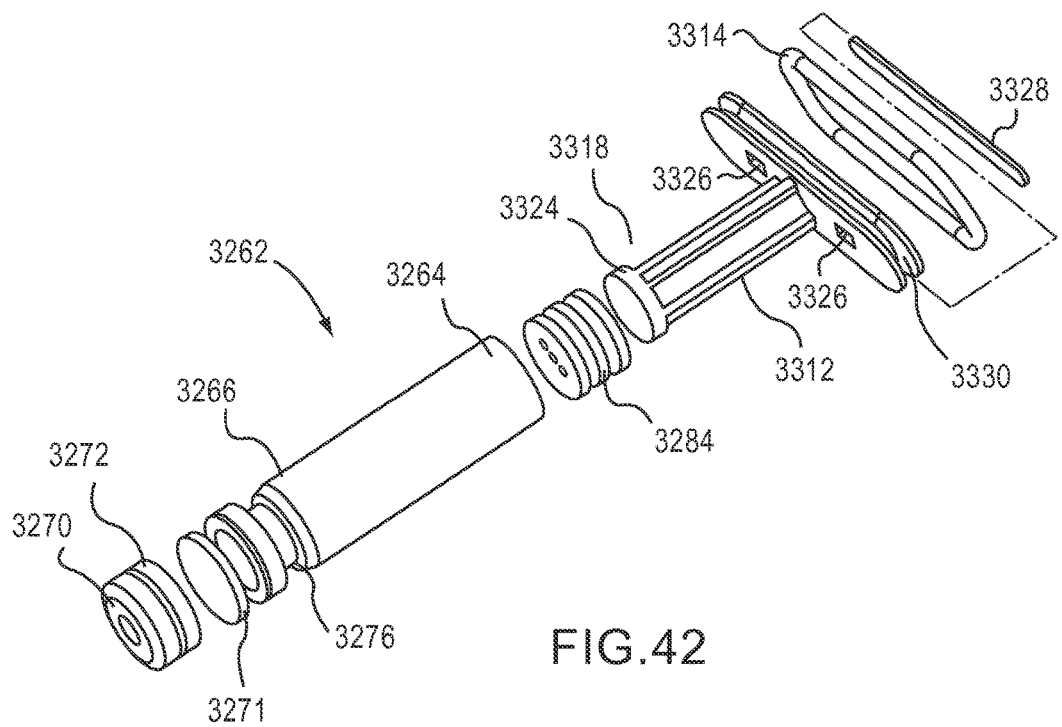
FIG. 42 is an exploded perspective view of a portion the auto-injector as shown in FIG. 37.

As described above, the movable member 3312 includes a proximal end portion 3316 and a distal end portion 3318. The distal end portion 3318 includes a piston 3324 disposed within the proximal portion 3264 of the medicament container 3262, such that the piston engages a plunger 3284 contained within the medicament container 3262, as shown in FIG. 42.

Figure 41:
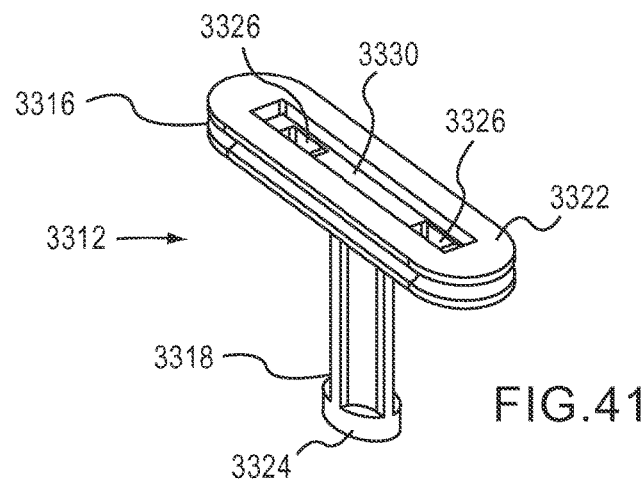
FIG. 41 is a perspective view of a portion of the auto-injector as shown in FIG. 37.

The proximal end portion 3316 includes a surface 3322 that defines a portion of a boundary of the gas chamber 3120. As shown in FIG. 41, the proximal end portion 3316 defines two openings 3326 therethrough, each of which are in fluid communication between the gas chamber 3120 and the interior of the housing 3110 outside the gas chamber 3120. The proximal end portion 3316 further defines a slot 3330 that receives a gas relief valve 3328, which can be, for example, a flexible rubber member. The gas relief valve 3328 is positioned within the slot 3330 and adjacent the openings 3326 to selectively allow fluid communication between the gas chamber 3120 and the area outside the gas chamber 3120 through the openings 3326. The operation of the gas relief valve 3328 is discussed in more detail herein.

The proximal end portion 3316 of the movable member 3312 also includes a seal 3314 that engages a portion the inner surface 3122 of the housing 3110 (see FIG. 36) to fluidically isolate the gas chamber 3120. Although the seal 3314 is shown as being an o-ring seal, in some embodiments, the seal need not be a separate component, but can rather be a portion of the proximal end portion 3316 of the movable member 3312.

Figure 43:
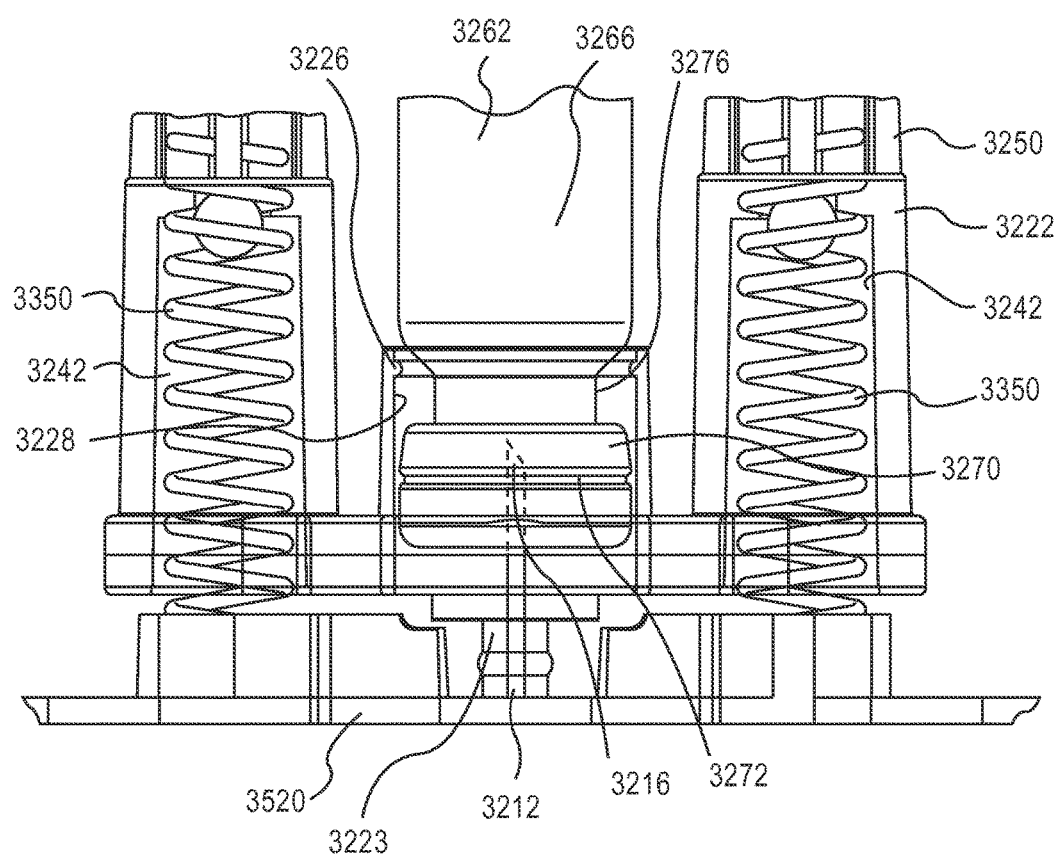
FIG. 43 is front view of the auto-injector illustrated in FIGS. 19, 31 and 38 in a fourth configuration.

When the needle insertion operation is completed, the lower portion 3222 of the carrier 3250 engages the base 3520, preventing further distal movement of the carrier 3250 within the housing. Because the distal motion of the carrier 3250 is opposed, the force exerted by the pressurized gas on the surface 3322 of the movable member 3312 increases until the protrusion 3226 of the lower portion 3222 of the carrier 3250 and the recess 3272 defined by sealing cap 3270 of the medicament container 3262 become disengaged. Accordingly, the medicament container 3262 to moves distally relative to the carrier 3250, placing the auto-injector 3002 in a fourth configuration, as shown in FIG. 43. When moving between the third configuration (FIG. 38) and the fourth configuration (FIG. 43), the proximal end 3216 of the needle 3212 pierces the sealing cap 3270 and the liner 3271 disposed at the distal portion 3266 of the medicament container 3262. As such, when in the fourth configuration, the proximal end 3216 of the needle 3212 is in fluid communication with the medicament container 3262, thereby allowing the medicament to be injected.

Figure 44:
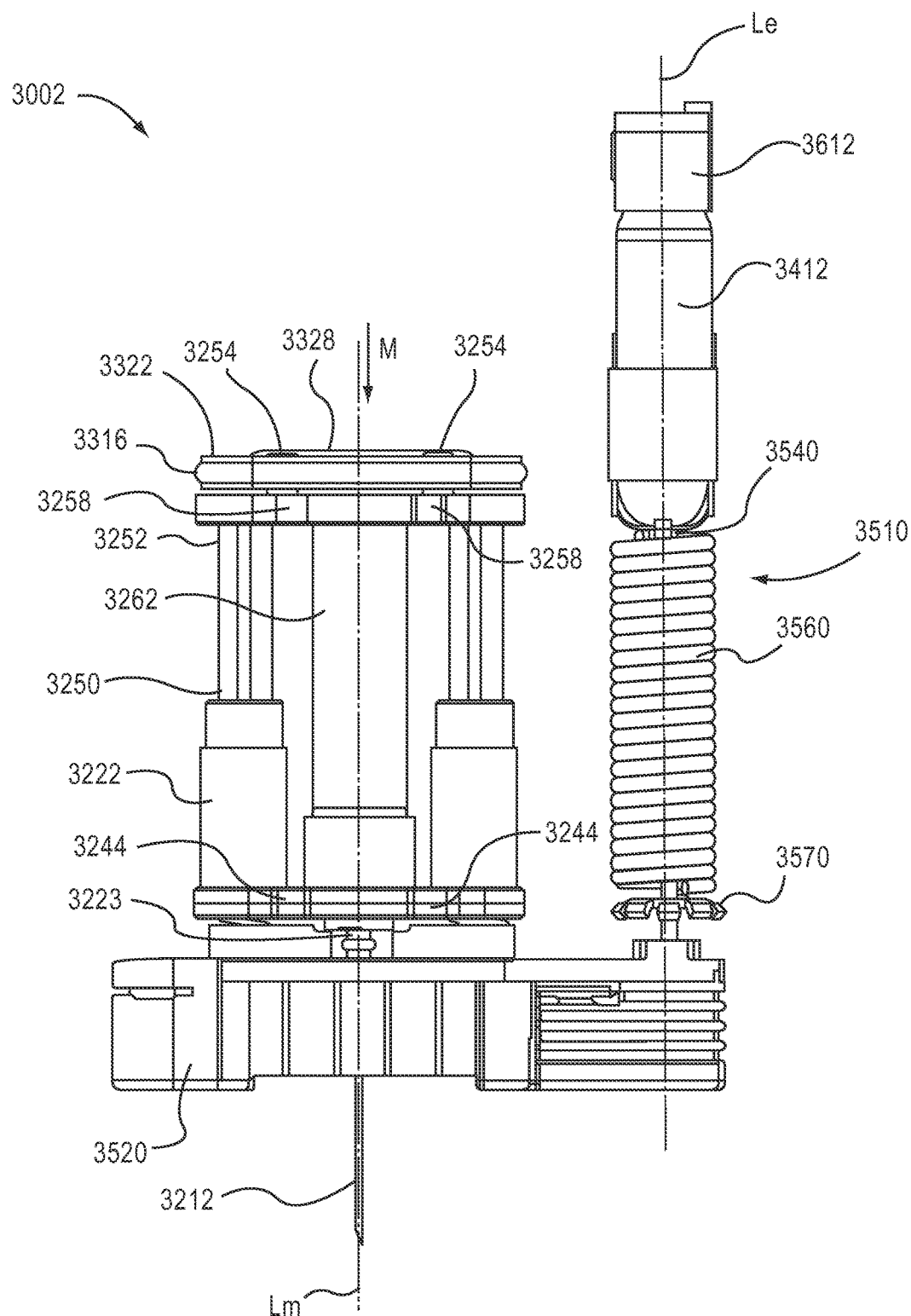
FIG. 44 is a front view of a portion of the auto-injector illustrated in FIGS. 19, 31, 38 and 43 in a fifth configuration.

Once the needle 3212 is in fluid communication with the medicament container 3262, the force from the pressurized gas causes the piston 3324 of the movable member 3312 to move the plunger 3284 within the medicament container 3262, as shown by arrow M, thereby expelling the medicament through the needle 3212. The piston 3324 and the plunger 3284 move a predetermined distance within the medicament container 3262, placing the auto-injector 3002 in a fifth configuration, as shown in FIG. 44. When the auto-injector 3002 is in the fifth configuration, the injection of medicament is complete.

When the auto-injector 3002 is in its fifth configuration, proximal portion 3316 of the movable member 3312 is in contact with the upper portion 3252 of the carrier 3250, thereby preventing further movement of the piston 3324 within the medicament container 3262. In this manner, the distance through which the piston 3324 travels, and therefore the amount of medicament injected, can be controlled.

Additionally, when the auto-injector 3002 is in its fifth configuration, the valve actuators 3254 are disposed within the openings 3326 such that the valve actuators 3254 displace the gas relief valve 3328. Accordingly, the pressurized gas contained within the gas chamber 3120 can flow from the gas chamber 3120 to the area within the housing 3310 outside of the gas chamber 3310. As previously discussed, the gas relief passageways 3258, 3244 provide a fluid path to allow the pressurized gas to flow from the gas chamber 3120, through the opening 3532 defined by the base 3520 and to an area outside of the housing 3110.

Figure 45:
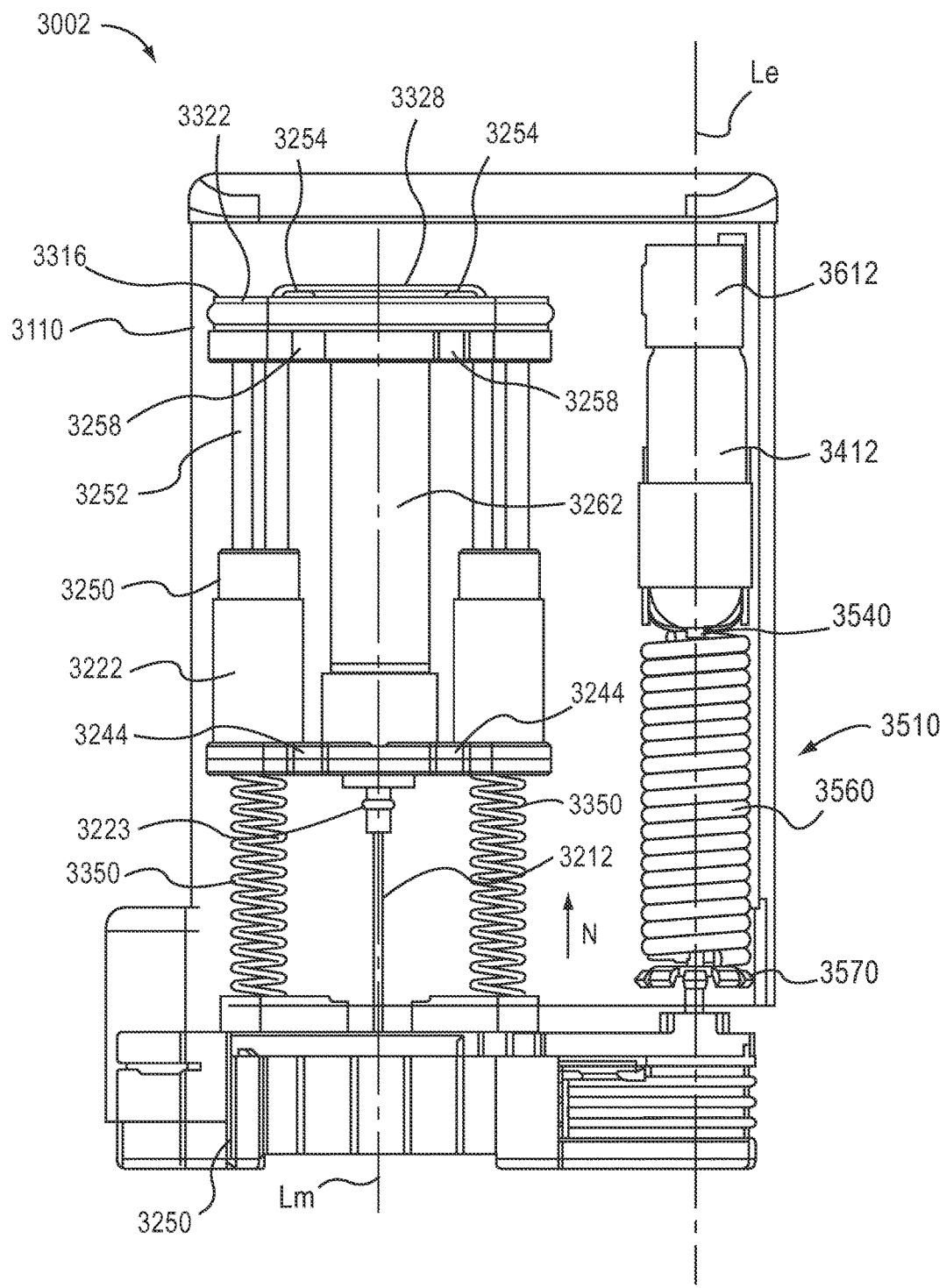
FIG. 45 is a front view of the auto-injector illustrated in FIGS. 19, 31, 38, 43 and 44 in a sixth configuration.

When the pressurized gas flows out of the gas chamber 3120, the pressure exerted on the surface 3322 of the movable member 3312 decreases. Accordingly, the force exerted by the retraction springs 3350 is sufficient to move the medicament injector 3210 and the movable member 3312 proximally within the housing 3110, as shown by arrow N, into a sixth (or retracted) configuration as shown in FIG. 45. Because the medicament injector 3210 and the movable member 3312 move together, the valve actuators 3254 remain disposed within the openings 3326 as the auto-injector 3002 moves into the sixth configuration. In this manner, the gas relief valve 3328 remains displaced and the openings 3326 remain in fluid communication with the gas chamber 3120 and the area within the housing 3310 outside of the gas chamber 3310 independent of the position of the movable member 3312. Such an arrangement ensures that all of the pressurized gas flows out of the gas chamber 3120, thereby ensuring that the medicament injector 3210 and the movable member 3312 return to the sixth configuration and do not oscillate between the sixth configuration and the fifth configuration, which could lead to the needle 3212 not being fully retracted into the housing 3110.

Although the auto-injector 3002 has been shown and described having a housing 3110 having a substantially rectangular shape, in some embodiments, an auto-injector can have a housing having any shape. In some embodiments, for example, an auto-injector can have a substantially cylindrical shape. In other embodiments, for example, the auto-injector can have an irregular and/or asymmetrical shape.

Certain components of the auto-injector 3002 are shown and described as being coupled together via protrusions and mating recesses. The protrusions and/or recesses can be disposed on any of the components to be coupled together and need not be limited to only a certain component. For example, the base 3520 is shown as defining two openings 3536 that receive corresponding attachment protrusions 3150 on the distal end portion 3114 of the housing 3110. In some embodiments, however, the protrusions can be disposed on the base and the mating recesses can be defined by the distal end portion of the housing. In other embodiments, two or more components can be coupled together in any suitable way, which need not include protrusions and mating recesses. For example, in some embodiments, two or more components can be coupled together via mating shoulders, clips, adhesive and the like.

Similarly, although certain components of the auto-injector 3002 are shown and described as being constructed from multiple separate components, in some embodiments, such components can be monolithically constructed. For example, the carrier 3250 is shown and described as including an upper portion 3252 and a lower portion 3222 that are constructed separately and then coupled together. In other embodiments, a carrier can be constructed monolithically.

Although the base 3520 of the auto-injector 3002 has been shown and described covering almost the entire distal end portion 3114 of the housing 3110, in some embodiments, a base configured to actuate the auto-injector can be disposed about only a portion of the distal end of the housing. For example, in some embodiments, an auto-injector can include a button extending from the distal end portion of the housing configured to engage and release the system actuator.

Although the rod 3540 is shown and described as being an elongated member that is released by being elastically deformed, in some embodiments, a rod can be of any suitable shape and in any suitable orientation within the housing. Moreover, in some embodiments, a rod can be released by being plastically deformed. For example, in some embodiments, a rod can be disposed along an axis that is offset from the longitudinal axis of the energy storage member. In some embodiments, the rod can be configured to break upon actuation.

Although the gas release mechanism 3612 is shown and described as including a puncturing element 3620 to puncture a portion of the compressed gas container 3262, the gas release mechanism 3612 need not include a puncturing element 3620. For example, in some embodiments, the gas release mechanism can include an actuator configured to actuate a valve that controls the flow of gas out of the compressed gas container. For example, in some embodiments, a compressed gas container can include a spring loaded check ball and the gas release mechanism can include an actuator configured to engage and depress the check ball to release pressurized gas from the compressed gas container.

Although the auto-injector 3002 is shown and described as having six different configurations that are different from each other, in some embodiments, certain configuration of an auto-injector can be the same as another configuration. For example, in some embodiments, a "pre-actuation configuration can be the same as a "retracted" configuration. In other embodiments, any of the functions described above can be accomplished when an auto-injector is moved between any number of different configurations.

Although the compressed gas container 3412 is shown and described above as a single-use compressed gas container disposed within the housing 3110, in some embodiments, a compressed gas container can be a multi-use container. Moreover, the compressed gas container need not be contained within the housing. For example, in some embodiments, the compressed gas container can be a container disposed outside of the housing. Additionally, the compressed gas container can be any source of pressurized gas. For example, in some embodiments, the compressed gas source can be a container having two or more chemicals formulated to produce a pressurized gas when mixed. In other embodiments, the compressed gas source can be any reservoir that can supply a gas at pressures greater than atmospheric pressure.

Figure 46:
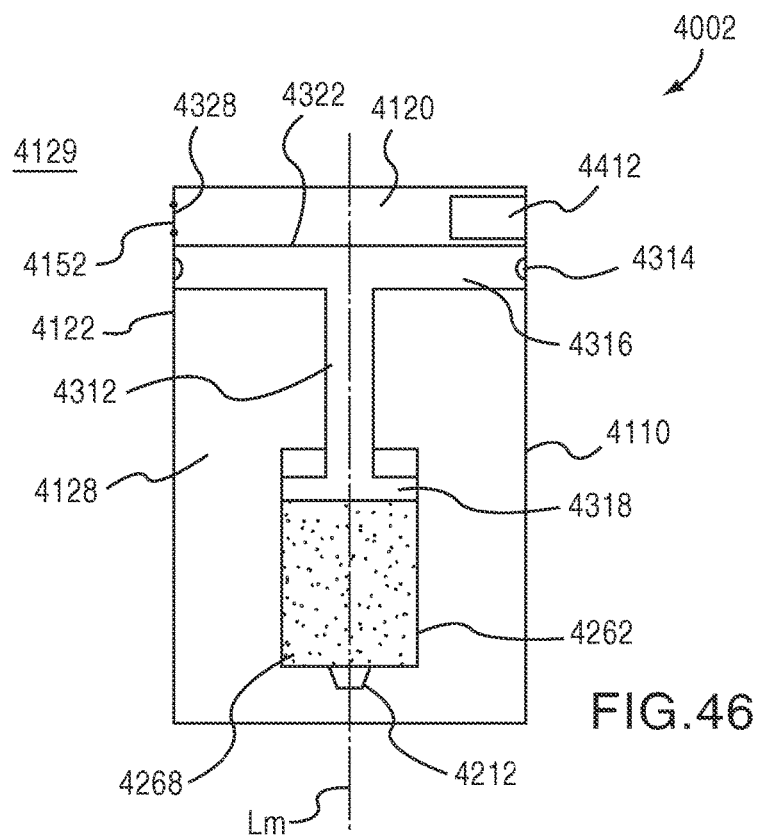
FIGS. 46-48 are schematic illustrations of an auto-injector according to an embodiment of the invention in a first configuration, a second configuration and a third configuration, respectively.
Figure 47:
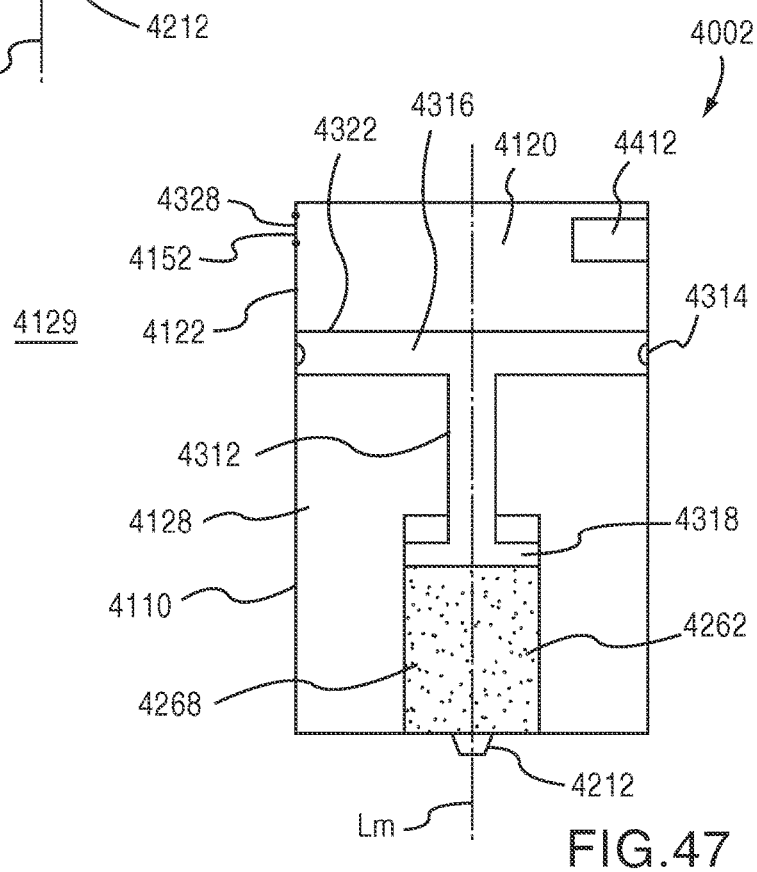
Figure 48:
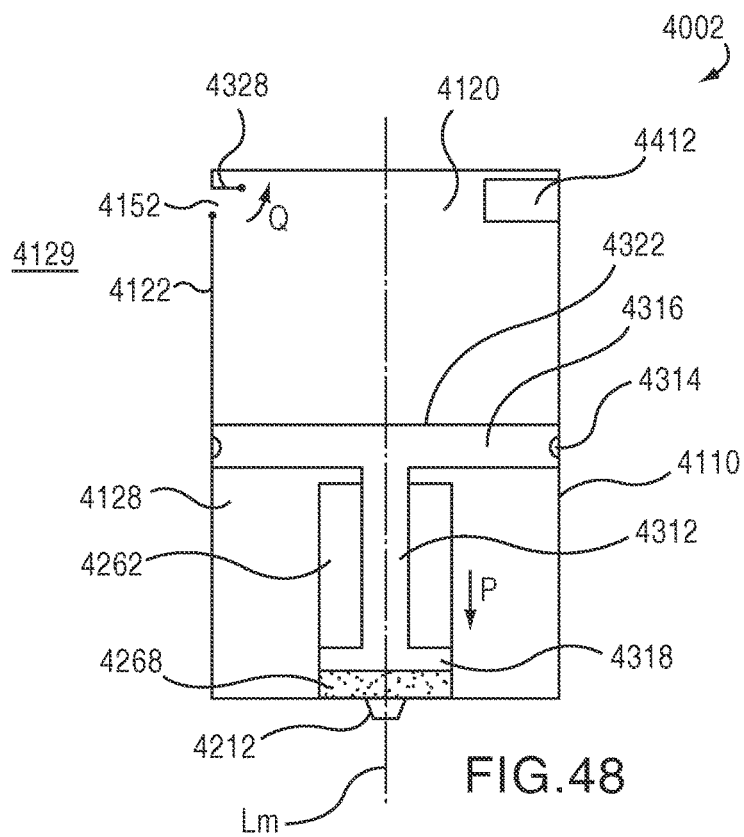

Although the auto-injectors shown and described above include a gas relief valve coupled to a movable member and configured to selectively allow fluid flow through an opening defined by the movable member, in some embodiments, the gas relief valve and/or the opening can be disposed apart from the movable member. For example, FIGS. 46-48 are schematic illustrations of an auto-injector 4002 in a first configuration, a second configuration and a third configuration, respectively. The auto-injector 4002 includes a housing 4110, a medicament container 4262, a movable member 4312, a gas relief valve 4328 and a compressed gas source 4412.

The medicament container 4262 is movably disposed within the housing 4110 and defines a longitudinal axis Lm. An injection member 4212 is coupled to and can be placed in fluid communication with the medicament container 4262. The injection member 4212 can be, for example, a needle, a nozzle or the like. As illustrated, the medicament container 4262 can be moved along its longitudinal axis Lm between a first position (FIG. 46) and a second position (FIG. 47). When the medicament container 4262 is in its first (or retracted) position, the injection member 4212 is disposed within the housing 4110. When the medicament container 4262 is in the second (or advanced) position (FIG. 47), a portion of the injection member 4212 is disposed outside of the housing 4110 and is placed in fluid communication with the medicament container 4262. In this manner, when the medicament container 4262 is in the second (or advanced) position, a medicament 4268 can be conveyed via the injection member 4212 from the medicament container 4262 into a body of a patient. In some embodiments, the injection member 4212 is disposed adjacent an outer surface of the housing, but can be able to deliver a medicament into a body.

The movable member 4312 includes a proximal end portion 4316 and a distal end portion 4318. As described above, the proximal end portion 4316 includes a surface 4322 that, together with the housing 4110, defines a gas chamber 4120. The proximal end portion 4316 also includes a seal 4314 that engages a portion of the housing to fluidically isolate the gas chamber 4120 from an area 4128 within the housing 4110. The distal end portion 4318 is disposed within and movable within the medicament container 4262 along the longitudinal axis Lm.

The housing 4110 includes a side wall 4122 that defines a portion of the gas chamber 4120. The side wall 4122 defines an opening 4152, which can be in fluid communication between the gas chamber 4120 and an area outside of the housing 4129. The gas relief valve 4328 is coupled to the housing 4110 such that it can selectively allow fluid communication between the gas chamber 4120 and the area outside of the housing 4129 through the opening 4152.

Similar to the operation described above, when the auto-injector 4002 is actuated, a pressurized gas flows from the compressed gas source 4412 into the gas chamber 4120. In response to a force produced by the pressurized gas, the movable member 4312 moves within the housing 4110 thereby placing the medicament container 4262 in its second position (FIG. 47). The movable member 4312 continues to move within the medicament container 4262, as indicated by arrow P in FIG. 48, to expel a medicament 4268 through the injection member 4212. When the medicament container 4262 is in is second position, the gas relief valve 4328 is actuated as indicated by the arrow Q in FIG. 48, thereby allowing pressurized gas to flow from the gas chamber 4120 to the area outside of the housing 4129 through the opening 4152. The gas relief valve 4328 can be actuated by any suitable valve actuator. For example, in some embodiments the auto-injector 4002 can include a mechanical valve actuator (not shown) that the user manually depresses to actuate the valve 4328.

Figure 49:
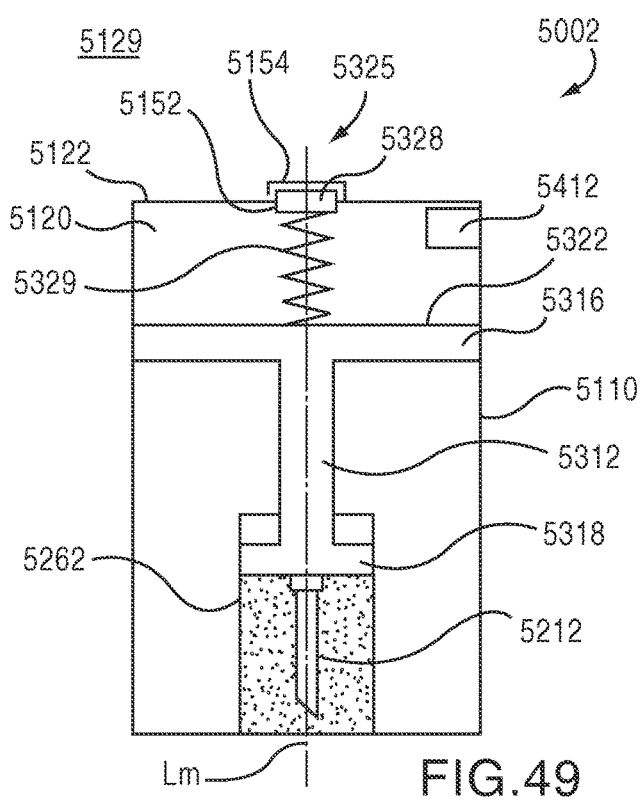
FIGS. 49 and 50 are schematic illustrations of an auto-injector according to an embodiment of the invention in a first configuration and a second configuration, respectively.
Figure 50:
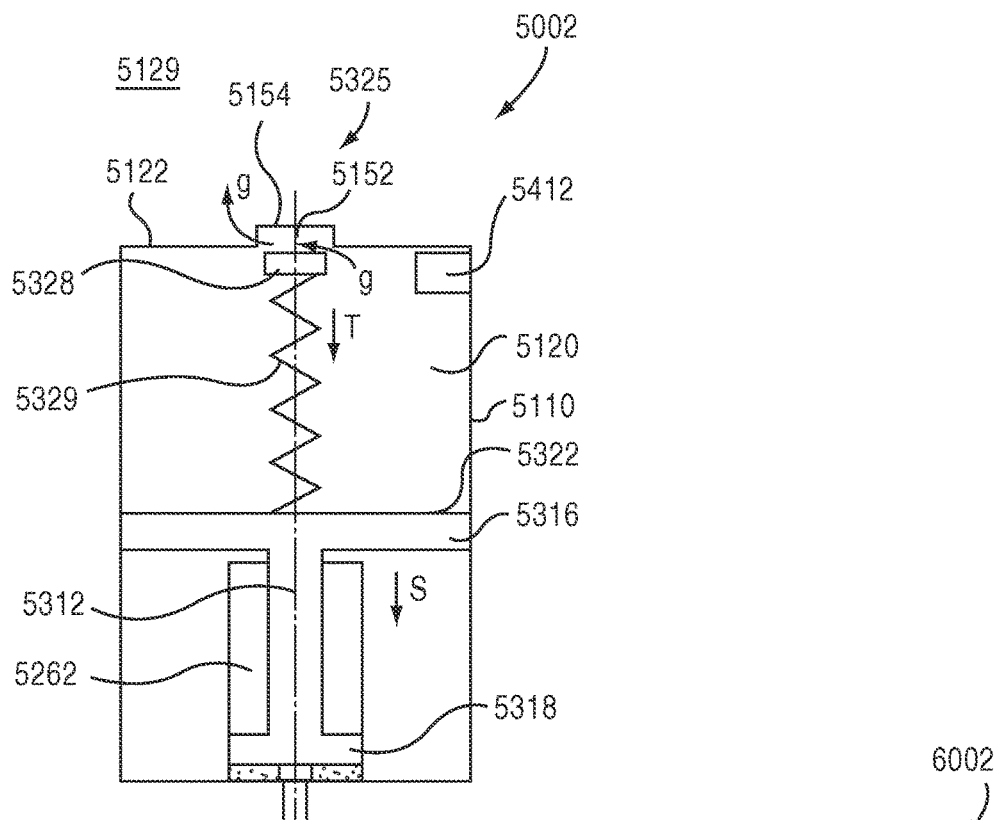

FIGS. 49 and 50 are schematic illustrations of an auto-injector 5002 in a first configuration and a second configuration, respectively. The auto-injector 5002 includes a housing 5110, a medicament container 5262, a movable member 5312, a compressed gas source 5412 and a gas release assembly 5325. As described above, the medicament container 5262 is fixedly disposed within the housing 5110 and defines a longitudinal axis Lm.

The movable member 5312 includes a proximal end portion 5316 and a distal end portion 5318. The proximal end portion 5316 includes a surface 5322 that defines a portion of a boundary of a gas chamber 5120. The distal end portion 5318 is movably disposed within the medicament container 5262 along the longitudinal axis Lm, as shown by the arrow S. A needle 5212 defining a lumen and a side opening (not shown) is coupled to the distal end 5318 of the movable member 5312.

The gas release assembly 5325 includes a gas relief valve 5328, a flexible member 5329 and an opening 5152. The opening 5152 is defined by a side wall 5122 of the housing 5110 that defines a portion of the gas chamber 5120. In this manner, the opening 5152 can provide fluid communication between the gas chamber 5120 and an area outside of the housing 5129. The housing 5110 includes a covering portion 5154 disposed adjacent the opening 5152 to prevent the opening 5152 from becoming obstructed, to prevent the gas relief valve 5328 from being inadvertently actuated or the like.

The gas relief valve 5328 is removably disposed within the opening 5152 and has a first configuration (FIG. 49) and a second configuration (FIG. 50). When the gas relief valve 5328 is in its first configuration, it is disposed within the opening 5152 such that it fluidically isolates the gas chamber 5120 from the area outside of the housing 5129. When the gas relief valve 5328 is in its second configuration, it is removed from the opening 5152, thereby placing the gas chamber 5120 in fluid communication with the area outside of the housing 5129. The gas relief valve 5328 can be, for example, a rigid member that is press fit within the opening 5152, a flexible member that is secured about the opening 5152 by an adhesive, a frangible sealing member or any other suitable device that can be removably disposed within and/or about the opening 5152.

The gas relief valve 5328 is coupled to the movable member 5312 by a flexible member 5329. By coupling the gas relief valve 5328 to the movable member 5312, the gas relief valve 5328 can be moved from its first configuration to its second configuration when the movable member 5312 reaches a predetermined position within the housing 5110. Moreover, after the gas relief valve 5328 has been actuated, this arrangement allows the gas relief valve 5328 to remain in its second configuration independent of the position of the movable member 5312. The flexible member 5329 can be any suitable structure for coupling the gas relief valve 5328 to the movable member 5312. For example, the flexible member can be a string, an elastic member, a biasing member or the like.

In use, when the auto-injector 5002 is actuated, a pressurized gas flows from the compressed gas source 5412 into the gas chamber 5120. In response to a force produced by the pressurized gas, the movable member 5312 moves within the housing 5110 and the medicament container 5262. As a result, the needle 5212 is extended through the housing 5110 and the medicament is injected via the needle 5212. When the movable member 5312 reaches a predetermined position within the housing 5110, the flexible member 5329 moves the gas relief valve 5328 into its second configuration, as shown by the arrow T in FIG. 50. In this manner, pressurized gas flows from the gas chamber 5120 to the area outside of the housing 5129 through the opening 5152, as shown by the arrows g. As the pressure in the gas chamber 5120 is reduced, the movable member 5312 and the needle 5212 can be retracted into the housing 5110, as described above.

Although the auto-injector 3002 is shown and described as including a gas relief valve 3328 that is automatically actuated by a valve actuator 3254 disposed on the carrier 3250, in some embodiments, an auto-injector can include a gas relief valve that is automatically actuated by any type of valve actuator. For example, in some embodiments, an auto-injector can include a gas relief valve that is actuated electronically, magnetically, hydraulically, pneumatically or by any other suitable mechanism. In other embodiments, an auto-injector can include a gas relief valve that is manually actuated by the user, for example, by a push button that extends within the housing.

Figure 51:
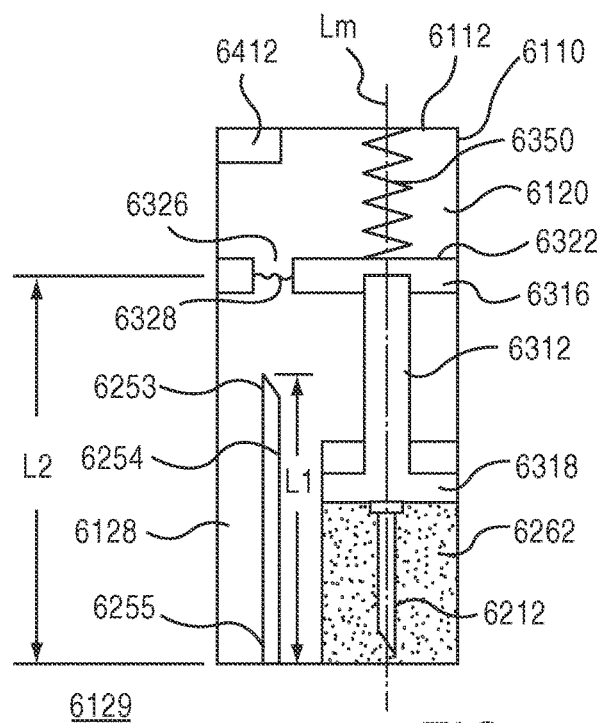
FIGS. 51-53 are schematic illustrations of an auto-injector according to an embodiment of the invention in a first configuration, a second configuration and a third configuration, respectively.
Figure 52:
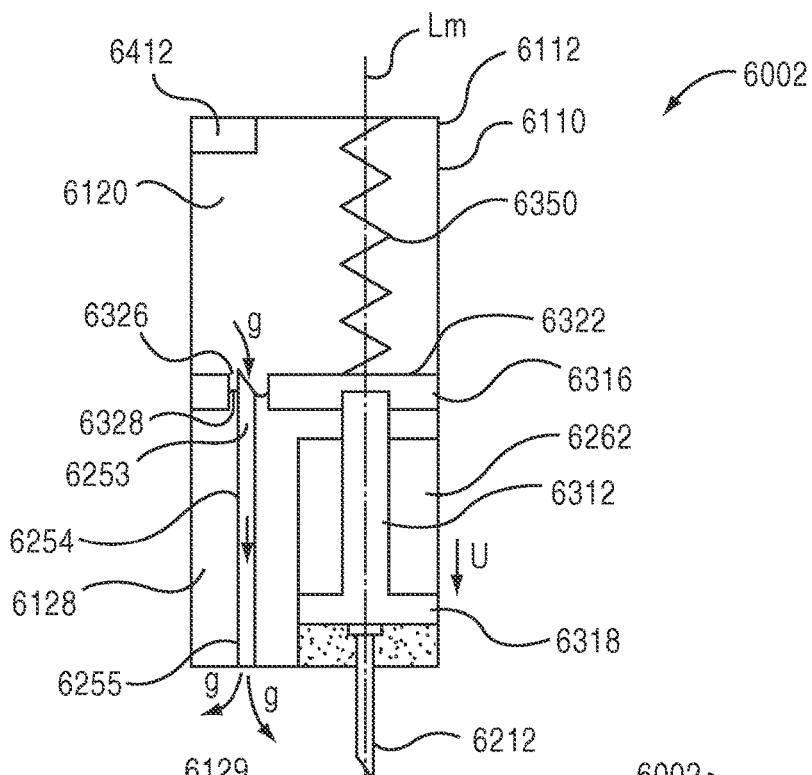
Figure 53:
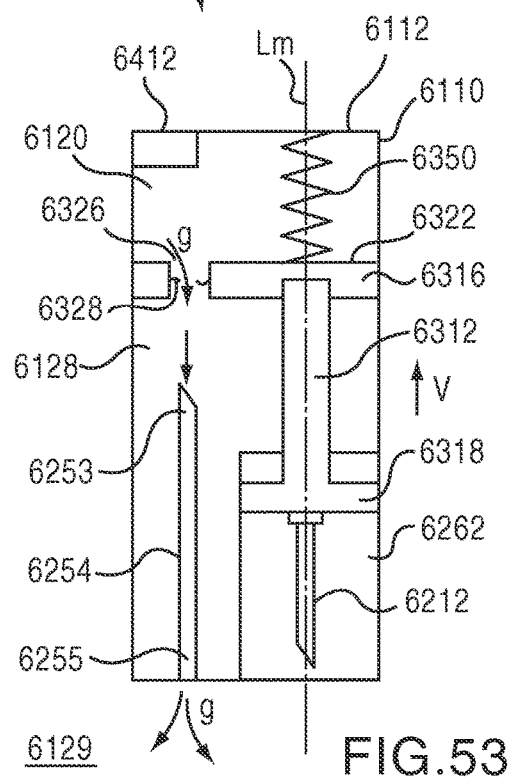

Although the auto-injector 3002 shown and described above includes a valve actuator 3254 coupled to the carrier 3250, in some embodiments, an auto-injector can include a valve actuator disposed anywhere within the auto-injector. For example, FIGS. 51-53 are schematic illustrations of an auto-injector 6002 in a first configuration, a second configuration and a third configuration, respectively, in which a valve actuator 6254 is coupled to a housing 6110. The auto-injector 6002 includes the housing 6110, a medicament container 6262, a movable member 6312, a gas relief valve 6328, the valve actuator 6254 and a compressed gas source 6412. As described above, the medicament container 6262 is fixedly disposed within the housing 6110 and defines a longitudinal axis Lm.

The movable member 6312 includes a proximal end portion 6316 and a distal end portion 6318. The proximal end portion 6316 includes a surface 6322 that defines a portion of a boundary of a gas chamber 6120. The proximal end portion 6316 defines an opening 6326 therethrough, which can be selectively placed in fluid communication between the gas chamber 6120 and an area outside of the gas chamber 6128. The distal end portion 6318 is movably disposed within the medicament container 6262 along the longitudinal axis Lm, as shown by the arrow U. A needle 6212 defining a lumen and a side opening (not shown) is coupled to the distal end 6318 of the movable member 6312.

A biasing member 6350 extends between the proximal end portion 6316 of the movable member 6312 and the housing 6110. The biasing member, which can be, for example, a spring, an elastic member or the like, is configured to bias the movable member 6312 towards the proximal portion 6112 of the housing 6110.

The gas relief valve 6328 is coupled to the movable member 6312 adjacent the opening 6326 and has a first configuration (FIG. 51) and a second configuration (FIGS. 52-53). When the gas relief valve 6328 is in its first configuration, it is disposed within the opening 6326 such that it fluidically isolates the gas chamber 6120 from the area outside of the gas chamber 6128. When the gas relief valve 6328 is in its second configuration, it is moved or punctured, thereby placing the gas chamber 6120 in fluid communication with the area outside of the gas chamber 6128.

The valve actuator 6254 has a proximal end 6253 and a distal end 6255 and defines a lumen therethrough (not shown). The proximal end 6253 of the valve actuator 6254 is configured to move or puncture the gas relief valve 6328 to move the gas relief valve 6328 between its first configuration and its second configuration. The distal end 6255 of the valve actuator 6254 is coupled to the housing 6110. In use, when the auto-injector 6002 is actuated, the gas chamber 6120 is placed in fluid communication with the compressed gas source 6412, thereby allowing a pressurized gas to flow into the gas chamber 6120. The force produced by the pressurized gas on the surface 6322 of the movable member 6312 causes the movable member 6312 to move within the housing 6110 and the medicament container 6262, as shown in FIG. 52. As a result, the needle 6212 is extended through the housing 6110 and the medicament is injected via the needle 6212.

When the movable member 6312 reaches a predetermined position within the housing 6110, the proximal end 6253 of the valve actuator 6254 punctures the gas relief valve 6328, thereby causing the gas relief valve 6328 to move irreversibly into its second configuration. In this manner, pressurized gas flows from the gas chamber 6120 to the area outside of the gas chamber 6128 through the opening 6326, as shown by the arrows g. The pressurized gas also flows from the area outside of the gas chamber 6128 to an area outside of the housing 6129 through the lumen defined by the valve actuator 6254. In this manner, the valve actuator 6254 defines a portion of the gas release path.

As shown in FIG. 53, when the pressurized gas flows out of the gas chamber 6120, the pressure exerted on the surface 6322 of the movable member 6312 decreases. Accordingly, the force exerted by the biasing member 6350 is sufficient to move the movable member 6312 proximally within the housing 6110, as indicated by arrow V, such that the needle 6212 is retracted into the housing 6110. Because the gas relief valve 6328 remains in its second configuration during retraction, the opening 6326 remains in fluid communication with the gas chamber 6120 and the area outside of the gas chamber 6128 independent of the position of the movable member 6312.

Additionally, the arrangement of the valve actuator 6254 can control the distance through which the movable member 6312 moves within the medicament container 6262 (i.e., the stroke of the movable member), and therefore the amount of medicament injected. As shown in FIG. 51, the stroke of the movable member 6312 is a function of the distance between the length L1 of the valve actuator 6254 and the length L2 of the movable member 6312 in its initial position. Accordingly, the stroke of the movable member 6312 can be controlled by varying the length L1 of the valve actuator 6254 and/or the length L2 of the movable member 6312 in its initial position.

The proximal end portion 6316 and the distal end portion 6318 are shown in FIGS. 51-53 as being separate components that are coupled together to form the movable member 6312. Such construction allows flexibility during manufacturing. For example, in some embodiments, the medicament container 6262 and the distal end portion 6318 are assembled in a sterile environment and later coupled to the proximal end portion 6316 in a non-sterile environment. In other embodiments, the two-piece arrangement of the movable member 6312 provides flexibility in setting the length L2. For example, when a greater dosage of medicament is required, a shim or spacer (not shown) can be placed in the assembly joint between the proximal end portion 6316 and the distal end portion 6318 to increase the length L2.

Although the stroke of the movable member 6312, and therefore the amount of medicament injected, is shown and described as being controlled by configuring the valve actuator 6254 to actuate the gas relief valve 6328 when the movable member 6312 has moved a predetermined distance within the medicament container 6262, in other embodiments, any suitable mechanism for controlling the stroke of the movable member can be used. For example, the auto-injector 3002 shown and described above is configured so that the movable member 3312 contacts the carrier 3250 to limit the stroke of the movable member 3312. In other embodiments, the stroke of the movable member can be limited by including a protrusion within the medicament container, such as a necked portion, that limits the motion of the piston within the medicament container. In other embodiments, the housing can include a protrusion to limit the stroke of the movable member. In yet other embodiments, a combination of each of the above methods for controlling the stroke of the movable member can be employed.

Figure 54:
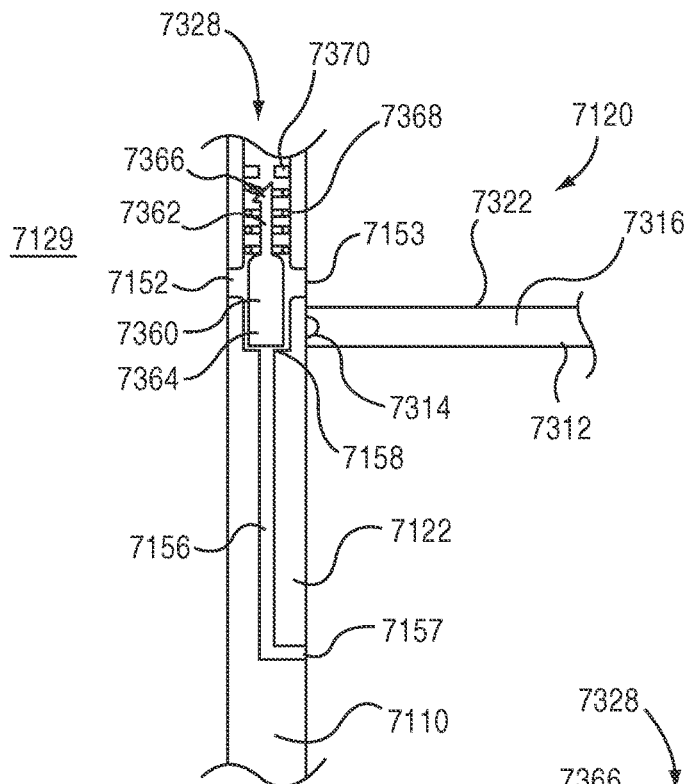
FIGS. 54 and 55 are schematic illustrations of a portion of an auto-injector according to an embodiment of the invention in a first configuration and a second configuration, respectively.
Figure 55:
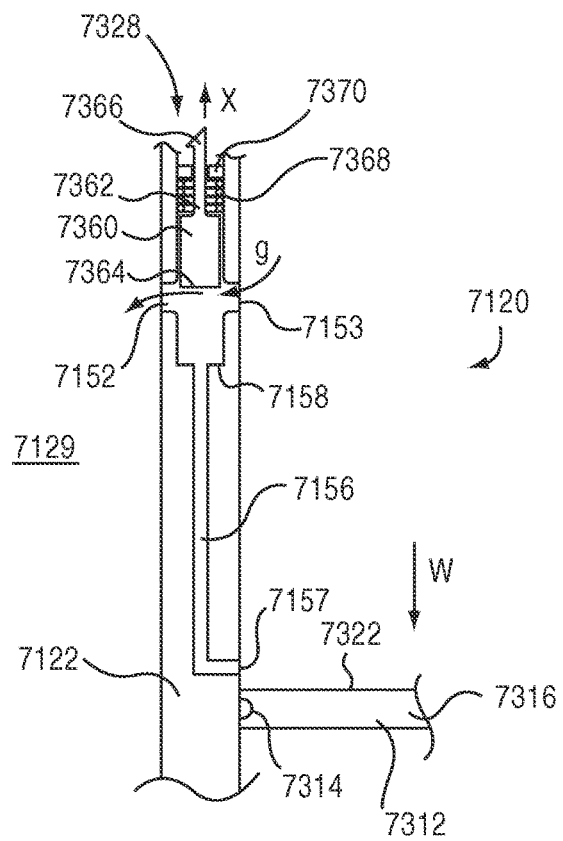

As discussed above, the valve actuator need not mechanically actuate the gas relief valve. For example, FIGS. 54 and 55 are schematic illustrations of a portion of an auto-injector 7002 having a pneumatically actuated gas relief valve 7328. Because the auto-injector 7002 is similar to the auto-injectors described above, only the gas relief mechanism is discussed in detail. The auto-injector 7002 includes a housing 7110, a movable member 7312 and a gas relief valve 7328. As described above, the movable member 7312 includes a proximal end portion 7316 that includes a surface 7322 that defines a portion of a boundary of a gas chamber 7120. The proximal end portion 7316 also includes a seal 7314 that engages a portion the housing 7110 to fluidically isolate the gas chamber 7120.

The housing 7110 includes a side wall 7122 that defines a portion of the gas chamber 7120. The side wall 7122 defines a first passageway 7152, which can be selectively placed in fluid communication between the gas chamber 7120 and an area outside of the housing 7129. The first passageway 7152 includes an opening 7153 into the gas chamber 7120 that is defined proximal to the movable member 7312. The side wall 7122 defines a second passageway 7156 that is substantially parallel to the side wall 7122 and intersects the first passageway 7152. The second passageway 7156 includes an opening 7157 selectively disposable within the gas chamber 7120 depending on the position of the movable member 7312. The opening 7157 is defined distally from the opening 7153.

The gas relief valve 7328 includes a valve body 7360, a spring 7368 and a spring retainer 7370. The valve body 7360 is movably disposed within the second passageway 7156 and has a first position (FIG. 54) and a second position (FIG. 55). The spring retainer 7370 is disposed within the second passageway 7156 and engages one end of the spring 7368. The second end of the spring 7368 engages a proximal end portion 7362 of the valve body 7360. In this manner, the valve body 7360 is biased in its first position, such that a distal end portion 7364 of the valve body 7360 engages a shoulder 7158 defined by the second passageway 7156.

When the valve body 7360 is in its first position, the valve body 7360 obstructs the first passageway 7152, thereby fluidically isolating the gas chamber 7120 from the area outside of the housing 7129. As the movable member 7312 moves distally within the housing 7110, as shown by arrow W, the seal 7314 uncovers the opening 7157 of the second passageway 7156. This allows pressurized gas from the gas chamber 7120 to flow into the second passageway 7156 and exert a force on the distal end portion 7364 of the valve body 7360. When force produced by the pressurized gas exceeds the force produced by the spring 7368, the valve body 7360 moves proximally within the second passageway 7156, as shown by arrow X. In this manner, the opening 7153 of the first passageway 7152 is uncovered, thereby allowing fluid communication between the gas chamber 7120 and the area outside of the housing 7129.

The proximal end portion 7362 of the valve body 7360 includes a projection 7366 designed to engage the spring retainer 7370 thereby maintaining the valve body 7360 in its second position. Accordingly, when the movable member 7312 moves proximally within the housing 7110 (i.e., the retraction operation) and the opening 7157 is covered by the seal 7314, the valve body 7360 will not return to its first configuration. In this manner, the gas chamber 7120 remains in fluid communication with the area outside of the housing 7129 regardless of the position of the movable member 7312, thereby ensuring that the gas chamber 7120 is fully exhausted.

Although the auto-injectors shown and described above include a gas relief valve having a first configuration in which the gas chamber is fluidically isolated and a second configuration in which the gas chamber is in fluid communication with an area outside the gas chamber, in some embodiments, an auto-injector can include a gas relief valve having more than two configurations. For example, in some configurations, an auto-injector can include a gas relief valve having a fully closed configuration, a fully opened configuration and a partially opened configuration. In this manner, the gas relief valve can be used to regulate the pressure within the gas chamber and/or the flow of the pressurized gas from the gas chamber. Such regulation can be tailored to optimize the needle insertion and/or the medicament injection operations (i.e., to ensure that the needle insertion is as painless as possible, that the medicament absorption profile is optimal, etc.).

Although the auto-injectors shown and described above include a gas relief valve that irreversibly changes from a first configuration in which the gas chamber is fluidically isolated to a second configuration in which the gas chamber is in fluid communication with an area outside the gas chamber, in some embodiments an auto-injector can include a gas relief valve configured to irreversibly change between the first configuration and the second configuration throughout the insertion and/or injection cycle. For example, in some embodiments, an auto-injector can include a gas relief valve that repeatedly cycles between its fully opened and its fully closed configurations during a single injection event. Such an arrangement also allows the gas relief valve to be used to regulate the pressure within the gas chamber and/or the flow of the pressurized gas from the gas chamber.

Figure 56:
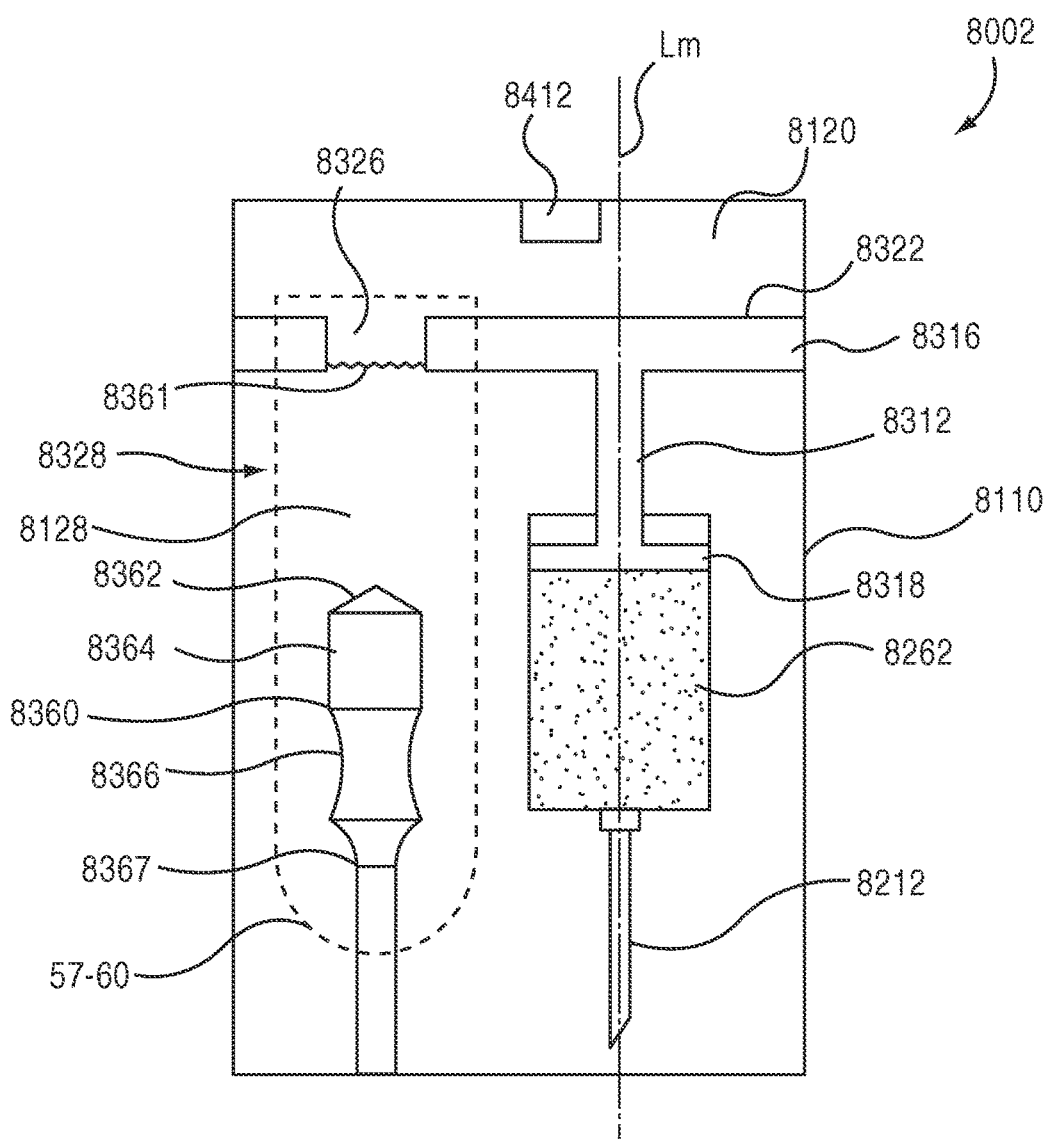
FIG. 56 is a schematic illustration of an auto-injector according to an embodiment of the invention in a first configuration.

FIG. 56 is a schematic illustration of an auto-injector 8002 in which the gas relief valve 8328 has multiple different configurations, the gas relief valve 8328 being shown in a first configuration. FIGS. 57-60 are schematic illustrations of a portion of the auto-injector 8002 in which the gas relief valve 8328 is in a second through a fifth configuration, respectively. Because the auto-injector 8002 is similar to the auto-injectors described above, only the gas relief mechanism is discussed in detail.

The auto-injector 8002 includes a housing 8110, a movable member 8312, a medicament container 8262 and a gas relief valve 8328. The medicament container 8262 is movably disposed within the housing 8110 and defines a longitudinal axis Lm. A needle 8212 is coupled to and can be placed in fluid communication with the medicament container 8262. As described above, the medicament container 8262 can be moved along its longitudinal axis Lm between a first position (FIG. 56) and a second position. When the medicament container 8262 is in its first (or retracted) position, the needle 8212 is disposed within the housing 8110. When the medicament container 8262 is in the second position, at least a portion of the needle 8212 extends outside of the housing 8110.

The movable member 8312 includes a proximal end portion 8316 and a distal end portion 8318. As described above, the proximal end portion 8316 includes a surface 8322 that, together with the housing 8110, defines a gas chamber 8120. The proximal end portion 8316 also defines an opening 8326 therethrough, which can be selectively placed in fluid communication with the gas chamber 8120 and an area outside of the gas chamber 8128. The distal end portion 8318 is movably disposed within the medicament container 8262.

The gas relief valve 8328 includes a frangible seal 8361 and a valve body 8360. The frangible seal 8361 is coupled to the movable member 8312 adjacent the opening 8326. When the gas relief valve 8328 is in its first configuration (FIG. 56) the frangible seal 8361 fluidically isolates the gas chamber 8120 from the area outside of the gas chamber 8128. When gas relief valve 8328 is in its second through fifth configurations (FIGS. 57-60), the frangible seal 8361 is moved or punctured, which as described below, can allow fluid communication between the gas chamber 8120 and the area outside the gas chamber 8128 via the opening 8326. The valve body 8360 is coupled to the housing 8110 and is configured to be disposed within the opening 8326 when the movable member 8312 moves distally within the housing 8110. The valve body includes a first portion 8362, a second portion 8364, a third portion 8366 and a fourth portion 8367.

Figure 61:
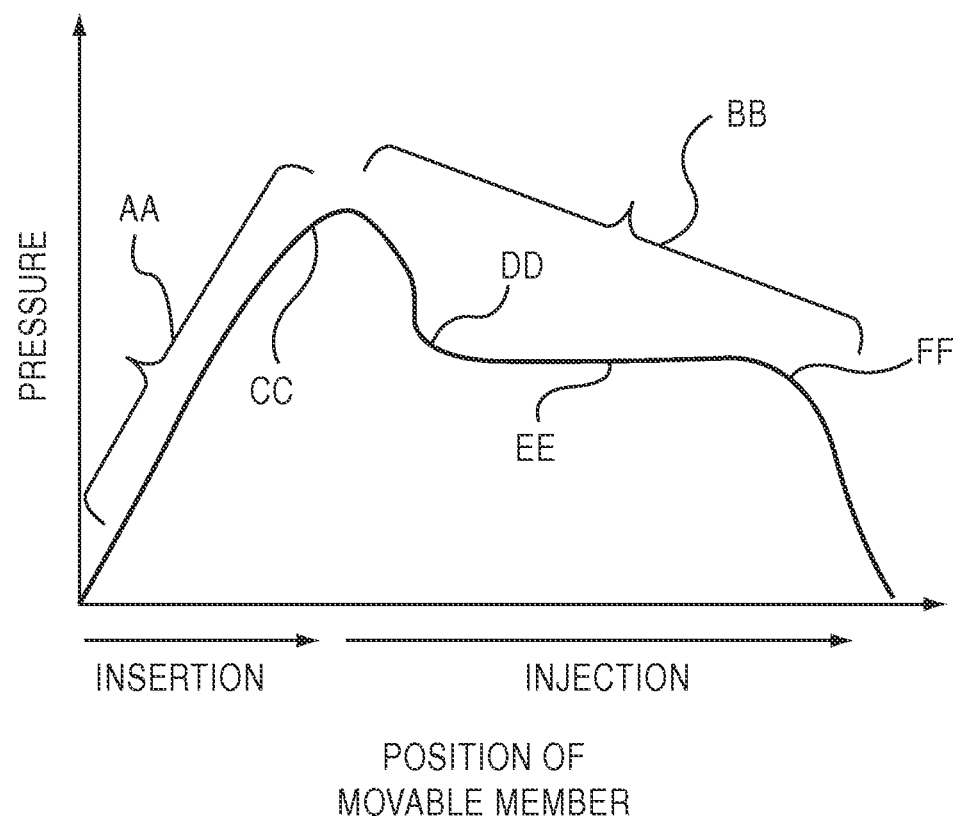
FIG. 61 is a plot showing the pressure within the auto-injector shown in FIG. 56 as a function of the position of a portion of the auto-injector.

The operation of the auto-injector 8002 and the various configurations of the gas relief valve 8128 are discussed with reference to FIG. 61, which shows a plot of the pressure within the gas chamber 8120 as a function of the position of the movable member 8312. In FIG. 61, the position of the movable member 8312, which also corresponds to the configuration of the gas relief valve, is represented on the x-axis. The pressure within the gas chamber 8120 is represented on the y-axis.

Figure 57:
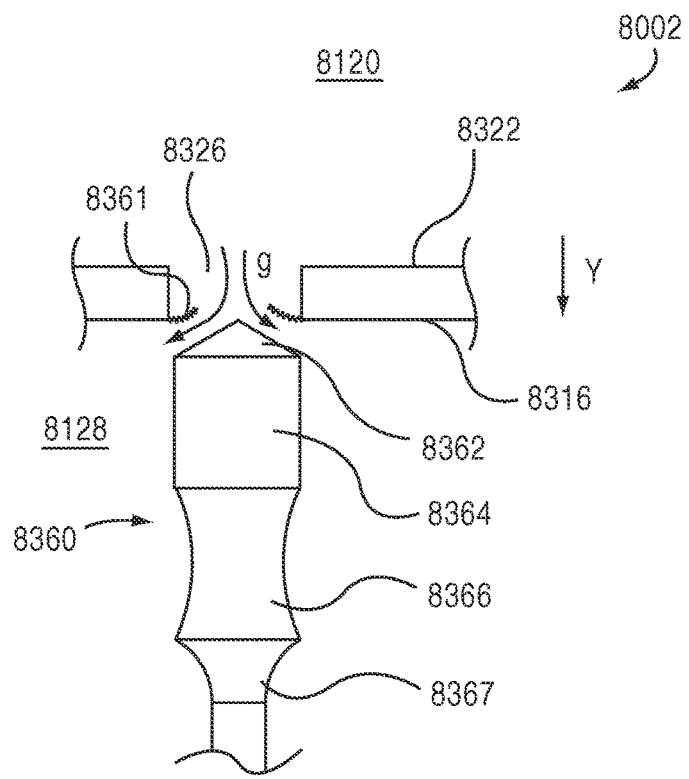
FIGS. 57-60 are schematic illustrations of a portion of the auto-injector labeled as 57-60 in FIG. 56 in a second configuration, a third configuration, a fourth configuration and a fifth configuration, respectively.

In use, when the auto-injector 8002 is actuated, a pressurized gas flows from a compressed gas source 8412 (see FIG. 56) into the gas chamber 8120, causing the movable member 8312 to move distally within the housing. The movable member 8312 moves the medicament container 8262 between its first and its second position (the "needle insertion" operation). The needle insertion operation is shown in FIG. 61 as region AA. As shown in FIG. 57, towards the end of the needle insertion operation, the movable member 8312 is positioned such that the first portion 8362 of the valve body 8360 moves or punctures the frangible seal 8361, thereby placing the gas relief valve 8128 in its second configuration (point CC on the plot in FIG. 61). When the gas relief valve is in its second configuration, the gas chamber 8120 is in fluid communication with the area outside the gas chamber 8128 via the opening 8326. Accordingly, the pressure within the gas chamber 8120 is reduced, as indicated in FIG. 61. Reducing the pressure during the needle insertion operation can, for example, reduce patient discomfort during the needle insertion operation.

Figure 58:
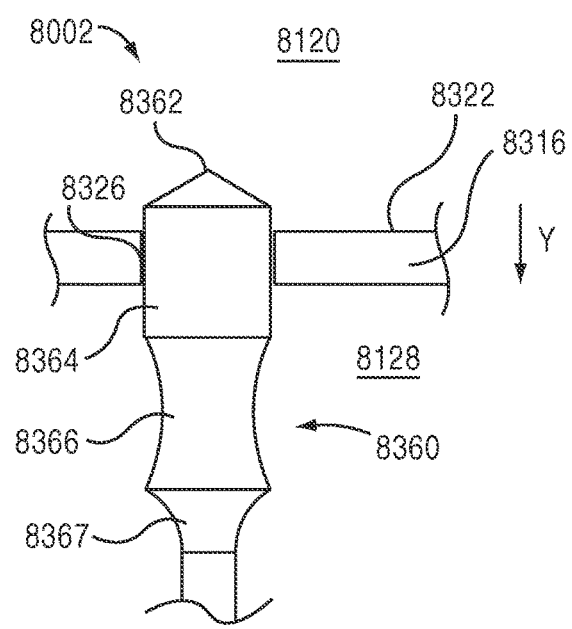
Figure 59:
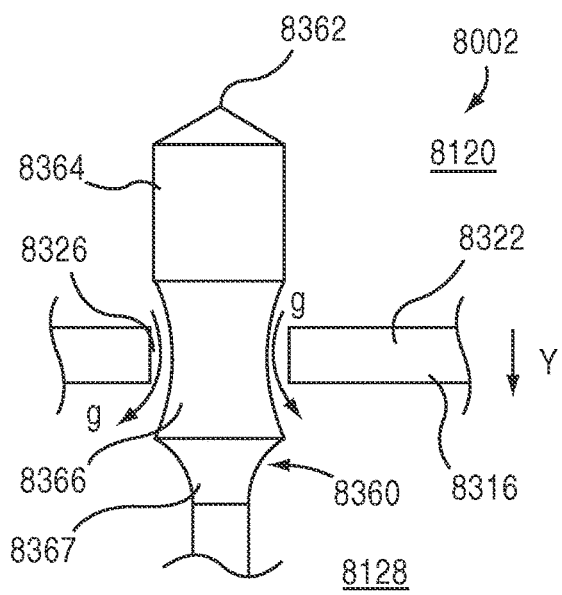
Figure 60:
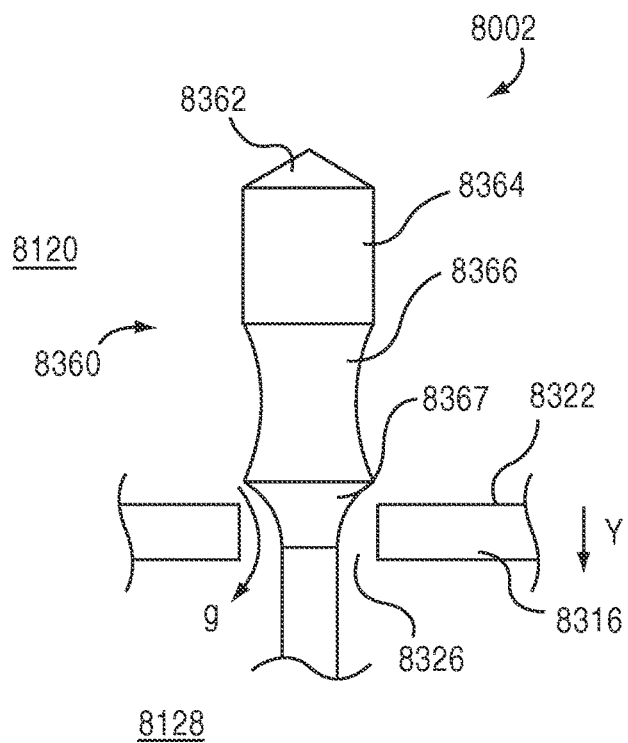

When the medicament container 8262 reaches its second position, the movable member 8312 continues to move distally within the medicament container 8262, as shown by arrow Y, to inject the medicament through the needle 8212. The medicament injection operation is shown in FIG. 61 as region BB. As shown in FIG. 58, during the beginning of the injection operation, the movable member 8312 is positioned such that the second portion 8364 of the valve body 8360 is disposed within the opening 8326, placing the gas relief valve 8128 in its third configuration (point DD on the plot in FIG. 61). The second portion 8364 of the valve body 8360 is configured to fit within the opening 8326 such that the gas chamber 8120 is substantially fluidically isolated from the area outside of the gas chamber 8128. Because pressurized gas continues to flow from the compressed gas source (not shown) into the gas chamber 8120, by fluidically isolating the gas chamber 8120, the pressure within the gas chamber 8120 will no longer decrease, but will instead remain constant or increase slightly.

During the middle portion of the injection operation, the movable member 8312 is positioned such that the third portion 8366 of the valve body 8360 is disposed within the opening 8326, placing the gas relief valve 8128 in its fourth configuration (point EE on the plot in FIG. 61). The third portion 8366 of the valve body 8360 is shaped to allow a controlled amount of pressurized gas to flow from the gas chamber 8120 to the area outside the gas chamber 8128 via the opening 8326. Said another way, the third portion 8366 of the valve body 8360 and the opening 8326 define a flow passageway between the gas chamber 8120 and an area outside the gas chamber 8128. The flow passageway varies based on the shape of the third portion 8366 of the valve body 8360. For example, a narrow shaped third portion 8364 results in a larger flow area, whereas a larger shaped third portion 8366 results in a smaller flow area. In this manner, the flow area can be varied as a function of a longitudinal position of the movable member 8312. The third portion 8366 can be shaped such that the pressurized gas entering the gas chamber 8120 from the compressed gas source (not shown) is equal to the pressurized gas exiting the gas chamber 8120. Accordingly, as shown in FIG. 61, the pressure within the gas chamber 8120 can be substantially constant throughout the injection operation.

At the end of the injection operation, the movable member 8312 is positioned such that the fourth portion 8367 of the valve body 8360 is disposed within the opening 8326, placing the gas relief valve 8128 in its fifth configuration (point FF on the plot in FIG. 61). The fourth portion 8367 of the valve body 8360 is considerably smaller than the third portion 8366, thereby allowing a significant amount of pressurized gas to flow from the gas chamber 8120 to the area outside the gas chamber 8128 via the opening 8326. Said another way, when the fourth portion 8367 of the valve body 8360 is within the opening 8326, the valve 8128 is "fully opened." Accordingly, as shown in FIG. 61, the pressure within the gas chamber 8120 decreases rapidly. In some embodiments, the rapid drop in pressure allows the movable member 8312 to be retracted by a biasing member. In this manner, the needle 8212 is also retracted into the housing 8110, thereby minimizing post-injection hazards.

Although the gas relief valve 8128 is described as being a mechanical component that varies a flow area as a function of the movable member, in other embodiments, the gas relief valve can be any suitable type of variable area valve. For example, in some embodiments, a gas relief valve can be an electrically operated spool valve.

While the valve body 8360 is shown as having four distinct regions corresponding to four variably functional positions, in other embodiments, the valve body can have fewer or greater distinct regions corresponding to a different number of functional positions. Additionally, the shapes and sizes of the illustrated valve body portions 8362, 8364, 8366 and 8367 are shown by way of example only. In some embodiments, the valve body can be shaped according to a desired pressure and/or injection profile.

Although the auto-injectors are shown and described above as having a single gas chamber and a single gas relief valve, in some embodiments, an auto-injector can include any number of gas chambers and/or gas relief valves. For example, in some embodiments, an auto-injector can include a compressed gas source, an auxiliary gas chamber and a primary gas chamber. In a similar manner as described above, the compressed gas source can be selectively placed in fluid communication with the auxiliary gas chamber, thereby allowing the auxiliary gas chamber to be filled with a pressurized gas. The auto-injector can include a first gas relief valve configured to selectively place the auxiliary gas chamber in fluid communication with the primary gas chamber. When pressurized gas is conveyed from the auxiliary gas chamber into the primary gas chamber via the first gas relief valve, the gas pressure within the primary gas chamber causes an injection event, as described above. The auto-injector can also include a second gas relief valve configured to selectively place the primary gas chamber in fluid communication with an area outside of the auto-injector housing. By including an auxiliary gas chamber, which can be vented independently from the primary gas chamber, the auto-injector can be configured as a multiple-use injector.

Similarly, while the auto-injectors are shown and described above as having an area outside of the gas chamber that is in fluid communication with an area outside of the housing, in some embodiments, the area outside of the gas chamber need not be vented to the atmosphere. For example, in some embodiments, an auto-injector can include an area outside of the gas chamber that is in fluid communication with a secondary gas chamber.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although various embodiments have been described as having particular features and/or combinations of components, other embodiments are possible having a combination of any features and/or components from any of embodiments where appropriate. For example, in some embodiments, a gas relief mechanism can include an first opening defined by the movable member that can be selectively placed in fluid communication with the gas chamber and an area outside of the gas chamber and a second opening defined by the housing that can be selectively placed in fluid communication with the gas chamber and an area outside of the housing.

What is claimed is:

1. An apparatus, comprising:
   a housing defining a gas chamber;
   a medicament container disposed within the housing;
   a needle fluidically coupled to the medicament container, the needle configured to move between a first needle position, in which the needle is disposed within the housing, and a second needle position in which a portion of the needle extends from the housing;
   a retraction spring configured to bias the needle towards the first needle position;
   an expandable assembly configured to transition between a collapsed configuration and an expanded configuration, the expandable assembly including a proximal member and a distal member; and
   an energy storage member configured to produce a pressurized gas within the gas chamber, the pressurized gas exerting a force to move the needle from the first needle position to the second needle position and to move the distal member of the expandable assembly within the medicament container to convey a medicament from the medicament container via the needle, the proximal member of the expandable assembly configured to actuate a valve to release the pressurized gas from the gas chamber when the expandable assembly is transitioned from the collapsed configuration to the expanded configuration.

2. The apparatus of claim 1, wherein the retraction spring causes the needle to move towards the first needle position after the pressurized gas is released from the gas chamber.

3. The apparatus of claim 1, wherein the expandable assembly has a first size when in the collapsed configuration and a second size when in the expanded configuration, the expandable assembly being transitioned from the collapsed configuration to the expanded configuration when the distal member of the expandable assembly moves within the medicament container such that the proximal member actuates the valve after the medicament is conveyed from the medicament container.

4. The apparatus of claim 1, wherein a length of the expandable assembly increases when the distal member of the expandable assembly moves within the medicament container to convey the medicament.

5. The apparatus of claim 1, wherein:
   the proximal member of the expandable assembly is coupled to the valve; and
   a length of the expandable assembly increases when the distal member of the expandable assembly moves within the medicament container to convey the medicament, the proximal member actuating the valve when the distal member moves a predetermined distance within the medicament container.

6. The apparatus of claim 1, wherein:
   a length of the expandable assembly increases when the distal member of the expandable assembly moves within the medicament container to convey the medicament;
   the retraction spring causes the needle to move from the second needle position towards the first needle position after the pressurized gas is released from the gas chamber; and
   the length of the expandable assembly decreases when the needle moves from the second position towards the first needle position.

7. The apparatus of claim 1, further comprising:
   the valve, the valve being any one of a rigid member, a flexible member, or a frangible seal about an opening.

8. The apparatus of claim 1, wherein the medicament container contains the medicament, the medicament being any one of a drug or a biologic product.

9. The apparatus of claim 1, wherein the medicament container contains the medicament, the medicament being a biologic product containing at least one of a hormone or an antidote.

10. The apparatus of claim 1, wherein the medicament container contains the medicament, the medicament being epinephrine.

11. An apparatus, comprising:
a housing defining a gas chamber;
a medicament container disposed within the housing;
a needle fluidically coupled to the medicament container, the needle configured to move between a first needle position, in which the needle is disposed within the housing, and a second needle position in which a portion of the needle extends from the housing;
a valve configured to move relative to the housing between a first valve position and a second valve position, the valve configured to fluidically isolate the gas chamber from an external volume when the valve is in the first valve position, the gas chamber in fluid communication with the external volume when the valve is in the second valve position;
an expandable assembly disposed within the housing, a proximal end portion of the expandable assembly coupled to the valve, a distal end portion of the expandable assembly disposed within the medicament container, the expandable assembly configured to move the valve from the first valve position to the second valve position when the expandable assembly is transitioned from a collapsed configuration to an expanded configuration; and
an energy storage member configured to produce a pressurized gas within the gas chamber, the pressurized gas exerting a force to move the needle from the first needle position to the second needle position and to move the distal end portion of the expandable assembly within the medicament container to convey a medicament from the medicament container via the needle.

12. The apparatus of claim 11, wherein the expandable assembly has a first length when in the collapsed configuration and a second length when in the expanded configuration, the second length greater than the first length.

13. The apparatus of claim 11, wherein a length of the expandable assembly increases when the distal end portion of the expandable assembly moves within the medicament container to convey the medicament.

14. The apparatus of claim 11, wherein the expandable assembly is transitioned from the collapsed configuration to the expanded configuration when the distal end portion of the expandable assembly moves within the medicament container such that the valve is moved to the second valve position after the medicament is conveyed from the medicament container.

15. The apparatus of claim 14, further comprising:
a retraction spring configured to move the needle from the second needle position towards the first needle position after the valve is moved to the second valve position.

16. The apparatus of claim 15, wherein the expandable assembly is configured to maintain the valve in the second valve position when the needle moves from the second needle position towards the first needle position.

17. The apparatus of 11, wherein the expandable assembly includes a flexible member.

18. The apparatus of claim 11, wherein a portion of the valve is press fit within an opening defined by the housing to fluidically isolate the gas chamber from the external volume when the valve is in the first valve position, the gas chamber in fluid communication with the external volume via the opening when the valve is in the second valve position.

19. An apparatus, comprising:
a housing defining a gas chamber;
a medicament container disposed within the housing;
a needle coupled to the medicament container, the needle configured to move between a first needle position, in which the needle is disposed within the housing, and a second needle position in which a portion of the needle extends from the housing;
a valve configured to transition between a first valve configuration and a second valve configuration when actuated, the valve including a seal surface that engages a portion of the housing to fluidically isolate the gas chamber from an external volume when the valve is in the first valve configuration, the seal surface disengaged from the portion of the housing when the valve is in the second valve configuration;
an expandable assembly disposed within the housing, a first member of the expandable assembly coupled to the valve, a second member of the expandable assembly disposed within the medicament container, the expandable assembly having a first length when the second member is at a first position within the medicament container, the expandable assembly having a second length when the second member is at a second position within the medicament container, the first member configured to actuate the valve when the expandable assembly is transitioned from its first length to its second length; and
an energy storage member configured to produce a pressurized gas within the gas chamber, the pressurized gas exerting a force to move the second member of the expandable assembly within the medicament container to convey a medicament from the medicament container via the needle when the needle is in the second needle position.

20. The apparatus of claim 19, wherein the seal surface of the valve is press fit within an opening defined by the housing to fluidically isolate the gas chamber from the external volume when the valve is in the first valve configuration.

21. The apparatus of claim 20, wherein the seal surface of the valve defines at least a portion of a flow path through which the pressurized gas flows when the valve is in the second valve configuration.

22. The apparatus of claim 19, further comprising:
a retraction spring configured to move the needle from the second needle position towards the first needle position after the valve is moved to the second valve configuration.

23. The apparatus of claim 19, wherein:
the expandable assembly transitions from its second length towards its first length when the needle moves from the second position towards the first needle position, the expandable assembly is configured to maintain the valve in the second valve configuration when the expandable assembly transitions from its second length towards its first length.

* * * * *